(12) United States Patent
Chong et al.

(10) Patent No.: US 11,946,045 B2
(45) Date of Patent: *Apr. 2, 2024

(54) COMPOSITIONS COMPRISING A VARIANT POLYPEPTIDE AND USES THEREOF

(71) Applicant: Arbor Biotechnologies, Inc., Cambridge, MA (US)

(72) Inventors: Shaorong Chong, Arlington, MA (US); Wei-Cheng Lu, Cambridge, MA (US); Brendan Jay Hilbert, Natick, MA (US); Quinton Norman Wessells, Cambridge, MA (US); Lauren E. Alfonse, Boston, MA (US); Anthony James Garrity, Hingham, MA (US)

(73) Assignee: Arbor Biotechnologies, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/148,748

(22) Filed: Dec. 30, 2022

(65) Prior Publication Data

US 2023/0287403 A1    Sep. 14, 2023

Related U.S. Application Data

(63) Continuation of application No. PCT/US2022/019525, filed on Mar. 9, 2022.

(60) Provisional application No. 63/176,021, filed on Apr. 16, 2021, provisional application No. 63/158,738, filed on Mar. 9, 2021.

(51) Int. Cl.
  *C12N 15/11*   (2006.01)
  *C12N 9/22*    (2006.01)

(52) U.S. Cl.
  CPC ............... *C12N 15/11* (2013.01); *C12N 9/22* (2013.01); *C12N 2310/20* (2017.05)

(58) Field of Classification Search
  None
  See application file for complete search history.

(56) References Cited

U.S. PATENT DOCUMENTS

2014/0010816 A1   1/2014   Chen et al.
2019/0002875 A1   1/2019   Cheng et al.

FOREIGN PATENT DOCUMENTS

WO   2020247882 A1   12/2020
WO   2021007177 A1   1/2021
WO   2021050534 A1   3/2021

OTHER PUBLICATIONS

International Search Report and Written Opinion for International Application No. PCT/US2022/0419525 dated Jul. 26, 2022.

*Primary Examiner* — Aurora M Fontainhas
*Assistant Examiner* — Jennifer A Benavides
(74) *Attorney, Agent, or Firm* — K&L Gates LLP

(57) ABSTRACT

The present invention relates to variant polypeptides, methods of preparing the variant polypeptides, processes for characterizing the variant polypeptides, compositions and cells comprising the variant polypeptides, and methods of using the variant polypeptides. The invention further relates to complexes comprising the variant polypeptides, methods of producing the complexes, processes for characterizing the complexes, cells comprising the complexes, and methods of using the complexes.

23 Claims, 4 Drawing Sheets

Specification includes a Sequence Listing.

COMPOSITIONS COMPRISING A VARIANT POLYPEPTIDE AND USES THEREOF

RELATED APPLICATIONS

This application is a continuation of International Patent Application No. PCT/US2022/019525, filed Mar. 9, 2022, which claims priority to U.S. Provisional Application 63/158,738 filed on Mar. 9, 2021 and U.S. Provisional Application 63/176,021 filed on Apr. 16, 2021, the entire contents of each of which are hereby incorporated by reference.

SEQUENCE LISTING

The instant application contains a Sequence Listing which has been submitted electronically in XML format and is hereby incorporated by reference in its entirety. Said XML copy, created on Dec. 28, 2022 is named A2186-704520FT.xml and is 136,397 bytes in size.

BACKGROUND

Clustered Regularly Interspaced Short Palindromic Repeats (CRISPR) and CRISPR-associated (Cas) genes, collectively known as CRISPR-Cas or CRISPR/Cas systems, are adaptive immune systems in archaea and bacteria that defend particular species against foreign genetic elements.

SUMMARY OF THE INVENTION

It is against the above background that the present invention provides certain advantages and advancements over the prior art.

Although this invention disclosed herein is not limited to specific advantages or functionalities, the invention provides, in some aspects, a variant polypeptide comprising a sequence having at least 95% identity to a sequence set forth in any one of SEQ ID NOs: 14-41 or 49-58.

In some embodiments, the variant polypeptide is a variant of a parent polypeptide of SEQ ID NO: 3. In some embodiments, the variant polypeptide comprises a substitution of Table 2.

In some embodiments, the variant polypeptide comprises one or more of the following substitutions: E38R, T60R, D89R, S223R, E319R, P353G, L354G, Q355G, D356G, N357G, N358G, Q359G, L360G, K368G, Q421R, T480K, D482K, N501K, L523R, L523K, Q556R, Q556K, V557R, E566K, E566R, E571R, E571K, N579K, E586G, E589K, N620R, Q683K, S722K, and D730R.

In some aspects, the present disclosure provides a variant polypeptide comprising an amino acid sequence having at least 95% identity to SEQ ID NO: 3 and comprising a substitution at one or more of positions E38, T60, D89, S223, E319, P353, L354, Q355, D356, N357, N358, Q359, L360, K368, Q421, T480, D482, N501, L523, Q556, V557, E566, E571, N579, E586, E589, N620, Q683, S722, and D730 relative to SEQ ID NO: 3.

In some aspects, the present disclosure provides a variant polypeptide comprising an amino acid sequence having at least 95% identity to SEQ ID NO: 3 and comprising one or more of the following substitutions: E38R, T60R, D89R, S223R, E319R, P353G, L354G, Q355G, D356G, N357G, N358G, Q359G, L360G, K368G, Q421R, T480K, D482K, N501K, L523R, L523K, Q556R, Q556K, V557R, E566K, E566R, E571R, E571K, N579K, E586G, E589K, N620R, Q683K, S722K, and D730R.

In some embodiments, the variant polypeptide comprises the sequence set forth in any one of SEQ ID NOs: 14-41 or 49-58. In some embodiments, the variant polypeptide comprises the sequence set forth in SEQ ID NO: 39. In some embodiments, the variant polypeptide comprises the sequence set forth in SEQ ID NO: 51. In some embodiments, the variant polypeptide exhibits increased binary complex formation with an RNA guide, relative to a parent polypeptide. In some embodiments, a binary complex comprising the variant polypeptide exhibits increased stability, relative to a parent binary complex. In some embodiments, the variant polypeptide exhibits increased nuclease activity, relative to a parent polypeptide.

In some aspects, the present disclosure provides a composition comprising a variant polypeptide as described herein, wherein the composition further comprises an RNA guide or a nucleic acid encoding the RNA guide, wherein the RNA guide comprises a direct repeat sequence and a spacer sequence.

In some embodiments, the direct repeat sequence is at least 90% identical to SEQ ID NO: 4 or SEQ ID NO: 5 or comprises a sequence having at least 90% identity to SEQ ID NO: 6 or SEQ ID NO: 7. In some embodiments, the direct repeat sequence is at least 95% identical to SEQ ID NO: 4 or SEQ ID NO: 5 or comprises a sequence having at least 95% identity to SEQ ID NO: 6 or SEQ ID NO: 7. In some embodiments, the direct repeat sequence is SEQ ID NO: 4 or SEQ ID NO: 5 or comprises a sequence of SEQ ID NO: 6 or SEQ ID NO: 7.

In some embodiments, the spacer sequence comprises about 15 nucleotides to about 35 nucleotides in length. In some embodiments, the spacer sequence binds to a target strand sequence of a target nucleic acid, and wherein a non-target strand sequence of the target nucleic acid sequence is adjacent to a protospacer adjacent motif (PAM) sequence. In some embodiments, the PAM sequence is 5'-NNR-3', 5'-TNR-3', 5'-NTTN-3', 5'-NTTR-3', or 5'-TTTN-3', wherein N is any nucleotide and R is A or G. In some embodiments, the PAM sequence is 5'-TTG-3', 5'-TTTG-3', 5'-TTA-3', 5'-TTTA-3', or 5'-ATTG-3'.

In some embodiments, the variant polypeptide further comprises a nuclear localization signal (NLS). In some embodiments, the variant polypeptide further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some aspects, the present disclosure provides a composition comprising a nucleic acid that encodes a variant polypeptide and/or the RNA guide as described herein.

In some embodiments, the nucleic acid is codon-optimized for expression in a cell. In some embodiments, the nucleic acid is operably linked to a promoter. In some embodiments, the nucleic acid is in a vector. In some embodiments, the vector comprises a retroviral vector, a lentiviral vector, a phage vector, an adenoviral vector, an adeno-associated vector, or a herpes simplex vector. In some embodiments, the variant polypeptide is present in a delivery system comprising a nanoparticle (e.g., a lipid nanoparticle), a liposome, an exosome, a microvesicle, or a gene-gun.

In some aspects, the present disclosure provides a cell comprising a variant polypeptide or a composition as described herein.

In some embodiments, the cell is a eukaryotic cell. In some embodiments, the cell is a mammalian cell or a plant cell. In some embodiments, the cell is a human cell.

In some aspects, the present disclosure provides a composition comprising a variant polypeptide or a complex comprising the variant polypeptide, wherein the variant polypeptide comprises a sequence having at least 95% identity to a sequence set forth in any one of SEQ ID NOs: 14-41 or 49-58, and wherein the variant polypeptide or the complex exhibits enhanced enzymatic activity, enhanced binding activity, enhanced binding specificity, and/or enhanced stability, relative to a parent polypeptide or a complex comprising the parent polypeptide.

In some embodiments, the variant polypeptide comprises a substitution of Table 2. In some embodiments, the variant polypeptide comprises one or more of the following substitutions: E38R, T60R, D89R, S223R, E319R, P353G, L354G, Q355G, D356G, N357G, N358G, Q359G, L360G, K368G, Q421R, T480K, D482K, N501K, L523R, L523K, Q556R, Q556K, V557R, E566K, E566R, E571R, E571K, N579K, E586G, E589K, N620R, Q683K, S722K, and D730R.

In some embodiments, the variant polypeptide comprises the sequence set forth in any one of SEQ ID NOs: 14-41 or 49-58. In some embodiments, the variant polypeptide comprises the sequence set forth in SEQ ID NO: 39. In some embodiments, the variant polypeptide comprises the sequence set forth in SEQ ID NO: 51.

In some embodiments, the enhanced enzymatic activity is enhanced nuclease activity. In some embodiments, the variant polypeptide exhibits enhanced binding activity to an RNA guide, relative to the parent polypeptide. In some embodiments, the variant polypeptide exhibits enhanced binding specificity to an RNA guide, relative to the parent polypeptide. In some embodiments, the complex comprising the variant polypeptide is a variant binary complex that further comprises an RNA guide, and the variant binary complex exhibits enhanced binding activity to a target nucleic acid (e.g., on-target binding activity), relative to a parent binary complex. In some embodiments, the complex comprising the variant polypeptide is a variant binary complex that further comprises an RNA guide, and the variant binary complex exhibits enhanced binding specificity to a target nucleic acid (e.g., on-target binding specificity), relative to a parent binary complex. In some embodiments, the complex comprising the variant polypeptide is a variant binary complex that further comprises an RNA guide, and the variant binary complex exhibits enhanced stability, relative to a parent binary complex. In some embodiments, the variant binary complex and a target nucleic acid form a variant ternary complex, and the variant ternary complex exhibits increased stability, relative to a parent ternary complex. In some embodiments, the variant polypeptide further exhibits enhanced binary complex formation, enhanced protein-RNA interactions, and/or decreased dissociation from an RNA guide, relative to the parent polypeptide. In some embodiments, the variant binary complex further exhibits decreased dissociation from a target nucleic acid, and/or decreased off-target binding to a non-target nucleic acid, relative to the parent binary complex.

In some embodiments, the enhanced enzymatic activity, enhanced binding activity, enhanced binding specificity, and/or enhanced stability occur over a range of temperatures, e.g., 20° C. to 65° C. In some embodiments, the enhanced enzymatic activity, enhanced binding activity, enhanced binding specificity, and/or enhanced stability occur over a range of incubation times. In some embodiments, the enhanced enzymatic activity, enhanced binding activity, enhanced binding specificity, and/or enhanced stability occur in a buffer having a pH in a range of about 7.3 to about 8.6. In some embodiments, the enhanced enzymatic activity, enhanced binding activity, enhanced binding specificity, and/or enhanced stability occurs when a $T_m$ value of the variant polypeptide, variant binary complex, or variant ternary complex is at least 8° C. greater than the $T_m$ value of the parent polypeptide, parent binary complex, or parent ternary complex.

In some embodiments, the variant polypeptide comprises a RuvC domain or a split RuvC domain. In some embodiments, the parent polypeptide comprises the sequence of SEQ ID NO: 3.

In some embodiments, the RNA guide comprises a direct repeat sequence and a spacer sequence. In some embodiments, the direct repeat sequence is at least 90% identical to SEQ ID NO: 4 or SEQ ID NO: 5 or comprises a sequence having at least 90% identity to SEQ ID NO: 6 or SEQ ID NO: 7. In some embodiments, the direct repeat sequence is at least 95% identical to SEQ ID NO: 4 or SEQ ID NO: 5 or comprises a sequence having at least 95% identity to SEQ ID NO: 6 or SEQ ID NO: 7. In some embodiments, the direct repeat sequence is SEQ ID NO: 4 or SEQ ID NO: 5 or comprises a sequence of SEQ ID NO: 6 or SEQ ID NO: 7. In some embodiments, the spacer sequence comprises between 15 and 35 nucleotides in length. In some embodiments, the spacer sequence comprises complementarity to a target strand sequence of a target nucleic acid.

In some embodiments, the target nucleic acid comprises a non-target strand sequence adjacent to a protospacer adjacent motif (PAM) sequence. In some embodiments, the PAM sequence is 5'-NNR-3', 5'-TNR-3', 5'-NTTN-3', 5'-NTTR-3', or 5'-TTTN-3', wherein N is any nucleotide and R is A or G. In some embodiments, the PAM sequence is 5'-TTG-3', 5'-TTTG-3', 5'-TTA-3', 5'-TTTA-3', or 5'-ATTG-3'.

In some embodiments, the variant polypeptide further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some aspects, the present disclosure provides a composition comprising a nucleic acid that encodes a variant polypeptide as described herein, wherein optionally the nucleic acid is codon-optimized for expression in a cell.

In some embodiments, the cell is a eukaryotic cell. In some embodiments, the cell is a mammalian cell or a plant cell. In some embodiments, the cell is a human cell.

In some embodiments, the nucleic acid encoding the variant polypeptide is operably linked to a promoter. In some embodiments, the nucleic acid encoding the variant polypeptide is in a vector. In some embodiments, the vector comprises a retroviral vector, a lentiviral vector, a phage vector, an adenoviral vector, an adeno-associated vector, or a herpes simplex vector.

In some embodiments, the composition is present in a delivery composition comprising a nanoparticle (e.g., a lipid nanoparticle), a liposome, an exosome, a microvesicle, or a gene-gun.

In some aspects, the present disclosure provides a method for editing a gene in a cell, the method comprising contacting the cell with a variant polypeptide or composition as described herein.

In some aspects, the present disclosure provides a nucleic acid molecule encoding a variant polypeptide as described herein.

In some embodiments, the nucleic acid molecule is 95% identical to a sequence selected from the group consisting of SEQ ID NOs: 59-66.

In some aspects, the present disclosure provides a nucleic acid molecule encoding a variant polypeptide of SEQ ID NO: 39, wherein the sequence of the nucleic acid molecule is 95% identical to a sequence selected from the group consisting of SEQ ID NOs: 59-66.

In some embodiments, the sequence of the nucleic acid molecule comprises a sequence selected from the group consisting of SEQ ID NOs: 59-66.

Although this invention disclosed herein is not limited to specific advantages or functionalities, the invention provides a variant polypeptide, and/or a composition comprising a variant polypeptide, wherein the variant polypeptide comprises an alteration relative to the parent polypeptide of SEQ ID NO: 3, and wherein the variant polypeptide or a complex comprising the variant polypeptide exhibits enhanced enzymatic activity, enhanced binding activity, enhanced binding specificity, and/or enhanced stability relative to the parent polypeptide or a complex comprising the parent polypeptide.

In some aspects, the enhanced enzymatic activity is enhanced nuclease activity.

In some aspects, the variant polypeptide exhibits enhanced binding activity to an RNA guide relative to the parent polypeptide.

In some aspects, the variant polypeptide exhibits enhanced binding specificity to an RNA guide relative to the parent polypeptide.

In some aspects, the variant polypeptide and an RNA guide form a variant binary complex, and the variant binary complex exhibits enhanced binding activity to a target nucleic acid (e.g., on-target binding activity) relative to a parent binary complex.

In some aspects, the variant polypeptide and an RNA guide form a variant binary complex, and the variant binary complex exhibits enhanced binding specificity to a target nucleic acid (e.g., on-target binding specificity) relative to a parent binary complex.

In some aspects, the variant polypeptide and an RNA guide form a variant binary complex, and the variant binary complex exhibits enhanced stability relative to a parent binary complex.

In some aspects, the variant binary complex and a target nucleic acid form a variant ternary complex, and the variant ternary complex exhibits increased stability relative to a parent ternary complex.

In some aspects, the variant polypeptide further exhibits enhanced binary complex formation, enhanced protein-RNA interactions, and/or decreased dissociation from an RNA guide relative to the parent polypeptide.

In some aspects, the variant binary complex further exhibits decreased dissociation from the target nucleic acid, and/or decreased off-target binding to a non-target nucleic acid relative to the parent binary complex.

In some aspects, the enhanced enzymatic activity, enhanced binding activity, enhanced binding specificity, and/or enhanced stability occur over a range of temperatures, e.g., 20° C. to 65° C.

In some aspects, the enhanced enzymatic activity, enhanced binding activity, enhanced binding specificity, and/or enhanced stability occur over a range of incubation times.

In some aspects, the enhanced enzymatic activity, enhanced binding activity, enhanced binding specificity, and/or enhanced stability occur in a buffer having a pH in a range of about 7.3 to about 8.6.

In some aspects, the enhanced enzymatic activity, enhanced binding activity, enhanced binding specificity, and/or enhanced stability occurs when a $T_m$ value of the variant polypeptide, variant binary complex, or variant ternary complex is at least 8° C. greater than the $T_m$ value of the parent polypeptide, parent binary complex, or parent ternary complex.

In other aspects, the alteration comprises an amino acid sequence alteration relative to the parent polypeptide having the sequence set forth in SEQ ID NO: 3, wherein the alteration comprises one or more (e.g., one, two, three, four, five, or more) substitutions, insertions, deletions, and/or additions as compared to the parent polypeptide having the sequence set forth in SEQ ID NO:3.

In some aspects, the alteration comprises an amino acid sequence alteration relative to the parent polypeptide sequence set forth in SEQ ID NO: 3, wherein the alteration comprises one or more of the amino acid substitutions listed in Table 2.

In some aspects, the alteration comprises an arginine, lysine, glutamine, asparagine, histidine, alanine, or glycine substitution.

In some aspects, the alteration comprises an E38R, T60R, D89R, S223R, P353G, L354G, L360G, K368G, E566R, and/or D730R substitution.

In some aspects, the variant polypeptide comprises an amino acid sequence having at least 90% identity to any one of SEQ ID NOs: 14-41.

In some aspects, the variant polypeptide comprises an amino acid sequence having at least 95% identity to any one of SEQ ID NOs: 14-41.

In some aspects, the variant polypeptide comprises the amino acid sequence of any one of SEQ ID NOs: 14-41.

In some aspects, the variant polypeptide comprises a RuvC domain or a split RuvC domain.

In some aspects, the variant polypeptide comprises one or more catalytic residues (e.g., aspartic acid or glutamic acid). In some aspects, the one or more catalytic residues comprise D336 and E545. In some aspects, the one or more catalytic residues comprise D695, D661, or D636.

In some aspects, the composition or complex comprising the variant polypeptide further comprises an RNA guide, and the RNA guide comprises a direct repeat sequence and a spacer sequence.

In some aspects, the direct repeat sequence comprises a nucleotide sequence with at least 95% sequence identity to SEQ ID NO: 4 or SEQ ID NO: 5.

In some aspects, the direct repeat sequence comprises the nucleotide sequence of SEQ ID NO: 4 or SEQ ID NO: 5.

In some aspects, the spacer sequence comprises between 15 and 35 nucleotides in length.

In some aspects, the target nucleic acid comprises a sequence complementary to a nucleotide sequence in the spacer sequence.

In some aspects, the target nucleic acid is adjacent to a protospacer adjacent motif (PAM) sequence, wherein the PAM sequence comprises a nucleotide sequence set forth as 5'-NNR-3', 5'-TNR-3', 5'-NTTN-3', 5'-NTTR-3', or 5'-TTTN-3', wherein N is any nucleotide and R is A or G. In some aspects, the PAM sequence comprises a nucleotide sequence set forth as 5'-TTTG-3'.

In some aspects, the target nucleic acid is single-stranded DNA or double-stranded DNA.

In some aspects, the variant polypeptide further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some aspects, a nucleic acid encoding the variant polypeptide is codon-optimized for expression in a cell.

In some aspects, the nucleic acid encoding the variant polypeptide is operably linked to a promoter.

In some aspects, the nucleic acid encoding the variant polypeptide is in a vector.

In some aspects, the vector comprises a retroviral vector, a lentiviral vector, a phage vector, an adenoviral vector, an adeno-associated vector, or a herpes simplex vector.

In some aspects, the composition is present in a delivery composition comprising a nanoparticle, a liposome, an exosome, a microvesicle, or a gene-gun.

The invention yet further provides a variant polypeptide comprising an E38R substitution relative to SEQ ID NO: 3. In some aspects, the variant polypeptide comprises at least 95% identity to SEQ ID NO: 3 and further comprises an E38R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position E38 (e.g., an E38R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position E38 (e.g., an E38R substitution) relative to SEQ ID NO: 3.

The invention yet further provides a variant polypeptide comprising a T60R substitution relative to SEQ ID NO: 3. In some aspects, the variant polypeptide comprises at least 95% identity to SEQ ID NO: 3 and further comprises a T60R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position T60 (e.g., a T60R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position T60 (e.g., a T60R substitution) relative to SEQ ID NO: 3.

The invention yet further provides a variant polypeptide comprising a D89R substitution relative to SEQ ID NO: 3. In some aspects, the variant polypeptide comprises at least 95% identity to SEQ ID NO: 3 and further comprises a D89R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position D89 (e.g., a D89R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position D89 (e.g., a D89R substitution) relative to SEQ ID NO: 3.

The invention yet further provides a variant polypeptide comprising an S223R substitution relative to SEQ ID NO: 3. In some aspects, the variant polypeptide comprises at least 95% identity to SEQ ID NO: 3 and further comprises an S223R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position S223 (e.g., an S223R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position S223 (e.g., an S223R substitution) relative to SEQ ID NO: 3.

The invention yet further provides a variant polypeptide comprising a P353G substitution relative to SEQ ID NO: 3. In some aspects, the variant polypeptide comprises at least 95% identity to SEQ ID NO: 3 and further comprises a P353G substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position P353 (e.g., a P353G substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position P353 (e.g., a P353G substitution) relative to SEQ ID NO: 3.

The invention yet further provides a variant polypeptide comprising an L354G substitution relative to SEQ ID NO: 3. In some aspects, the variant polypeptide comprises at least 95% identity to SEQ ID NO: 3 and further comprises an L354G substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position L354 (e.g., an L354G substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position L354 (e.g., an L354G substitution) relative to SEQ ID NO: 3.

The invention yet further provides a variant polypeptide comprising an L360G substitution relative to SEQ ID NO: 3. In some aspects, the variant polypeptide comprises at least 95% identity to SEQ ID NO: 3 and further comprises an L360G substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position L360 (e.g., an L360G substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position L360 (e.g., an L360G substitution) relative to SEQ ID NO: 3.

The invention yet further provides a variant polypeptide comprising a K368G substitution relative to SEQ ID NO: 3. In some aspects, the variant polypeptide comprises at least 95% identity to SEQ ID NO: 3 and further comprises a K368G substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position K368 (e.g., a K368G substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position K368 (e.g., a K368G substitution) relative to SEQ ID NO: 3.

The invention yet further provides a variant polypeptide comprising an E566R substitution relative to SEQ ID NO: 3. In some aspects, the variant polypeptide comprises at least 95% identity to SEQ ID NO: 3 and further comprises an E566R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position E566 (e.g., an E566R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position E566 (e.g., an E566R substitution) relative to SEQ ID NO: 3.

The invention yet further provides a variant polypeptide comprising an E566K substitution relative to SEQ ID NO: 3. In some aspects, the variant polypeptide comprises at least 95% identity to SEQ ID NO: 3 and further comprises an E566K substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position E566 (e.g., an E566K substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position E566 (e.g., an E566K substitution) relative to SEQ ID NO: 3.

The invention yet further provides a variant polypeptide comprising a D730R substitution relative to SEQ ID NO: 3. In some aspects, the variant polypeptide comprises at least 95% identity to SEQ ID NO: 3 and further comprises a D730R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position D730 (e.g., a D730R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position D730 (e.g., a D730R substitution) relative to SEQ ID NO: 3.

The invention yet further provides a variant polypeptide comprising an E319R substitution relative to SEQ ID NO: 3. In some aspects, the variant polypeptide comprises at least 95% identity to SEQ ID NO: 3 and further comprises an E319R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position E319 (e.g., an E319R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position E319 (e.g., an E319R substitution) relative to SEQ ID NO: 3.

The invention yet further provides a variant polypeptide comprising a Q355G substitution relative to SEQ ID NO: 3. In some aspects, the variant polypeptide comprises at least 95% identity to SEQ ID NO: 3 and further comprises a Q355G substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position Q355 (e.g., a Q355G substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position Q355 (e.g., a Q355G substitution) relative to SEQ ID NO: 3.

The invention yet further provides a variant polypeptide comprising a D356G substitution relative to SEQ ID NO: 3. In some aspects, the variant polypeptide comprises at least 95% identity to SEQ ID NO: 3 and further comprises a D356G substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position D356 (e.g., a D356G substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position D356 (e.g., a D356G substitution) relative to SEQ ID NO: 3.

The invention yet further provides a variant polypeptide comprising an N357G substitution relative to SEQ ID NO: 3. In some aspects, the variant polypeptide comprises at least 95% identity to SEQ ID NO: 3 and further comprises an N357G substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position N357 (e.g., an N357G substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position N357 (e.g., an N357G substitution) relative to SEQ ID NO: 3.

The invention yet further provides a variant polypeptide comprising an N358G substitution relative to SEQ ID NO: 3. In some aspects, the variant polypeptide comprises at least 95% identity to SEQ ID NO: 3 and further comprises an N358G substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position N358 (e.g., an N358G substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position N358 (e.g., an N358G substitution) relative to SEQ ID NO: 3.

The invention yet further provides a variant polypeptide comprising a Q359G substitution relative to SEQ ID NO: 3. In some aspects, the variant polypeptide comprises at least 95% identity to SEQ ID NO: 3 and further comprises a Q359G substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position Q359 (e.g., a Q359G substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position Q359 (e.g., a Q359G substitution) relative to SEQ ID NO: 3.

The invention yet further provides a variant polypeptide comprising a Q421R substitution relative to SEQ ID NO: 3. In some aspects, the variant polypeptide comprises at least 95% identity to SEQ ID NO: 3 and further comprises a Q421R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position Q421 (e.g., a Q421R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position Q421 (e.g., a Q421R substitution) relative to SEQ ID NO: 3.

The invention yet further provides a variant polypeptide comprising a T480K substitution relative to SEQ ID NO: 3. In some aspects, the variant polypeptide comprises at least 95% identity to SEQ ID NO: 3 and further comprises a T480K substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position T480 (e.g., a T480K substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position T480 (e.g., a T480K substitution) relative to SEQ ID NO: 3.

The invention yet further provides a variant polypeptide comprising a D482K substitution relative to SEQ ID NO: 3. In some aspects, the variant polypeptide comprises at least 95% identity to SEQ ID NO: 3 and further comprises a D482K substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position D482 (e.g., a D482K substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position D482 (e.g., a D482K substitution) relative to SEQ ID NO: 3.

The invention yet further provides a variant polypeptide comprising an N501K substitution relative to SEQ ID NO: 3. In some aspects, the variant polypeptide comprises at least 95% identity to SEQ ID NO: 3 and further comprises an N501K substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position N501 (e.g., an N501K substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position N501 (e.g., an N501K substitution) relative to SEQ ID NO: 3.

The invention yet further provides a variant polypeptide comprising an L523R substitution relative to SEQ ID NO: 3. In some aspects, the variant polypeptide comprises at least 95% identity to SEQ ID NO: 3 and further comprises an L523R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position L523 (e.g., an L523R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position L523 (e.g., an L523R substitution) relative to SEQ ID NO: 3.

The invention yet further provides a variant polypeptide comprising an L523K substitution relative to SEQ ID NO: 3. In some aspects, the variant polypeptide comprises at least 95% identity to SEQ ID NO: 3 and further comprises an L523K substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position L523 (e.g., an L523K substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position L523 (e.g., an L523K substitution) relative to SEQ ID NO: 3.

The invention yet further provides a variant polypeptide comprising a Q556R substitution relative to SEQ ID NO: 3. In some aspects, the variant polypeptide comprises at least 95% identity to SEQ ID NO: 3 and further comprises a Q556R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position Q556 (e.g., a Q556R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position Q556 (e.g., a Q556R substitution) relative to SEQ ID NO: 3.

The invention yet further provides a variant polypeptide comprising a Q556K substitution relative to SEQ ID NO: 3. In some aspects, the variant polypeptide comprises at least 95% identity to SEQ ID NO: 3 and further comprises a Q556K substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position Q556 (e.g., a Q556K substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position Q556 (e.g., a Q556K substitution) relative to SEQ ID NO: 3.

The invention yet further provides a variant polypeptide comprising a V557R substitution relative to SEQ ID NO: 3. In some aspects, the variant polypeptide comprises at least 95% identity to SEQ ID NO: 3 and further comprises a V557R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position V557 (e.g., a V557R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position V557 (e.g., a V557R substitution) relative to SEQ ID NO: 3.

The invention yet further provides a variant polypeptide comprising an E571R substitution relative to SEQ ID NO: 3. In some aspects, the variant polypeptide comprises at least 95% identity to SEQ ID NO: 3 and further comprises an E571R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position E571 (e.g., an E571R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position E571 (e.g., an E571R substitution) relative to SEQ ID NO: 3.

The invention yet further provides a variant polypeptide comprising an E571K substitution relative to SEQ ID NO: 3. In some aspects, the variant polypeptide comprises at least 95% identity to SEQ ID NO: 3 and further comprises an E571K substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position E571 (e.g., an E571K substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position E571 (e.g., an E571K substitution) relative to SEQ ID NO: 3.

The invention yet further provides a variant polypeptide comprising an N579K substitution relative to SEQ ID NO: 3. In some aspects, the variant polypeptide comprises at least 95% identity to SEQ ID NO: 3 and further comprises an N579K substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position N579 (e.g., an N579K substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position N579 (e.g., an N579K substitution) relative to SEQ ID NO: 3.

The invention yet further provides a variant polypeptide comprising an E586G substitution relative to SEQ ID NO: 3. In some aspects, the variant polypeptide comprises at least 95% identity to SEQ ID NO: 3 and further comprises an E586G substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position E586 (e.g., an E586G substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position E586 (e.g., an E586G substitution) relative to SEQ ID NO: 3.

The invention yet further provides a variant polypeptide comprising an E589K substitution relative to SEQ ID NO: 3. In some aspects, the variant polypeptide comprises at least 95% identity to SEQ ID NO: 3 and further comprises an E589K substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position E589 (e.g., an E589K substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position E589 (e.g., an E589K substitution) relative to SEQ ID NO: 3.

The invention yet further provides a variant polypeptide comprising an N620R substitution relative to SEQ ID NO: 3. In some aspects, the variant polypeptide comprises at least 95% identity to SEQ ID NO: 3 and further comprises an N620R substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position N620 (e.g., an N620R substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position N620 (e.g., an N620R substitution) relative to SEQ ID NO: 3.

The invention yet further provides a variant polypeptide comprising a Q683K substitution relative to SEQ ID NO: 3. In some aspects, the variant polypeptide comprises at least 95% identity to SEQ ID NO: 3 and further comprises a Q683K substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position Q683 (e.g., a Q683K substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position Q683 (e.g., a Q683K substitution) relative to SEQ ID NO: 3.

The invention yet further provides a variant polypeptide comprising an S722K substitution relative to SEQ ID NO: 3. In some aspects, the variant polypeptide comprises at least 95% identity to SEQ ID NO: 3 and further comprises an S722K substitution relative to SEQ ID NO: 3.

In some aspects, the present disclosure provides a polypeptide comprising an amino acid sequence having at least 95%, 96%, 97%, 98%, or 99% identity to SEQ ID NO: 3 and comprising a substitution at position S722 (e.g., an S722K substitution) relative to SEQ ID NO: 3. In some aspects, the present disclosure provides a polypeptide comprising an amino acid sequence having one or more sequence alterations (e.g., substitutions, insertions, or deletions, or any combination thereof) at up to 1, 2, 3, 4, 5, 10, 15, 20, 25, 30, or 35 amino acid positions of SEQ ID NO: 3, wherein one of the sequence alterations comprises a substitution at position S722 (e.g., an S722K substitution) relative to SEQ ID NO: 3.

The invention yet further provides a variant polypeptide comprising the amino acid sequence of SEQ ID NO: 14. The invention yet further provides a variant polypeptide comprising the amino acid sequence of SEQ ID NO: 15. The invention yet further provides a variant polypeptide comprising the amino acid sequence of SEQ ID NO: 16. The invention yet further provides a variant polypeptide comprising the amino acid sequence of SEQ ID NO: 17. The invention yet further provides a variant polypeptide comprising the amino acid sequence of SEQ ID NO: 18. The invention yet further provides a variant polypeptide comprising the amino acid sequence of SEQ ID NO: 19. The invention yet further provides a variant polypeptide comprising the amino acid sequence of SEQ ID NO: 20. The invention yet further provides a variant polypeptide comprising the amino acid sequence of SEQ ID NO: 21. The invention yet further provides a variant polypeptide comprising the amino acid sequence of SEQ ID NO: 22. The invention yet further provides a variant polypeptide comprising the amino acid sequence of SEQ ID NO: 23. The invention yet further provides a variant polypeptide comprising the amino acid sequence of SEQ ID NO: 24. The invention yet further provides a variant polypeptide comprising the amino acid sequence of SEQ ID NO: 25. The invention yet further provides a variant polypeptide comprising the amino acid sequence of SEQ ID NO: 26. The invention yet further provides a variant polypeptide comprising the amino acid sequence of SEQ ID NO: 27. The invention yet further provides a variant polypeptide comprising the amino acid sequence of SEQ ID NO: 28. The invention yet further provides a variant polypeptide comprising the amino acid sequence of SEQ ID NO: 29. The invention yet further provides a variant polypeptide comprising the amino acid sequence of SEQ ID NO: 30. The invention yet further provides a variant polypeptide comprising the amino acid sequence of SEQ ID NO: 31. The invention yet further provides a variant polypeptide comprising the amino acid sequence of SEQ ID NO: 32. The invention yet further provides a variant polypeptide comprising the amino acid sequence of SEQ ID NO: 33. The invention yet further provides a variant polypeptide comprising the amino acid sequence of SEQ ID NO: 34. The invention yet further provides a variant polypeptide comprising the amino acid sequence of SEQ ID NO: 35. The invention yet further provides a variant polypeptide comprising the amino acid sequence of SEQ ID NO: 36. The invention yet further provides a variant polypeptide comprising the amino acid sequence of SEQ ID NO: 37. The invention yet further provides a variant polypeptide comprising the amino acid sequence of SEQ ID NO: 38. The invention yet further provides a variant polypeptide comprising the amino acid sequence of SEQ ID NO: 39. The invention yet further provides a variant polypeptide comprising the amino acid sequence of SEQ ID NO: 40. The invention yet further provides a variant polypeptide comprising the amino acid sequence of SEQ ID NO: 41.

The invention further provides a cell comprising the variant polypeptide and/or the composition disclosed herein. In some aspects, the cell is a eukaryotic cell or a prokaryotic cell. In some aspects, the cell is a mammalian cell or a plant cell. In some aspects, the cell is a human cell.

The invention further provides a method of preparing the variant polypeptide and/or the composition disclosed herein.

The invention further provides a method of complexing the variant polypeptide with the RNA guide disclosed herein.

The invention further provides a method of complexing the variant binary complex with the target nucleic acid disclosed herein.

The invention further provides a method of delivering the variant polypeptide and/or the composition disclosed herein.

The invention yet further provides a composition comprising a variant polypeptide, or a complex comprising the variant polypeptide and an RNA guide, wherein the variant polypeptide comprises an alteration relative to the parent polypeptide of SEQ ID NO: 3, and wherein the variant polypeptide or the complex exhibits enhanced enzymatic activity, enhanced binding activity, enhanced binding specificity, and/or enhanced stability relative to a parent polypeptide or a complex comprising the parent polypeptide and the RNA guide.

In some aspects, the enhanced enzymatic activity is enhanced nuclease activity.

In some aspects, the variant polypeptide exhibits enhanced binding activity to the RNA guide relative to the parent polypeptide.

In some aspects, the variant polypeptide exhibits enhanced binding specificity to the RNA guide relative to the parent polypeptide.

In some aspects, the variant polypeptide and the RNA guide form a variant binary complex, and the variant binary complex exhibits enhanced binding activity to a target nucleic acid (e.g., on-target binding activity) relative to a parent binary complex.

In some aspects, the variant polypeptide and the RNA guide form a variant binary complex, and the variant binary complex exhibits enhanced binding specificity to a target nucleic acid (e.g., on-target binding specificity) relative to a parent binary complex.

In some aspects, the variant polypeptide and the RNA guide form a variant binary complex, and the variant binary complex exhibits enhanced stability relative to a parent binary complex.

In some aspects, the variant binary complex and a target nucleic acid form a variant ternary complex, and the variant ternary complex exhibits increased stability relative to a parent ternary complex.

In some aspects, the variant polypeptide further exhibits enhanced binary complex formation, enhanced protein-RNA interactions, and/or decreased dissociation from the RNA guide relative to the parent polypeptide.

In some aspects, the variant binary complex further exhibits decreased dissociation from the target nucleic acid, and/or decreased off-target binding to a non-target nucleic acid relative to the parent binary complex.

In some aspects, the enhanced enzymatic activity, enhanced binding activity, enhanced binding specificity, and/or enhanced stability occur over a range of temperatures, e.g., 20° C. to 65° C.

In some aspects, the enhanced enzymatic activity, enhanced binding activity, enhanced binding specificity, and/or enhanced stability occur over a range of incubation times.

In some aspects, the enhanced enzymatic activity, enhanced binding activity, enhanced binding specificity, and/or enhanced stability occur in a buffer having a pH in a range of about 7.3 to about 8.6.

In some aspects, the enhanced enzymatic activity, enhanced binding activity, enhanced binding specificity, and/or enhanced stability occurs when a $T_m$ value of the variant polypeptide, variant binary complex, or variant ternary complex is at least 8° C. greater than the $T_m$ value of the parent polypeptide, parent binary complex, or parent ternary complex.

In other aspects, the alteration comprises an amino acid sequence alteration relative to the parent polypeptide having the sequence set forth in SEQ ID NO: 3, wherein the alteration comprises one or more (e.g., one, two, three, four, five, or more) substitutions, insertions, deletions, and/or additions as compared to the parent polypeptide having the sequence set forth in SEQ ID NO:3.

In some aspects, the alteration comprises an amino acid sequence alteration relative to the parent polypeptide sequence set forth in SEQ ID NO: 3, wherein the alteration comprises one or more of the amino acid substitutions listed in Table 2.

In some aspects, the alteration comprises an arginine, lysine, glutamine, asparagine, histidine, alanine, or glycine substitution.

In some aspects, the alteration comprises an E38R, T60R, D89R, S223R, P353G, L354G, L360G, K368G, E566R, and/or D730R substitution.

In some aspects, the variant polypeptide comprises a RuvC domain or a split RuvC domain.

In some aspects, the variant polypeptide comprises one or more catalytic residues (e.g., aspartic acid or glutamic acid). In some aspects, the one or more catalytic residues comprise D336 and E545. In some aspects, the one or more catalytic residues comprise D695, D661, or D636.

In some aspects, the RNA guide comprises a direct repeat sequence and a spacer sequence.

In some aspects, the direct repeat sequence comprises a nucleotide sequence with at least 95% sequence identity to SEQ ID NO: 4 or SEQ ID NO: 5.

In some aspects, the direct repeat sequence comprises the nucleotide sequence of SEQ ID NO: 4 or SEQ ID NO: 5.

In some aspects, the spacer sequence comprises between 15 and 35 nucleotides in length.

In some aspects, the target nucleic acid comprises a sequence complementary to a nucleotide sequence in the spacer sequence.

In some aspects, the target nucleic acid is adjacent to a PAM sequence, wherein the PAM sequence comprises a nucleotide sequence set forth as 5'-NNR-3', 5'-TNR-3', 5'-NTTN-3', 5'-NTTR-3', or 5'-TTTN-3', wherein N is any nucleotide and R is A or G. In some aspects, the PAM sequence comprises a nucleotide sequence set forth as 5'-TTTG-3'.

In some aspects, the target nucleic acid is single-stranded DNA or double-stranded DNA.

In some aspects, the variant polypeptide further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some aspects, a nucleic acid encoding the variant polypeptide is codon-optimized for expression in a cell In some aspects, the nucleic acid encoding the variant polypeptide is operably linked to a promoter.

In some aspects, the nucleic acid encoding the variant polypeptide is in a vector.

In some aspects, the vector comprises a retroviral vector, a lentiviral vector, a phage vector, an adenoviral vector, an adeno-associated vector, or a herpes simplex vector.

In some aspects, the composition or complex is present in a delivery composition comprising a nanoparticle, a liposome, an exosome, a microvesicle, or a gene-gun.

The invention further provides a cell comprising the variant polypeptide and/or the complex disclosed herein. In some aspects, the cell is a eukaryotic cell or a prokaryotic cell. In some aspects, the cell is a mammalian cell or a plant cell. In some aspects, the cell is a human cell.

The invention further provides a method of preparing the variant polypeptide and/or the complex disclosed herein.

The invention further provides a method of complexing the variant polypeptide with the RNA guide disclosed herein.

The invention further provides a method of complexing the variant binary complex with the target nucleic acid disclosed herein.

The invention further provides a method of delivering the variant polypeptide and/or the complex disclosed herein.

Definitions

The present invention will be described with respect to particular embodiments and with reference to certain Figures, but the invention is not limited thereto but only by the claims. Terms as set forth hereinafter are generally to be understood in their common sense unless indicated otherwise.

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics, and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20% or +10%, more preferably ±5%, even more preferably +10%, and still more preferably +0.10% from the specified value, as such variations are appropriate to perform the disclosed methods.

As used herein, the term "activity" refers to a biological activity. In some embodiments, nuclease activity includes enzymatic activity, e.g., catalytic ability of a nuclease. For example, nuclease activity can include nuclease activity. In some embodiments, nuclease activity includes binding activity, e.g., binding activity of a nuclease to an RNA guide and/or target nucleic acid.

As used herein, the term "complex" refers to a grouping of two or more molecules. In some embodiments, the complex comprises a polypeptide and a nucleic acid molecule interacting with (e.g. binding to, coming into contact with, adhering to) one another.

As used herein, the term "binary complex" refers to a grouping of two molecules (e.g., a polypeptide and a nucleic acid molecule). In some embodiments, a binary complex refers to a grouping of a polypeptide and a targeting moiety (e.g., an RNA guide). In some embodiments, a binary complex refers to a ribonucleoprotein (RNP). As used herein, the term "variant binary complex" refers to the grouping of a variant polypeptide and RNA guide. As used herein, the term "parent binary complex" refers to the grouping of a parent polypeptide and RNA guide or a reference polypeptide and RNA guide.

As used herein, the term "ternary complex" refers to a grouping of three molecules (e.g., a polypeptide and two nucleic acid molecules). In some embodiments, a "ternary complex" refers to a grouping of a polypeptide, an RNA molecule, and a DNA molecule. In some embodiments, a ternary complex refers to a grouping of a polypeptide, a targeting moiety (e.g., an RNA guide), and a target nucleic acid (e.g., a target DNA molecule). In some embodiments, a "ternary complex" refers to a grouping of a binary complex (e.g., a ribonucleoprotein) and a third molecule (e.g., a target nucleic acid).

As used herein, the term "domain" refers to a distinct functional and/or structural unit of a polypeptide. In some embodiments, a domain may comprise a conserved amino acid sequence.

As used herein, the terms "parent," "parent polypeptide," and "parent sequence" refer to an original polypeptide (e.g., reference or starting polypeptide) to which an alteration is made to produce a variant polypeptide of the present invention.

As used herein, the term "protospacer adjacent motif" or "PAM" refers to a DNA sequence adjacent to a target sequence to which a complex comprising an effector (e.g., a nuclease) and an RNA guide binds. In some embodiments, a PAM is required for enzyme activity. The "target nucleic acid" is a double-stranded molecule: one strand comprises the target sequence adjacent to the PAM and is referred to as the "PAM strand" (e.g., the non-target strand or the non-spacer-complementary strand), and the other complementary strand is referred to as the "non-PAM strand" (e.g., the target strand or the spacer-complementary strand). As used herein, the term "adjacent" includes instances in which an RNA guide of the complex specifically binds, interacts, or associates with a target sequence that is immediately adjacent to a PAM. In such instances, there are no nucleotides between the target sequence and the PAM. The term "adjacent" also includes instances in which there are a small number (e.g., 1, 2, 3, 4, or 5) of nucleotides between the target sequence, to which the targeting moiety binds, and the PAM.

As used herein, the terms "reference composition," "reference molecule," "reference sequence," and "reference" refer to a control, such as a negative control or a parent (e.g., a parent sequence, a parent protein, or a wild-type protein). For example, a reference molecule refers to a polypeptide to which a variant polypeptide is compared. Likewise, a reference RNA guide refers to a targeting moiety to which a modified RNA guide is compared. The variant or modified molecule may be compared to the reference molecule on the basis of sequence (e.g., the variant or modified molecule may have X % sequence identity or homology with the reference molecule), thermostability, or activity (e.g., the variant or modified molecule may have X % of the activity of the reference molecule). For example, a variant or modified molecule may be characterized as having no more than 10% of an activity of the reference polypeptide or may be characterized as having at least 10% greater of an activity of the reference polypeptide. Examples of reference polypeptides include naturally occurring unmodified polypeptides, e.g., naturally occurring polypeptides from archaea or bacterial species. In certain embodiments, the reference polypeptide is a naturally occurring polypeptide having the closest sequence identity or homology with the variant polypeptide to which it is being compared. In certain embodiments, the reference polypeptide is a parental molecule having a naturally occurring or known sequence on which a mutation has been made to arrive at the variant polypeptide.

As used herein, the terms "RNA guide" or "RNA guide sequence" refer to any RNA molecule that facilitates the targeting of a polypeptide described herein to a target nucleic acid. For example, an RNA guide can be a molecule that recognizes (e.g., binds to) a target nucleic acid. An RNA guide may be designed to be complementary to a target strand (e.g., the non-PAM strand) of a target nucleic acid sequence. An RNA guide comprises a DNA targeting sequence and a direct repeat (DR) sequence. The terms CRISPR RNA (crRNA), pre-crRNA, mature crRNA, and gRNA are also used herein to refer to an RNA guide. As used herein, the term "pre-crRNA" refers to an unprocessed RNA molecule comprising a DR-spacer-DR sequence. As used herein, the term "mature crRNA" refers to a processed form of a pre-crRNA; a mature crRNA may comprise a DR-spacer sequence, wherein the DR is a truncated form of the DR of a pre-crRNA and/or the spacer is a truncated form of the spacer of a pre-crRNA.

As used herein, the term "substantially identical" refers to a sequence, polynucleotide, or polypeptide, that has a certain degree of identity to a reference sequence.

As used herein, the terms "target nucleic acid," "target sequence," and "target substrate" refer to a nucleic acid to which an RNA guide specifically binds. In some embodiments, the DNA targeting sequence of an RNA guide binds to a target nucleic acid.

As used herein, the terms "variant polypeptide" and "variant nuclease polypeptide" refer to a polypeptide comprising an alteration, e.g., but not limited to, a substitution, insertion, deletion, addition and/or fusion, at one or more residue positions, compared to a parent polypeptide. As used herein, the terms "variant polypeptide" and "variant nuclease polypeptide" refer to a polypeptide comprising an alteration as compared to the polypeptide of SEQ ID NO: 3.

DETAILED DESCRIPTION

Figure 1:
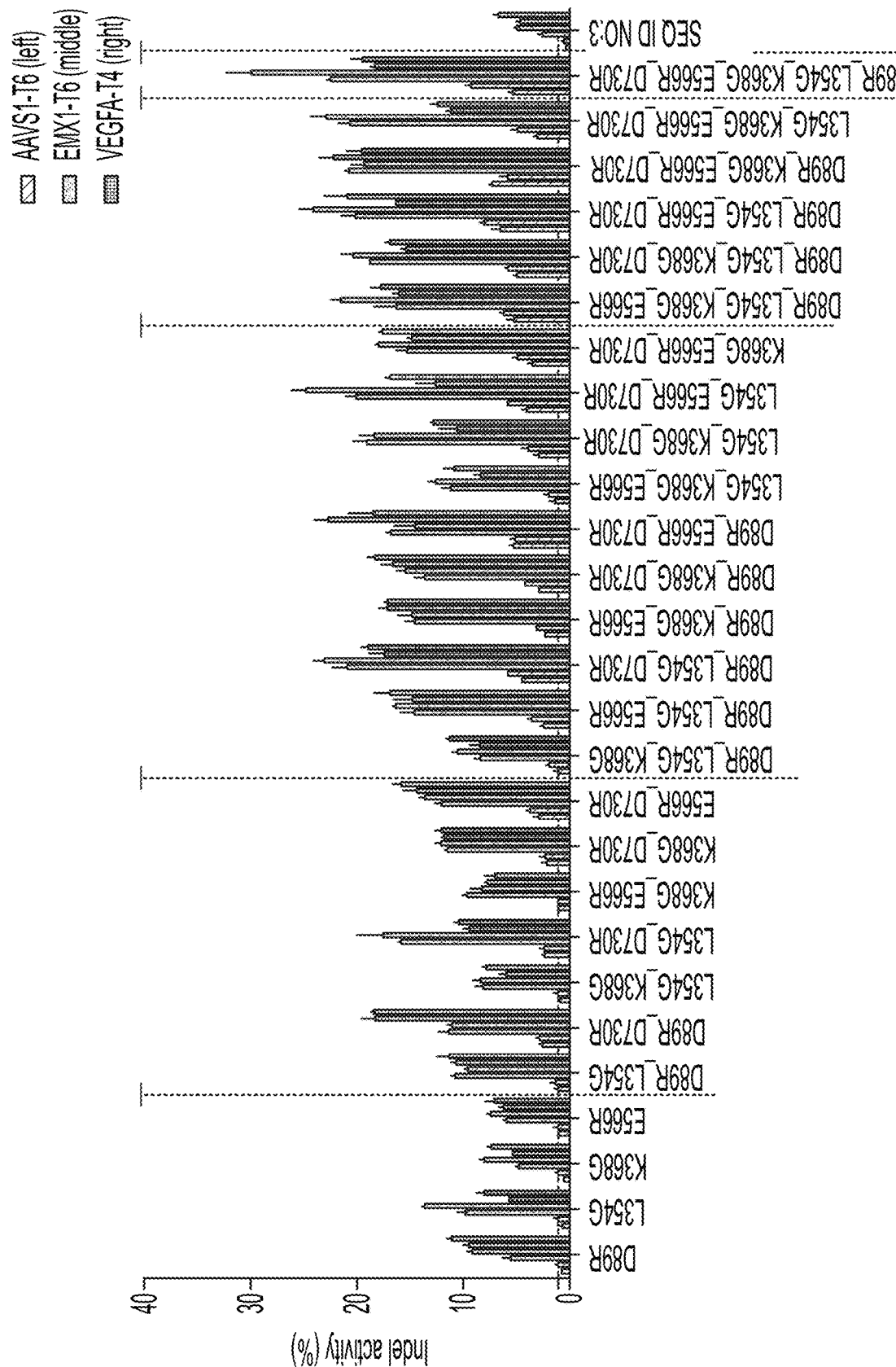
FIG. 1 shows % indels induced in an AAVS1 target (SEQ ID NO: 13), EMX1 target (SEQ ID NO: 9), and a VEGFA target (SEQ ID NO: 11) by variant polypeptides having substitutions relative to SEQ ID NO: 3, as described in Example 7. The variant polypeptides in FIG. 1 have the amino acid sequences set forth in SEQ ID NOs: 14-17 and 19-41. The bars corresponding to the AAVS1 target are the two leftmost bars for each variant, the bars corresponding to the EMX1 target are the middle two bars for each variant, and the bars corresponding to the VEGFA target are the two rightmost bars for each variant.

In some aspects, the present invention provides novel variants of the polypeptide of SEQ ID NO: 3, compositions comprising the variants, and methods of preparation and use thereof. In other aspects, the present invention further provides complexes comprising a variant of the polypeptide of SEQ ID NO: 3 and compositions, methods of preparation and use thereof. In some aspects, a composition comprising a complex having one or more characteristics is described herein. In some aspects, a method of delivering a composition comprising the complex is described.

Compositions

In some embodiments, a composition of the invention includes a variant polypeptide that exhibits enhanced enzymatic activity, enhanced binding activity, enhanced binding specificity, and/or enhanced stability relative to a parent polypeptide. In some embodiments, a composition of the invention includes a complex comprising a variant polypeptide that exhibits enhanced enzymatic activity, enhanced binding activity, enhanced binding specificity, and/or enhanced stability relative to a parent complex.

In some embodiments, a composition of the invention includes a variant polypeptide and an RNA guide. In some embodiments, a composition of the invention includes a variant binary complex comprising a variant polypeptide and an RNA guide.

In some aspects of the composition, the variant polypeptide has increased complex formation (e.g., increased binary complex formation) with the RNA guide as compared to a parent polypeptide. In some aspects of the composition, the variant polypeptide and the RNA guide have a greater binding affinity, as compared to a parent polypeptide and the RNA guide. In some aspects of the composition, the variant polypeptide and the RNA guide have stronger protein-RNA interactions (e.g., ionic interactions), as compared to a parent polypeptide and the RNA guide. In some aspects of the composition, the variant binary complex is more stable than a parent binary complex.

In some embodiments, a composition of the invention includes a variant polypeptide, an RNA guide, and a target nucleic acid. In some embodiments, a composition of the invention includes a variant ternary complex comprising a variant polypeptide, an RNA guide, and a target nucleic acid.

In some aspects of the composition, the variant polypeptide has increased complex formation (e.g., increased ternary complex formation) with the RNA guide and target nucleic acid as compared to a parent polypeptide. In some aspects of the composition, the variant polypeptide and the RNA guide (e.g., the variant binary complex) have a greater binding affinity to a target nucleic acid, as compared to a parent polypeptide and the RNA guide (e.g., a parent binary complex). In some aspects of the composition, the variant ternary complex is more stable than a parent ternary complex.

In some embodiments, the composition of the present invention includes a variant polypeptide described herein.

Variant Polypeptides

In one embodiment, the variant polypeptide is an isolated or purified polypeptide.

In some embodiments, the variant polypeptide of the present invention is a variant of a parent polypeptide, wherein the parent is encoded by a polynucleotide that comprises a nucleotide sequence such as SEQ ID NO: 1 or SEQ ID NO: 2 or comprises an amino acid sequence such as SEQ ID NO: 3. See Table 1.

TABLE 1

Sequences corresponding to SEQ ID NOs: 1-3.

SEQ ID NO: 1

ATTGGTGATATCGCGAGCTTCCTGAAAGAAGCGACCAACAAGGATACCAT
CCCGACCTATATTAACATGGGCCTGAGCGAGGAATGGAAGTACAAACCGA
TTTATCACCTGTTCACCGACGATTACCACGAGAAGAGCGCGAACAACCTG
CTGTACGCGTATTTTAAGGAGAAAAACCTGGACTGCTATAACGGTAACAT
CCTGAACCTGAGCGAAACCTACTATCGTCGTAACGGTTACTTCAAAAGCG
TGGTTGGCAACTATCGTACCAAGATCCGTACCCTGAACTACAAGATTAAG
CGTAAGAACGTGGACGAGAACAGCACCAACGAGGATATCGAACTGCAGGT
TATGTATGAAATCGCGAAGCGTAAGCTGAACATTAAGAAAGACTGGGAGA
ACTACATCAGCTATATTGAGAACGTGGAAAACATCAACATCAAGAACATC
GATCGTTACAACCTGCTGTATAAGCACTTCTGCGAGAACGAAAGCACCAT
TAACTGCAAGATGGAACTGCTGAGCGTGGAGCAACTGAAAGAATTTGGTG
GCTGCGTTATGAAGCAGCACATCAACAGCATGACCATCAACATTCAAGAT
TTCAAAATCGAGAACAAGGAAAACAGCCTGGGTTTTATTCTGAACCTGCC
GCTGAACAAGAAAAGTACCAGATCGAGCTGTGGGGTAACCGTCAAATTA
AAAAGGGCAACAAAGATAACTACAAGACCCTGGTGGATTTCATCAACACC

TABLE 1-continued

Sequences corresponding to SEQ ID NOs: 1-3.

TATGGCCAGAACATCATCTTCACCATCAAGAACAACAAGATCTACGTGGT
TTTCAGCTATGAGTGCGAACTGAAGGAGAAGGAAATCAACTTCGACAAGA
TCGTGGGTATTGATGTTAACTTCAAGCACGCGCTGTTTGTTGCGAGCGAG
CGTGACAAAAACCCGCTGCAGGATAACAACCAACTGAAAGGCTACATCAA
CCTGTACAAGTATCTGCTGGAGCACAACGAGTTCACCAGCCTGCTGACCA
AAGAGGAGCTGGACATCTACAAAGAAATTGCGAAGGGTGTGACCTTCTGC
CCGCTGGAGTATAACCTGCTGTTTACCCGTATCGAAAACAAAGGTGGCAA
GAGCAACGATAAAGAGCAGGTTCTGAGCAAGCTGCTGTACAGCCTGCAAA
TTAAACTGAAGAACGAGAACAAAATCCAGGAATACATTTATGTGAGCTGC
GTTAACAAACTGCGTGCGAAGTACGTGAGCTATTTCATCCTGAAAGAGAA
GTACTATGAAAAACAAAAGGAGTACGACATTGAAATGGGCTTTACCGACG
ATAGCACCGAGAGCAAAGAAAGCATGGATAAGCGTCGTCTGGAGTTCCCG
TTTCGTAACACCCAGATCGCGAACGGTTTCCTGGAGAAGCTGAGCAACGT
TCAGCAAGACATTAACGGCTGCCTGAAAAACATCATTAACTACGCGTATA
AGGTGTTCGAACAAAACGGTTTTGCGTTATCGCGCTGGAGAACCTGGAA
AACAGCAACTTTGAGAAAACCCAAGTGCTGCCGACCATTAAAAGCCTGCT
GGAGTACCACAAGCTGGAAAACCAGAACATCAACAACATTAACGCGAGCG
ACAAAGTTAAGGAGTATATCGAGAAGGAATACTATGAACTGACCACCAAC
GAGAACAACGAAATTGTGGATGCGAAATACACCAAAAAGGGTATCATTAA
GGTTAAAAAGGCGAACTTCTTTAACCTGATGATGAAAAGCCTGCACTTCG
CGAGCAACAAGGACGAATTTATCCTGCTGAGCAACAACGGCA

SEQ ID NO: 2

ATGACCACAAAGCAGGTGAAGAGCATCGTGCTGAAGGTGAAGAACACCAA
TGAGTGCCCAATCACAAAGGACGTGATCAACGAGTACAAGAAGTACTATA
ATATCTGTTCCGAGTGGATCAAGGACAACCTGACCTCCATCACAATCGGC
GATATCGCCTCTTTCCTGAAGGAGGCCACCAATAAGGATACCATCCCCAC
ATATATCAACATGGGCCTGTCCGAGGAGTGGAAGTACAAGCCTATCTATC
ACCTGTTCACAGACGATTACCACGAGAAGTCTGCCAACAATCTGCTGTAC
GCCTACTTCAAGGAGAAGAACCTGGACTGCTATAACGGCAATATCCTGAA
TCTGTCCGAGACCTACTATCGGAGAAACGGCTACTTCAAGTCTGTGGTGG
GCAATTATCGGACCAAGATCAGAACACTGAACTACAAGATCAAGAGGAAG
AATGTGGACGAGAACTCTACAAATGAGGATATCGAGCTGCAGGTCATGTA
TGAGATCGCCAAGCGCAAGCTGAACATCAAGAAGGACTGGGAGAATTACA
TCAGCTATATCGAGAACGTGGAGAACATCAATATCAAGAACATCGATAGG
TACAATCTGCTGTATAAGCACTTCTGCGAGAACGAGAGCACCATCAATTG
TAAGATGGAGCTGCTGTCCGTGGAGCAGCTGAAGGAGTTTGGCGGCTGCG
TGATGAAGCAGCACATCAACTCTATGACAATCAATATCCAGGATTTCAAG
ATCGAGAACAAGGAGAATAGCCTGGGCTTTATCCTGAACCTGCCCCTGAA
CAAGAAGAAGTACCAGATCGAGCTGTGGGGCAACCGGCAGATCAAGAAGG
GCAACAAGGACAATTACAAGACCCTGGTGGATTTCATCAACACATATGGC
CAGAACATCATCTTTACCATCAAGAACAATAAGATCTACGTGGTGTTCTC
CTATGAGTGTGAGCTGAAGGAGAAGGAGATCAACTTTGACAAGATCGTGG
GCATCGATGTGAATTTCAAGCACGCCCTGTTTGTGGCCTCTGAGAGAGAC
AAGAACCCACTGCAGGATAACAATCAGCTGAAGGGCTACATCAACCTGTA
CAAGTATCTGCTGGAGCACAATGAGTTCACCAGCCTGCTGACAAAGGAGG
AGCTGGACATCTACAAGGAGATCGCCAAGGGCGTGACCTTCTGCCCCCTG
GAGTATAACCTGCTGTTTACAAGGATCGAGAACAAGGGCGGCAAGTCCAA
TGATAAGGAGCAGGTGCTGAGCAAGCTGCTGTACTCCCTGCAGATCAAGC
TGAAGAACGAGAATAAGATCCAGGAGTACATCTACGTGAGCTGCGTGAAT
AAGCTGCGCGCCAAGTACGTGAGCTATTTCATCCTGAAGGAGAAGTACTA
TGAGAAGCAGAAGGAGTACGACATCGAGATGGGCTTTACCGACGATAGCA
CAGAGTCCAAGGAGTCTATGGATAAGAGGCGCCTGGAGTTCCCTTTTCGG
AACACCCAGATCGCCAATGGCTTCCTGGAGAAGCTGAGCAACGTGCAGCA
GGACATCAATGGCTGTCTGAAGAACATCATCAATTACGCCTATAAGGTGT
TCGAGCAGAACGGCTTTGCCGTGATCGCCCTGGAGAATCTGGAGAACAGC
AATTTTGAGAAGACCCAGGTGCTGCCAACAATCAAGTCCCTGCTGGAGTA
CCACAAGCTGGAGAACCAGAATATCAACAATATCAACGCCTCTGACAAGG
TGAAGGAGTATATCGAGAAGGAGTACTATGAGCTGACCACAAATGAGAAC
AATGAGATCGTGGATGCCAAGTACACCAAGAAGGGCATCATCAAGGTGAA
GAAGGCCAACTTCTTTAATCTGATGATGAAGTCTCTGCACTTCGCCAGCA
ACAAGGACGAGTTTATCCTGCTGTCCAACAATGGCAAGACCCAGATCGCC
CTGGTGCCCAGCGAGTACATCCCAGATGGATTCTATCGAGCACTGCCT
GTATGTGGACAAGACGGCAAGAAGGTGGATAAGAAGGAAAGGTGCGGCAGA
AGCAGGAGACCCACATCAACGGCCTGAATGCCGACTTCAATGCCGCCAAC
AATATCAAGTACATCATCGAGAACGAGAATCTGAGAAAGCTGTTTTGTGG
CAAGCTGAAGGTGTCCGGCTATAACACCCCTATCCTGGATGCCACAAAGA
AGGGCCAGTTCAACATCCTGGCCGAGCTGAAGAAGCAGAATAAGATCAAG
ATCTTTGAGATCGAGAAG

SEQ ID NO: 3

MTTKQVKSIVLKVKNTNECPITKDVINEYKKYYNICSEWIKDNLTSITIG
DIASFLKEATNKDTIPTYINMGLSEEWKYKPIYHLFTDDYHEKSANNLLY
AYFKEKNLDCYNGNILNLSETYYRRNGYFKSVVGNYRTKIRTLNYKIKRK
NVDENSTNEDIELQVMYEIAKRKLNIKKDWENYISYIENVENINIKNIDR
YNLLYKHFCENESTINCKMELLSVEQLKEFGGCVMKQHINSMTINIQDFK

TABLE 1-continued

Sequences corresponding to SEQ ID NOs: 1-3.

IENKENSLGFILNLPLNKKKYQIELWGNRQIKKGNKDNYKTLVDFINTYG
QNIIFTIKNNKIYVVFSYECELKEKEINFDKIVGIDVNFKHALFVASERD
KNPLQDNNQLKGYINLYKYLLEHNEFTSLLTKEELDIYKEIAKGVTFCPL
EYNLLFTRIENKGGKSNDKEQVLSKLLYSLQIKLKNENKIQEYIYVSCVN
KLRAKYVSYFILKEKYYEKQKEYDIEMGFTDDSTESKESMDKRRLEFPFR
NTQIANGFLEKLSNVQQDINGCLKNIINYAYKVFEQNGFGVIALENLENS
NFEKTQVLPTIKSLLEYHKLENQNINNINASDKVKEYIEKEYYELTTNEN
NEIVDAKYTKKGIIKVKKANFFNLMMKSLHFASNKDEFILLSNNGKTQIA
LVPSEYTSQMDSIEHCLYVDKNGKKVDKKKVRQKQETHINGLNADFNAAN
NIKYIIENENLRKLFCGKLKVSGYNTPILDATKKGQFNILAELKKQNKIK
IFEIEK

A nucleic acid sequence encoding the parent polypeptide described herein may be substantially identical to a reference nucleic acid sequence, e.g., SEQ ID NO: 1 or SEQ ID NO: 2. In some embodiments, the variant polypeptide is encoded by a nucleic acid comprising a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the reference nucleic acid sequence, e.g., nucleic acid sequence encoding the parent polypeptide, e.g., SEQ ID NO: 1 or SEQ ID NO: 2. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the nucleic acid molecules hybridize to the complementary sequence of the other under stringent conditions (e.g., within a range of medium to high stringency).

In some embodiments, the variant polypeptide is encoded by a nucleic acid sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more sequence identity, but not 100% sequence identity, to a reference nucleic acid sequence, e.g., nucleic acid sequence encoding the parent polypeptide, e.g., SEQ ID NO: 1 or SEQ ID NO: 2.

In some embodiments, the variant polypeptide of the present invention comprises a polypeptide sequence having 50%, 60%, 65%, 70%, 75%, 80%, 85%, 90%, 91%, 92%, 93%, 94%, 95%, 96%, 97%, 98%, or 99%, but not 100%, identity to SEQ ID NO: 3. In some embodiments, the variant polypeptide of the present invention comprises a polypeptide sequence having greater than 50%, 60%, 65%, 70%, 75%, 80%, 85%, 90%, 91%, 92%, 93%, 94%, 95%, 96%, 97%, 98%, or 99%, but not 100%, identity to SEQ ID NO: 3.

In some embodiments, the present invention describes a variant polypeptide having a specified degree of amino acid sequence identity to one or more reference polypeptides, e.g., a parent polypeptide, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 3. Homology or identity can be determined by amino acid sequence alignment, e.g., using a program such as BLAST, ALIGN, or CLUSTAL, as described herein. In some embodiments, the variant polypeptide maintains the amino acid changes (or at least 1, 2, 3, 4, 5 etc. of these changes) that differentiate the polypeptide from its respective parent/reference sequence.

In some embodiments, the variant polypeptide comprises an alteration at one or more (e.g., several) amino acids of a parent polypeptide, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 162, 164, 164, 165, 166, 167, 168, 169, 170, 171, 172, 173, 174, 175, 176, 177, 178, 179, 180, 181, 182, 183, 184, 185, 186, 187, 188, 189, 190, 191, 193, 194, 195, 196, 197, 198, 199, 200, or more are altered.

In some embodiments, the variant polypeptide comprises one or more of the amino acid substitutions listed in Table 2.

TABLE 2

Single Amino Acid Substitutions in Variants of SEQ ID NO: 3.
Table 2

| Position | Wild-Type Residue | Substitutions |
| --- | --- | --- |
| 1 | M | |
| 2 | T | R, G, A, K, Q, N, H |
| 3 | T | R, G, A, K, Q, N, H |
| 4 | K | R, G, A, Q, N, H |
| 5 | Q | R, G, A, K, N, H |
| 6 | V | R, G, A, K, Q, N, H |
| 7 | K | R, G, A, Q, N, H |
| 8 | S | R, G, A, K, Q, N, H |
| 9 | I | R, G, A, K, Q, N, H |
| 10 | V | R, G, A, K, Q, N, H |
| 11 | L | R, G, A, K, Q, N, H |
| 12 | K | R, G, A, Q, N, H |
| 13 | V | R, G, A, K, Q, N, H |
| 14 | K | R, G, A, Q, N, H |
| 15 | N | R, G, A, K, Q, H |
| 16 | T | R, G, A, K, Q, N, H |
| 17 | N | R, G, A, K, Q, H |
| 18 | E | R, G, A, K, Q, N, H |
| 19 | C | R, G, A, K, Q, N, H |
| 20 | P | R, G, A, K, Q, N, H |
| 21 | I | R, G, A, K, Q, N, H |
| 22 | T | R, G, A, K, Q, N, H |
| 23 | K | R, G, A, Q, N, H |
| 24 | D | R, G, A, K, Q, N, H |
| 25 | V | R, G, A, K, Q, N, H |
| 26 | I | R, G, A, K, Q, N, H |
| 27 | N | R, G, A, K, Q, H |
| 28 | E | R, G, A, K, Q, N, H |
| 29 | Y | R, G, A, K, Q, N, H |
| 30 | K | R, G, A, Q, N, H |
| 31 | K | R, G, A, Q, N, H |
| 32 | Y | R, G, A, K, Q, N, H |
| 33 | Y | R, G, A, K, Q, N, H |
| 34 | N | R, G, A, K, Q, H |
| 35 | I | R, G, A, K, Q, N, H |
| 36 | C | R, G, A, K, Q, N, H |
| 37 | S | R, G, A, K, Q, N, H |
| 38 | E | R, G, A, K, Q, N, H |
| 39 | W | R, G, A, K, Q, N, H |
| 40 | I | R, G, A, K, Q, N, H |

TABLE 2-continued

Single Amino Acid Substitutions in Variants of SEQ ID NO: 3.

| Position | Wild-Type Residue | Substitutions |
|---|---|---|
|

TABLE 2-continued

Single Amino Acid Substitutions in Variants of SEQ ID NO: 3.
Table 2

| Position | Wild-Type Residue | Substitutions |
|---|---|---|
| 189 | N | R, G, A, K, Q, H |
| 190 | V | R, G, A, K, Q, N, H |
| 191 | E | R, G, A, K, Q, N, H |
| 192 | N | R, G, A, K, Q, H |
| 193 | I | R, G, A, K, Q, N, H |
| 194 | N | R, G, A, K, Q, H |
| 195 | I | R, G, A, K, Q, N, H |
| 196 | K | R, G, A, Q, N, H |
| 197 | N | R, G, A, K, Q, H |
| 198 | I | R, G, A, K, Q, N, H |
| 199 | D | R, G, A, K, Q, N, H |
| 200 | R | G, A, K, Q, N, H |
| 201 | Y | R, G, A, K, Q, N, H |
| 202 | N | R, G, A, K, Q, H |
| 203 | L | R, G, A, K, Q, N, H |
| 204 | L | R, G, A, K, Q, N, H |
| 205 | Y | R, G, A, K, Q, N, H |
| 206 | K | R, G, A, Q, N, H |
| 207 | H | R, G, A, K, Q, N |
| 208 | F | R, G, A, K, Q, N, H |
| 209 | C | R, G, A, K, Q, N, H |
| 210 | E | R, G, A, K, Q, N, H |
| 211 | N | R, G, A, K, Q, H |
| 212 | E | R, G, A, K, Q, N, H |
| 213 | S | R, G, A, K, Q, N, H |
| 214 | T | R, G, A, K, Q, N, H |
| 215 | I | R, G, A, K, Q, N, H |
|

TABLE 2-continued

Single Amino Acid Substitutions in Variants of SEQ ID NO: 3. Table 2

| Position | Wild-Type Residue | Substitutions |
|---|---|---|
| | | K, L, M, N, P, Q, R, S, T, V, W, Y |
| 337 | V | R, G, A, K, Q, N, H |
| 338 | N | R, G, A, K, Q, H |
| 339 | F | R, G, A, K, Q, N, H |
| 340 | K | R, G, A, Q, N, H |
| 341 | H | R, G, A, K, Q, N |
| 342 | A | R, G, K, Q, N, H |
| 343 | L | R, G, A, K, Q, N, H |
| 344 | F | R, G, A, K, Q, N, H |
| 345 | V | R, G, A, K, Q, N, H |
| 346 | A | R, G, K, Q, N, H |
| 347 | S | R, G, A, K, Q, N, H |
| 348 | E | R, G, A, K, Q, N, H |
| 349 | R | G, A, K, Q, N, H |
| 350 | D | R, G, A, K, Q, N, H |
| 351 | K | R, G, A, Q, N, H |
| 352 | N | R, G, A, K, Q, H |
| 353 | P | R, G, A, K, Q, N, H |
| 354 | L | R, G, A, K, Q, N, H |
| 355 | Q | R, G, A, K, N, H |
| 356 | D | R, G, A, K, Q, N, H |
| 357 | N | R, G, A, K, Q, H |
| 358 | N | R, G, A, K, Q, H |
| 359 | Q | R, G, A, K, N, H |
| 360 | L | R, G, A, K, Q, N, H |
| 361 | K | R, G, A, Q, N, H |
| 362 | G | R, A, K, Q, N, H |
| 363 | Y | R, G, A, K, Q, N, H |
| 364 | I | R, G, A, K, Q, N, H |
| 365 | N | R, G, A, K, Q, H |
| 366 | L | R, G, A, K, Q, N, H |
| 367 | Y | R, G, A, K, Q, N, H |
| 368 | K | R, G, A, Q, N, H |
| 369 | Y | R, G, A, K, Q, N, H |
| 370 | L | R, G, A, K, Q, N, H |
| 371 | L | R, G, A, K, Q, N, H |
| 372 | E | R, G, A, K, Q, N, H |
| 373 | H | R, G, A, K, Q, N |
| 374 | N | R, G, A, K, Q, H |
| 375 | E | R, G, A, K, Q, N, H |
| 376 | F | R, G, A, K, Q, N, H |
| 377 | T | R, G, A, K, Q, N, H |
| 378 | S | R, G, A, K, Q, N, H |
| 379 | L | R, G, A, K, Q, N, H |
| 380 | L | R, G, A, K, Q, N, H |
| 381 | T | R, G, A, K, Q, N, H |
| 382 | K | R, G, A, Q, N, H |
| 383 | E | R, G, A, K, Q, N, H |
| 384 | E | R, G, A, K, Q, N, H |
| 385 | L | R, G, A, K, Q, N, H |
| 386 | D | R, G, A, K, Q, N, H |
| 387 | I | R, G, A, K, Q, N, H |
| 388 | Y | R, G, A, K, Q, N, H |
| 389 | K | R, G, A, Q, N, H |
| 390 | E | R, G, A, K, Q, N, H |
| 391 | I | R, G, A, K, Q, N, H |
| 392 | A | R, G, K, Q, N, H |
| 393 | K | R, G, A, Q, N, H |
| 394 | G | R, A, K, Q, N, H |
| 395 | V | R, G, A, K, Q, N, H |
| 396 | T | R, G, A, K, Q, N, H |
| 397 | F | R, G, A, K, Q, N, H |
| 398 | C | R, G, A, K, Q, N, H |
| 399 | P | R, G, A, K, Q, N, H |
| 400 | L | R, G, A, K, Q, N, H |
| 401 | E | R, G, A, K, Q, N, H |
| 402 | Y | R, G, A, K, Q, N, H |
| 403 | N | R, G, A, K, Q, H |
| 404 | L | R, G, A, K, Q, N, H |
| 405 | L | R, G, A, K, Q, N, H |
| 406 | F | R, G, A, K, Q, N, H |
| 407 | T | R, G, A, K, Q, N, H |
| 408 | R | G, A, K, Q, N, H |
| 409 | I | R, G, A, K, Q, N, H |
| 410 | E | R, G, A, K, Q, N, H |
| 411 | N | R, G, A, K, Q, H |
| 412 | K | R, G, A, Q, N, H |
| 413 | G | R, A, K, Q, N, H |
| 414 | G | R, A, K, Q, N, H |
| 415 | K | R, G, A, Q, N, H |
| 416 | S | R, G, A, K, Q, N, H |
| 417 | N | R, G, A, K, Q, H |
| 418 | D | R, G, A, K, Q, N, H |
| 419 | K | R, G, A, Q, N, H |
| 420 | E | R, G, A, K, Q, N, H |
| 421 | Q | R, G, A, K, N, H |
| 422 | V | R, G, A, K, Q, N, H |
| 423 | L | R, G, A, K, Q, N, H |
| 424 | S | R, G, A, K, Q, N, H |
| 425 | K | R, G, A, Q, N, H |
| 426 | L | R, G, A, K, Q, N, H |
| 427 | L | R, G, A, K, Q, N, H |
| 428 | Y | R, G, A, K, Q, N, H |
| 429 | S | R, G, A, K, Q, N, H |
| 430 | L | R, G, A, K, Q, N, H |
| 431 | Q | R, G, A, K, N, H |
| 432 | I | R, G, A, K, Q, N, H |
| 433 | K | R, G, A, Q, N, H |
| 434 | L | R, G, A, K, Q, N, H |
| 435 | K | R, G, A, Q, N, H |
| 436 | N | R, G, A, K, Q, H |
| 437 | E | R, G, A, K, Q, N, H |
| 438 | N | R, G, A, K, Q, H |
| 439 | K | R, G, A, Q, N, H |
| 440 | I | R, G, A, K, Q, N, H |
| 441 | Q | R, G, A, K, N, H |
| 442 | E | R, G, A, K, Q, N, H |
| 443 | Y | R, G, A, K, Q, N, H |
| 444 | I | R, G, A, K, Q, N, H |
| 445 | Y | R, G, A, K, Q, N, H |
| 446 | V | R, G, A, K, Q, N, H |
| 447 | S | R, G, A, K, Q, N, H |
| 448 | C | R, G, A, K, Q, N, H |
| 449 | V | R, G, A, K, Q, N, H |
| 450 | N | R, G, A, K, Q, H |
| 451 | K | R, G, A, Q, N, H |
| 452 | L | R, G, A, K, Q, N, H |
| 453 | R | G, A, K, Q, N, H |
| 454 | A | R, G, K, Q, N, H |
| 455 | K | R, G, A, Q, N, H |
| 456 | Y | R, G, A, K, Q, N, H |
| 457 | V | R, G, A, K, Q, N, H |
| 458 | S | R, G, A, K, Q, N, H |
| 459 | Y | R, G, A, K, Q, N, H |
| 460 | F | R, G, A, K, Q, N, H |
| 461 | I | R, G, A, K, Q, N, H |
| 462 | L | R, G, A, K, Q, N, H |
| 463 | K | R, G, A, Q, N, H |
| 464 | E | R, G, A, K, Q, N, H |
| 465 | K | R, G, A, Q, N, H |
| 466 | Y | R, G, A, K, Q, N, H |
| 467 | Y | R, G, A, K, Q, N, H |
| 468 | E | R, G, A, K, Q, N, H |
| 469 | K | R, G, A, Q, N, H |
| 470 | Q | R, G, A, K, N, H |
| 471 | K | R, G, A, Q, N, H |
| 472 | E | R, G, A, K, Q, N, H |
| 473 | Y | R, G, A, K, Q, N, H |
| 474 | D | R, G, A, K, Q, N, H |
| 475 | I | R, G, A, K, Q, N, H |
| 476 | E | R, G, A, K, Q, N, H |
| 477 | M | R, G, A, K, Q, N, H |
| 478 | G | R, A, K, Q, N, H |
| 479 | F | R, G, A, K, Q, N, H |
| 480 | T | R, G, A, K, Q, N, H |
| 481 | D | R, G, A, K, Q, N, H |
| 482 | D | R, G, A, K, Q, N, H |

TABLE 2-continued

Single Amino Acid Substitutions in Variants of SEQ ID NO: 3.
Table 2

| Position | Wild-Type Residue | Substitutions |
|---|---|---|
| 483 | S | R, G, A, K,

TABLE 2-continued

Single Amino Acid Substitutions in Variants of SEQ ID NO: 3.
Table 2

| Position | Wild-Type Residue | Substitutions |
|---|---|---|
| 629 | L | R, G, A, K, Q, N, H |
| 630 | H | R, G, A, K, Q, N |
| 631 | F | R, G, A, K, Q, N, H |
| 632 | A | R, G, K, Q, N, H |
| 633 | S | R, G, A, K, Q, N, H |
| 634 | N | R, G, A, K, Q, H |
| 635 | K | R, G, A, Q, N, H |
| 636 | D | R, G, A, K, Q, N, H |
| 637 | E | R, G, A, K, Q, N, H |
| 638 | F | R, G, A, K, Q, N, H |
| 639 | I | R, G, A, K, Q, N, H |
| 640 | L | R, G, A, K, Q, N, H |
| 641 | L | R, G, A, K, Q, N, H |
| 642 | S | R, G, A, K, Q, N, H |
| 643 | N | R, G, A, K, Q, H |
| 644 | N | R, G, A, K, Q, H |
| 645 | G | R, A, K, Q, N, H |
| 646 | K | R, G, A, Q, N, H |
| 647 | T | R, G, A, K, Q, N, H |
| 648 | Q | R, G, A, K, N, H |
| 649 | I | R, G, A, K, Q, N, H |
| 650 | A | R, G, K, Q, N, H |
| 651 | L | R, G, A, K, Q, N, H |
| 652 | V | R, G, A, K, Q, N, H |
| 653 | P | R, G, A, K, Q, N, H |
| 654 | S | R, G, A, K, Q, N, H |
| 655 | E | R, G, A, K, Q, N, H |
| 656 | Y | R, G, A, K, Q, N, H |
| 657 | T | R, G, A, K, Q, N, H |
| 658 | S | R, G, A, K, Q, N, H |
| 659 | Q | R, G, A, K, N, H |
| 660 | N | R, G, A, K, Q, H |
| 661 | D | R, G, A, K, Q, N, H |
| 662 | S | R, G, A, K, Q, N, H |
| 663 | I | R, G, A, K, Q, N, H |
| 664 | E | R, G, A, K, Q, N, H |
| 665 | H | R, G, A, K, Q, N |
| 666 | C | R, G, A, K, Q, N, H |
| 667 | L | R, G, A, K, Q, N, H |
| 668 | Y | R, G, A, K, Q, N, H |
| 669 | V | R, G, A, K, Q, N, H |
| 670 | D | R, G, A, K, Q, N, H |
| 671 | K | R, G, A, Q, N, H |
| 672 | N | R, G, A, K, Q, H |
| 673 | G | R, A, K, Q, N, H |
| 674 | K | R, G, A, Q, N, H |
| 675 | K | R, G, A, Q, N, H |
| 676 | V | R, G, A, K, Q, N, H |
| 677 | D | R, G, A, K, Q, N, H |
| 678 | K | R, G, A, K, Q, N, H |
| 679 | K | R, G, A, K, Q, N, H |
| 680 | K | R, G, A, K, Q, N, H |
| 681 | V | R, G, A, K, Q, N, H |
| 682 | R | G, A, K, Q, N, H |
| 683 | Q | R, G, A, K, N, H |
| 684 | K | R, G, A, Q, N, H |
| 685 | Q | R, G, A, K, N, H |
| 686 | E | R, G, A, K, Q, N, H |
| 687 | T | R, G, A, K, Q, N, H |
| 688 | H | R, G, A, K, Q, N |
| 689 | I | R, G, A, K, Q, N, H |
| 690 | N | R, G, A, K, Q, H |
| 691 | G | R, A, K, Q, N, H |
| 692 | L | R, G, A, K, Q, N, H |
| 693 | N | R, G, A, K, Q, H |
| 694 | A | R, G, K, Q, N, H |
| 695 | D | R, G, A, K, Q, N, H |
| 696 | F | R, G, A, K, Q, N, H |
| 697 | N | R, G, A, K, Q, H |
| 698 | A | R, G, K, Q, N, H |
| 699 | A | R, G, K, Q, N, H |
| 700 | N | R, G, A, K, Q, H |
| 701 | N | R, G, A, K, Q, H |
| 702 | I | R, G, A, K, Q, N, H |
| 703 | K | R, G, A, Q, N, H |
| 704 | Y | R, G, A, K, Q, N, H |
| 705 | I | R, G, A, K, Q, N, H |
| 706 | I | R, G, A, K, Q, N, H |
| 707 | E | R, G, A, K, Q, N, H |
| 708 | N | R, G, A, K, Q, H |
| 709 | E | R, G, A, K, Q, N, H |
| 710 | N | R, G, A, K, Q, H |
| 711 | L | R, G, A, K, Q, N, H |
| 712 | R | G, A, K, Q, N, H |
| 713 | K | R, G, A, Q, N, H |
| 714 | L | R, G, A, K, Q, N, H |
| 715 | F | R, G, A, K, Q, N, H |
| 716 | C | R, G, A, K, Q, N, H |
| 717 | G | R, A, K, Q, N, H |
| 718 | K | R, G, A, Q, N, H |
| 719 | L | R, G, A, K, Q, N, H |
| 720 | K | R, G, A, Q, N, H |
| 721 | V | R, G, A, K, Q, N, H |
| 722 | S | R, G, A, K, Q, N, H |
| 723 | G | R, A, K, Q, N, H |
| 724 | Y | R, G, A, K, Q, N, H |
| 725 | N | R, G, A, K, Q, H |
| 726 | T | R, G, A, K, Q, N, H |
| 727 | P | R, G, A, K, Q, N, H |
| 728 | I | R, G, A, K, Q, N, H |
| 729 | L | R, G, A, K, Q, N, H |
| 730 | D | R, G, A, K, Q, N, H |
| 731 | A | R, G, K, Q, N, H |
| 732 | T | R, G, A, K, Q, N, H |
| 733 | K | R, G, A, Q, N, H |
| 734 | K | R, G, A, Q, N, H |
| 735 | G | R, A, K, Q, N, H |
| 736 | Q | R, G, A, K, N, H |
| 737 | F | R, G, A, K, Q, N, H |
| 738 | N | R, G, A, K, Q, H |
| 739 | I | R, G, A, K, Q, N, H |
| 740 | L | R, G, A, K, Q, N, H |
| 741 | A | R, G, K, Q, N, H |
| 742 | E | R, G, A, K, Q, N, H |
| 743 | L | R, G, A, K, Q, N, H |
| 744 | K | R, G, A, Q, N, H |
| 745 | K | R, G, A, Q, N, H |
| 746 | Q | R, G, A, K, N, H |
| 747 | N | R, G, A, K, Q, H |
| 748 | K | R, G, A, Q, N, H |
| 749 | I | R, G, A, K, Q, N, H |
| 750 | K | R, G, A, Q, N, H |
| 751 | I | R, G, A, K, Q, N, H |
| 752 | F | R, G, A, K, Q, N, H |
| 753 | E | R, G, A, K, Q, N, H |
| 754 | I | R, G, A, K, Q, N, H |
| 755 | E | R, G, A, K, Q, N, H |
| 756 | K | R, G, A, Q, N, H |

In some embodiments, the variant polypeptide comprises an alteration that increases interactions of the variant polypeptide to the RNA guide. In some embodiments, the alteration that increases interactions with the RNA guide is an arginine, lysine, glutamine, asparagine, or histidine substitution. In some embodiments, the variant polypeptide comprises an alteration that increases interactions of the variant polypeptide to the target nucleic acid. In some embodiments, the alteration that increases interactions with the target nucleic acid is an arginine, lysine, glutamine, asparagine, or histidine substitution. In some embodiments, the variant polypeptide comprises an alanine substitution. In some embodiments, the variant polypeptide comprises a glycine substitution.

In some embodiments, the variant polypeptide comprises one or more substitutions from P353 through L360. For example, in some embodiments, the variant polypeptide comprises one or more of the following substitutions: P353G, L354G, Q355G, D356G, N357G, N358G, Q359G, and L360G. In some embodiments, the variant comprises one or more N-terminal arginine substitutions.

In some embodiments, the variant polypeptide comprises: a substitution at E38, a substitution at T60, a substitution at D89, a substitution at S223, a substitution at P353, a substitution at L354, a substitution at L360, a substitution at K368, a substitution at E566, and/or a substitution at D730. In some embodiments, the substitution at E38 is an E38R substitution, the substitution at T60 is a T60R substitution, the substitution at D89 is a D89R substitution, the substitution at S223 is an S223R substitution, the substitution at P353 is a P353G substitution, the substitution at L354 is an L354G substitution, the substitution at L360 is an L360G substitution, the substitution at K368 is a K368G substitution, the substitution at E566 is an E566R substitution, and/or the substitution at D730 is a D730R substitution. In some embodiments, the variant polypeptide is a double mutant, triple mutant, quadruple mutant, or quintuple mutant comprising a substitution at E38, a substitution at T60, a substitution at D89, a substitution at S223, a substitution at P353, a substitution at L354, a substitution at L360, a substitution at K368, a substitution at E566, and/or a substitution at D730. In some embodiments, the variant polypeptide is a double mutant, triple mutant, quadruple mutant, or quintuple mutant comprising an E38R substitution, a T60R substitution, a D89R substitution, an S223R substitution, a P353G substitution, an L354G substitution, an L360G substitution, a K368G substitution, an E566R substitution, and/or a D730R substitution.

In some embodiments, the variant polypeptide comprises a D89R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 14. In some embodiments, the variant polypeptide comprises an amino acid sequence having at least 95% (e.g., 95%, 96%, 97%, 98%, 99%, or 100%) identity to SEQ ID NO: 14. In some embodiments, the variant polypeptide comprises the amino acid sequence set forth in SEQ ID NO: 14.

In some embodiments, the variant polypeptide comprises an L354G substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 15. In some embodiments, the variant polypeptide comprises an amino acid sequence having at least 95% (e.g., 95%, 96%, 97%, 98%, 99%, or 100%) identity to SEQ ID NO: 15. In some embodiments, the variant polypeptide comprises the amino acid sequence set forth in SEQ ID NO: 15.

In some embodiments, the variant polypeptide comprises an K368G substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 16. In some embodiments, the variant polypeptide comprises an amino acid sequence having at least 95% (e.g., 95%, 96%, 97%, 98%, 99%, or 100%) identity to SEQ ID NO: 16. In some embodiments, the variant polypeptide comprises the amino acid sequence set forth in SEQ ID NO: 16.

In some embodiments, the variant polypeptide comprises an E566R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 17. In some embodiments, the variant polypeptide comprises an amino acid sequence having at least 95% (e.g., 95%, 96%, 97%, 98%, 99%, or 100%) identity to SEQ ID NO: 17. In some embodiments, the variant polypeptide comprises the amino acid sequence set forth in SEQ ID NO: 17.

In some embodiments, the variant polypeptide comprises an D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 18. In some embodiments, the variant polypeptide comprises an amino acid sequence having at least 95% (e.g., 95%, 96%, 97%, 98%, 99%, or 100%) identity to SEQ ID NO: 18. In some embodiments, the variant polypeptide comprises the amino acid sequence set forth in SEQ ID NO: 18.

In some embodiments, the variant polypeptide comprises a D89R substitution and an L354G substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 19. In some embodiments, the variant polypeptide comprises an amino acid sequence having at least 95% (e.g., 95%, 96%, 97%, 98%, 99%, or 100%) identity to SEQ ID NO: 19. In some embodiments, the variant polypeptide comprises the amino acid sequence set forth in SEQ ID NO: 19.

In some embodiments, the variant polypeptide comprises a D89R substitution and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 20. In some embodiments, the variant polypeptide comprises an amino acid sequence having at least 95% (e.g., 95%, 96%, 97%, 98%, 99%, or 100%) identity to SEQ ID NO: 20. In some embodiments, the variant polypeptide comprises the amino acid sequence set forth in SEQ ID NO: 20.

In some embodiments, the variant polypeptide comprises an L354G substitution and a K386G substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 21. In some embodiments, the variant polypeptide comprises an amino acid sequence having at least 95% (e.g., 95%, 96%, 97%, 98%, 99%, or 100%) identity to SEQ ID NO: 21. In some embodiments, the variant polypeptide comprises the amino acid sequence set forth in SEQ ID NO: 21.

In some embodiments, the variant polypeptide comprises an L345G substitution and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 22. In some embodiments, the variant polypeptide comprises an amino acid sequence having at least 95% (e.g., 95%, 96%, 97%, 98%, 99%, or 100%) identity to SEQ ID NO: 22. In some embodiments, the variant polypeptide comprises the amino acid sequence set forth in SEQ ID NO: 22.

In some embodiments, the variant polypeptide comprises a K368G substitution and an E566R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 23. In some embodiments, the variant polypeptide comprises an amino acid sequence having at least 95% (e.g., 95%, 96%, 97%, 98%, 99%, or 100%) identity to SEQ ID NO: 23. In some embodiments, the variant polypeptide comprises the amino acid sequence set forth in SEQ ID NO: 23.

In some embodiments, the variant polypeptide comprises a K368G substitution and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 24. In some embodiments, the variant polypeptide comprises an amino acid sequence having at least 95% (e.g., 95%, 96%, 97%, 98%, 99%, or 100%) identity to SEQ ID NO: 24. In some embodiments, the variant polypeptide comprises the amino acid sequence set forth in SEQ ID NO: 24.

In some embodiments, the variant polypeptide comprises an E566R substitution and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 25. In some embodiments, the variant polypeptide comprises an amino acid sequence having at least 95% (e.g., 95%, 96%, 97%, 98%, 99%, or 100%) identity to SEQ ID NO: 25. In some embodiments, the variant polypeptide comprises the amino acid sequence set forth in SEQ ID NO: 25.

In some embodiments, the variant polypeptide comprises a D89R substitution, an L354G substation, and a K368G substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 26. In some embodiments, the variant polypeptide comprises an amino acid sequence having at least 95% (e.g., 95%, 96%, 97%, 98%, 99%, or 100%) identity to SEQ ID NO: 26. In some embodiments, the variant polypeptide comprises the amino acid sequence set forth in SEQ ID NO: 26.

In some embodiments, the variant polypeptide comprises a D89R substitution, an L354G substitution, and an E566R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 27. In some embodiments, the variant polypeptide comprises an amino acid sequence having at least 95% (e.g., 95%, 96%, 97%, 98%, 99%, or 100%) identity to SEQ ID NO: 27. In some embodiments, the variant polypeptide comprises the amino acid sequence set forth in SEQ ID NO: 27.

In some embodiments, the variant polypeptide comprises a D89R substitution, an L354G substitution, and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 28. In some embodiments, the variant polypeptide comprises an amino acid sequence having at least 95% (e.g., 95%, 96%, 97%, 98%, 99%, or 100%) identity to SEQ ID NO: 28. In some embodiments, the variant polypeptide comprises the amino acid sequence set forth in SEQ ID NO: 28.

In some embodiments, the variant polypeptide comprises a D89R substitution, a K368G substitution, and an E566R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 29. In some embodiments, the variant polypeptide comprises an amino acid sequence having at least 95% (e.g., 95%, 96%, 97%, 98%, 99%, or 100%) identity to SEQ ID NO: 29. In some embodiments, the variant polypeptide comprises the amino acid sequence set forth in SEQ ID NO: 29.

In some embodiments, the variant polypeptide comprises a D89R substitution, a K368G substitution, and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 30. In some embodiments, the variant polypeptide comprises an amino acid sequence having at least 95% (e.g., 95%, 96%, 97%, 98%, 99%, or 100%) identity to SEQ ID NO: 30. In some embodiments, the variant polypeptide comprises the amino acid sequence set forth in SEQ ID NO: 30.

In some embodiments, the variant polypeptide comprises a D89R substitution, an E566R substitution, and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 31. In some embodiments, the variant polypeptide comprises an amino acid sequence having at least 95% (e.g., 95%, 96%, 97%, 98%, 99%, or 100%) identity to SEQ ID NO: 31. In some embodiments, the variant polypeptide comprises the amino acid sequence set forth in SEQ ID NO: 31.

In some embodiments, the variant polypeptide comprises an L354G substitution, a K368G substitution, and an E566R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 32. In some embodiments, the variant polypeptide comprises an amino acid sequence having at least 95% (e.g., 95%, 96%, 97%, 98%, 99%, or 100%) identity to SEQ ID NO: 32. In some embodiments, the variant polypeptide comprises the amino acid sequence set forth in SEQ ID NO: 32.

In some embodiments, the variant polypeptide comprises an L354G substitution, a K368G substitution, and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 33. In some embodiments, the variant polypeptide comprises an amino acid sequence having at least 95% (e.g., 95%, 96%, 97%, 98%, 99%, or 100%) identity to SEQ ID NO: 33. In some embodiments, the variant polypeptide comprises the amino acid sequence set forth in SEQ ID NO: 33.

In some embodiments, the variant polypeptide comprises an L354G substitution, an E566R substitution, and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 34. In some embodiments, the variant polypeptide comprises an amino acid sequence having at least 95% (e.g., 95%, 96%, 97%, 98%, 99%, or 100%) identity to SEQ ID NO: 34. In some embodiments, the variant polypeptide comprises the amino acid sequence set forth in SEQ ID NO: 34.

In some embodiments, the variant polypeptide comprises an L354G substitution, an E566R substitution, and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 35. In some embodiments, the variant polypeptide comprises an amino acid sequence having at least 95% (e.g., 95%, 96%, 97%, 98%, 99%, or 100%) identity to SEQ ID NO: 35. In some embodiments, the variant polypeptide comprises the amino acid sequence set forth in SEQ ID NO: 35.

In some embodiments, the variant polypeptide comprises a D89R substitution, an L354G substitution, a K368G substitution, and an E566R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 36. In some embodiments, the variant polypeptide comprises an amino acid sequence having at least 95% (e.g., 95%, 96%, 97%, 98%, 99%, or 100%) identity to SEQ ID NO: 36. In some embodiments, the variant polypeptide comprises the amino acid sequence set forth in SEQ ID NO: 36.

In some embodiments, the variant polypeptide comprises a D89R substitution, an L354G substitution, a K368G substitution, and an D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 37. In some embodiments, the variant polypeptide comprises an amino acid sequence having at least 95% (e.g., 95%, 96%, 97%, 98%, 99%, or 100%) identity to SEQ ID NO: 37. In some embodiments, the variant polypeptide comprises the amino acid sequence set forth in SEQ ID NO: 37.

In some embodiments, the variant polypeptide comprises a D89R substitution, an L354G substitution, an E566R substitution, and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 38. In some embodiments, the variant polypeptide comprises an amino acid sequence having at least 95% (e.g., 95%, 96%, 97%, 98%, 99%, or 100%) identity to SEQ ID NO: 38. In some embodiments, the variant polypeptide comprises the amino acid sequence set forth in SEQ ID NO: 38.

In some embodiments, the variant polypeptide comprises a D89R substitution, a K368G substitution, an E566R substitution, and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 39. In some embodiments, the variant polypeptide comprises an amino acid sequence having at least 95% (e.g., 95%, 96%, 97%, 98%, 99%, or 100%) identity to SEQ ID NO: 39. In some embodiments, the variant polypeptide comprises the amino acid sequence set forth in SEQ ID NO: 39.

In some embodiments, the variant polypeptide comprises an L354G substitution, a K368G substitution, an E566R substitution, and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 40. In some embodiments, the variant polypeptide comprises an amino acid sequence having at least 95% (e.g., 95%, 96%, 97%, 98%, 99%, or 100%) identity to SEQ ID NO: 40. In some embodiments, the variant polypeptide comprises the amino acid sequence set forth in SEQ ID NO: 40.

In some embodiments, the variant polypeptide comprises a D89R substitution, an L354G substitution, a K368G substitution, an E566R substitution, and a D730R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 41. In some embodiments, the variant polypeptide comprises an amino acid sequence having at least 95% (e.g., 95%, 96%, 97%, 98%, 99%, or 100%) identity to SEQ ID NO: 41. In some embodiments, the variant polypeptide comprises the amino acid sequence set forth in SEQ ID NO: 41.

In some embodiments, the variant polypeptide comprises a D89R substitution, a K368G substitution, an E566R substitution, a D730R substitution, a T60R substitution, and a D356G substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 49. In some embodiments, the variant polypeptide comprises an amino acid sequence having at least 95% (e.g., 95%, 96%, 97%, 98%, 99%, or 100%) identity to SEQ ID NO: 49. In some embodiments, the variant polypeptide comprises the amino acid sequence set forth in SEQ ID NO: 49.

In some embodiments, the variant polypeptide comprises a D89R substitution, a K368G substitution, an E566R substitution, a D730R substitution, a T60R substitution, a D356G substitution, and a P353G substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 50. In some embodiments, the variant polypeptide comprises an amino acid sequence having at least 95% (e.g., 95%, 96%, 97%, 98%, 99%, or 100%) identity to SEQ ID NO: 50. In some embodiments, the variant polypeptide comprises the amino acid sequence set forth in SEQ ID NO: 50.

In some embodiments, the variant polypeptide comprises a D89R substitution, a K368G substitution, an E566R substitution, a D730R substitution, a T60R substitution, a D356G substitution, and a E571R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 51. In some embodiments, the variant polypeptide comprises an amino acid sequence having at least 95% (e.g., 95%, 96%, 97%, 98%, 99%, or 100%) identity to SEQ ID NO: 51. In some embodiments, the variant polypeptide comprises the amino acid sequence set forth in SEQ ID NO: 51.

In some embodiments, the variant polypeptide comprises a D89R substitution, a K368G substitution, an E566R substitution, a D730R substitution, a T60R substitution, a D356G substitution, a P353G substitution, and a E571R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 52. In some embodiments, the variant polypeptide comprises an amino acid sequence having at least 95% (e.g., 95%, 96%, 97%, 98%, 99%, or 100%) identity to SEQ ID NO: 52. In some embodiments, the variant polypeptide comprises the amino acid sequence set forth in SEQ ID NO: 52.

In some embodiments, the variant polypeptide comprises a D89R substitution, L354G an E566R substitution, a D730R substitution, and a T60R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 53. In some embodiments, the variant polypeptide comprises an amino acid sequence having at least 95% (e.g., 95%, 96%, 97%, 98%, 99%, or 100%) identity to SEQ ID NO: 53. In some embodiments, the variant polypeptide comprises the amino acid sequence set forth in SEQ ID NO: 53.

In some embodiments, the variant polypeptide comprises a D89R substitution, L354G an E566R substitution, a D730R substitution, and a D356G substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 54. In some embodiments, the variant polypeptide comprises an amino acid sequence having at least 95% (e.g., 95%, 96%, 97%, 98%, 99%, or 100%) identity to SEQ ID NO: 54. In some embodiments, the variant polypeptide comprises the amino acid sequence set forth in SEQ ID NO: 54.

In some embodiments, the variant polypeptide comprises a D89R substitution, L354G an E566R substitution, a D730R substitution, a T60R substitution, and a D356G substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 55. In some embodiments, the variant polypeptide comprises an amino acid sequence having at least 95% (e.g., 95%, 96%, 97%, 98%, 99%, or 100%) identity to SEQ ID NO: 55. In some embodiments, the variant polypeptide comprises the amino acid sequence set forth in SEQ ID NO: 55.

In some embodiments, the variant polypeptide comprises a D89R substitution, L354G an E566R substitution, a D730R substitution, a T60R substitution, and a P353G substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 56. In some embodiments, the variant polypeptide comprises an amino acid sequence having at least 95% (e.g., 95%, 96%, 97%, 98%, 99%, or 100%) identity to SEQ ID NO: 56. In some embodiments, the variant polypeptide comprises the amino acid sequence set forth in SEQ ID NO: 56.

In some embodiments, the variant polypeptide comprises a D89R substitution, L354G an E566R substitution, a D730R substitution, a T60R substitution, and a E571R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 57. In some embodiments, the variant polypeptide comprises an amino acid sequence having at least 95% (e.g., 95%, 96%, 97%, 98%, 99%, or 100%) identity to SEQ ID NO: 57. In some embodiments, the variant polypeptide comprises the amino acid sequence set forth in SEQ ID NO: 57.

In some embodiments, the variant polypeptide comprises a D89R substitution, L354G an E566R substitution, a D730R substitution, a T60R substitution, a P353G substitution, a D356G substitution, and a E571R substitution relative to SEQ ID NO: 3. In some embodiments, the variant polypeptide comprises an amino acid sequence having at least 90% (e.g., 90%, 91%, 92%, 93%, 94%, 95%, 96%, 97%, 98%, 99%, or 100%) identity to SEQ ID NO: 58. In some embodiments, the variant polypeptide comprises an amino acid sequence having at least 95% (e.g., 95%, 96%, 97%, 98%, 99%, or 100%) identity to SEQ ID NO: 58. In some embodiments, the variant polypeptide comprises the amino acid sequence set forth in SEQ ID NO: 58.

In some embodiments, the variant polypeptide comprises one or more of the following mutations relative to SEQ ID NO: 3: Q683K, E586G, Q556R, D356G, Q421R, Q556K, N579K, N501K, D482K, S722K, Q359G, V557R, N620R, E589K, T480K, L523K, E571R, E571K, E566K, L523R, and E319R. In some embodiments, a variant polypeptide of any one of SEQ ID NOs: 14-41 or 49-48 further comprises one or more of the following mutations: Q683K, E586G, Q556R, D356G, Q421R, Q556K, N579K, N501K, D482K, S722K, Q359G, V557R, N620R, E589K, T480K, L523K, E571R, E571K, E566K, L523R, and E319R.

In some embodiments, the variant polypeptide comprises at least one RuvC motif or a RuvC domain.

Although the changes described herein may be one or more amino acid changes, changes to the variant polypeptide may also be of a substantive nature, such as fusion of polypeptides as amino- and/or carboxyl-terminal extensions. For example, variant polypeptide may contain additional peptides, e.g., one or more peptides. Examples of additional peptides may include epitope peptides for labelling, such as a polyhistidine tag (His-tag), Myc, and FLAG. In some embodiments, the variant polypeptide described herein can be fused to a detectable moiety such as a fluorescent protein (e.g., green fluorescent protein (GFP) or yellow fluorescent protein (YFP)).

In some embodiments, the variant polypeptide comprises at least one (e.g., two, three, four, five, six, or more) nuclear localization signal (NLS). In some embodiments, the variant polypeptide comprises at least one (e.g., two, three, four, five, six, or more) nuclear export signal (NES). In some embodiments, the variant polypeptide comprises at least one (e.g., two, three, four, five, six, or more) NLS and at least one (e.g., two, three, four, five, six, or more) NES.

In some embodiments, the variant polypeptide described herein can be self-inactivating. See, Epstein et al., "Engineering a Self-Inactivating CRISPR System for AAV Vectors," Mol. Ther., 24 (2016): S50, which is incorporated by reference in its entirety.

In some embodiments, the nucleotide sequence encoding the variant polypeptide described herein can be codon-optimized for use in a particular host cell or organism. For example, the nucleic acid can be codon-optimized for any non-human eukaryote including mice, rats, rabbits, dogs, livestock, or non-human primates. Codon usage tables are readily available, for example, at the "Codon Usage Database" available at www.kazusa.orjp/codon/and these tables can be adapted in a number of ways. See Nakamura et al. Nucl. Acids Res. 28:292 (2000), which is incorporated herein by reference in its entirety. Computer algorithms for codon optimizing a particular sequence for expression in a particular host cell are also available, such as Gene Forge (Aptagen; Jacobus, PA).

Nucleotide sequences encoding the variant polypeptide of SEQ ID NO: 39 are shown in Table 3. In some embodiments, the nucleotides sequences of any one of SEQ ID NOs: 59-66 can be modified to encode a variant polypeptide comprising a D89R substitution, a K368G substitution, an E566R substitution a D730R substitution, and one or more additional substitutions described herein relative to SEQ ID NO: 3.

TABLE 3

Sequences corresponding to SEQ ID NOs: 59-66.

SEQ ID NO: 59

```
ATGACTACCAAGCAAGTCAAATCCATAGTACTGAAGGTTAAGAATACAAATGAATGCCCAATCACCAAG
GATGTGATCAACGAGTACAAGAAGTATTATAATATCTGTAGCGAGTGGATTAAAGATAATCTGACCTCT
ATAACCATCGGCGACATCGCCTCTTTTTTGAAAGAAGCAACAAACAAAGATACTATCCCAACGTACATC
AATATGGGACTTAGTGAAGAGTGGAAATACAAGCCTATCTACCATCTCTTTACCGACAGATACCACGAG
AAATCAGCCAACAACCTGCTTTATGCTTACTTTAAGGAAAAGAATCTGGATTGTTATAATGGCAATATC
CTCAACTTGTCCGAGACATACTACCGTCGCAATGGATACTTCAAGTCGGTAGTGGGGAACTATCGTACA
AAAATTCGCACACTTAACTATAAGATTAAGAGAAAAAACGTTGACGAGAATAGCACCAATGAAGATATT
GAACTCCAAGTTATGTATGAAATCGCAAAGCGCAAGCTGAACATTAAGAAGGACTGGGAGAATTATATC
TCATACATTGAGAATGTCGAGAACATCAACATCAAAAATATCGATCGGTACAACCTGCTATACAAGCAT
TTCTGTGAAAATGAGTCCACCATCAACTGCAAGATGGAGTTGCTCTCTGTGGAACAGCTCAAAGAGTTC
GGGGGTTGTGTGATGAAGCAGCACATAAATTCCATGACGATAAACATACAGGACTTTAAGATTGAAAAC
AAGGAGAACTCACTGGGTTTCATCCTGAACCTGCCCTTGAACAAGAAAAAGTACCAGATAGAACTGTGG
GGGAACCGACAAATCAAAAAAGGGAATAAGGATAACTATAAGACGCTGGTTGACTTTATCAACACTTAT
GGTCAGAACATTATTTTCACCATTAAAAATAATAAAATTTACGTCGTGTTCAGCTACGAGTGTGAATTA
AAGGAGAAGGAAATCAATTTCGACAAGATTGTCGGGATTGATGTGAATTTCAAGCACGCCCTGTTTGTG
GCTTCCGAGCGGGACAAAAACCCACTGCAAGATAATAACCAGCTAAAAGGGTACATAAACCTGTATGGC
TATCTTCTGGAGCATAATGAATTTACAAGCCTGCTGACCAAGGAGGAACTGGACATTTATAAAGAAATT
GCGAAGGGCGTCACATTTTGTCCCCTGGAGTACAACTTGCTTTTCACTAGAATAGAGAATAAGGGCGGA
AAGTCTAACGACAAAGAACAGGTGCTGAGCAAGCTGCTCTATAGCTTGCAGATCAAACTCAAAAATGAA
AATAAGATTCAGGAGTATATCTATGTGAGTTGCGTAAATAAGCTCCGAGCCAAATACGTGTCATACTTT
ATCTTGAAAGAAAAATACTACGAAAAGCAGAAAGAGTACGACATCGAGATGGGCTTCACGGATGACTCG
ACTGAGTCTAAAGAGTCTATGGACAAGAGGCGGCTGGAGTTCCCCTTTAGGAATACTCAGATTGCTAAT
GGCTTCCTCGAAAAACTCTCCAACGTGCAGCAAGATATCAACGGATGCTTAAAGAATATTATTAACTAT
GCCTATAAAGTATTCGAGCAAAACGGATTTGGAGTCATCGCACTGGAAAACTTAGAGAACAGCAACTTC
GAAAAGACACAGGTCTTACCTACAATCAAGAGTCTACTTCGGTATCATAAGTTGGGAGAATCAGAATATT
AATAATATTAACGCGAGTGACAAGGTGAAAGAGTACATAGAGAAGGAGTATTACGAACTAACTACCAAC
GAGAACAATGAAATAGTCGATGCTAAATACACTAAAAAGGGAATTATCAAGGTGAAAAAAGCTAACTTT
TTTAACCTAATGATGAAATCCCTGCACTTTGCCAGTAACAAAGATGAGTTCATCTTGCTGAGCAATAAC
GGTAAAACACAAATTGCACTGGTTCCGAGCGAGTATACCTCCCAGATGGACTCTATAGAACACTGCCTC
TACGTGGACAAAAATGGGAAAAAAGTGGACAAAAAGAAGGTTAGGCAGAAGCAGGAAACTCACATCAAC
GGCCTCAACGCCGATTTCAACGCCGCTAACAATATAAAGTACATCATCGAAAACGAGAATCTTAGGAAG
CTGTTTTGCGGCAAGCTGAAGGTGTCAGGTTATAACACCCCTATCCTCAGAGCCACCAAAAAGGGCCAG
TTCAATATTCTGGCAGAGCTGAAGAAGCAGAATAAGATTAAAATCTTCGAGATTGAGAAA
```

SEQ ID NO: 60

```
ATGACCACCAAGCAAGTGAAGAGCATCGTGCTGAAGGTGAAGAACACCAACGAGTGCCCCATCACCAAG
GACGTGATCAACGAGTACAAGAAGTACTACAACATCTGCAGCGAGTGGATCAAGGACAACCTGACAAGC
ATCACCATCGGCGACATCGCTAGCTTCCTGAAGGAGGCCACCAACAAGGACACCATCCCCACCTACATC
AACATGGGCCTGAGCGAGGAGTGGAAGTACAAGCCCATCTACCACCTGTTCACCGACAGATACCACGAG
AAGAGCGCCAATAACCTGCTGTACGCCTATTTCAAGGAGAAGAACCTGGACTGCTACAACGGCAACATC
CTGAACCTGAGCGAGACCTACTACAGAAGAAACGGCTACTTCAAGAGCGTGGTGGGCAACTACAGAACC
AAGATCAGAACCCTGAACTATAAGATCAAGCGTAAAAACGTGGACGAGAACGACACCAACGAGGACATC
GAGCTGCAAGTGATGTACGAGATCGCCAAAAGAAAGCTGAACATCAAGAAGGACTGGGAGAACTACATC
AGCTACATCGAGAACGTGGAAAACATCAATATTAAGAACATCGACAGATATAACCTTTTGTACAAGCAT
TTCTGCGAGAACGAGAGCACCATCAACTGCAAGATGGAGCTGCTGAGCGTGGAGCAGCTGAAGGAGTTC
GGCGGCTGCGTGATGAAGCAGCACATCAACGCTAAGCATCCAAGACTTCAAGATCGAAAAC
AAAGAAAACAGCCTGGGCTTTATCCTCAACCTTCCACTGAACAAGAAGAAGTATCAGATCGAGCTGTGG
GGCAACAGACAGATCAAGAAGGGCAACAAGGACAACTATAAGACGTTAGTGGACTTCATCAACACCTAC
GGGCAGAACATCATCTTCACCATCAAGAACAACAAGATCTACGTGGTGTTCAGCTACGAGTGCGAGCTG
AAAGAGAAGGAAATCAACTTCGACAAGATCGTGGGCATCGACGTGAACTTCAAGCACGCGCCCTGTTCGTG
GCTAGCGAGAGAGACAAGAACCCCCTGCAAGACAACAATCAGCTGAAGGGCTACATCAACCTGTACGGC
TACCTGCTGGAGCACAACGAGTTCACAAGCCTGCTGACCAAGGAGGAGCTGGACATCTACAAGGAGATC
GCCAAGGGTGTCACCTTCTGCCCCCTGGAGTACAACCTTCTTTTCACAAGAATCGAGAACAAGGGCGGC
AAGAGCAACGACAAGGAGCAAGTGCTGAGCAAGCTGCTGTACAGCCTGCAGATCAAGCTGAAGAACGAG
AACAAGATCCAAGAGTACATCTACGTGAGCTGCGTGAACAAGCTGAGAGCCAAGTACGTGAGCTACTTC
ATCCTGAAGGAAAAGTACTACGAAGCAGAAGGAGTACGACATCGAGATGGGCTTCACCGACGACAGC
ACCGAGAGCAAGGAGAGCATGGACAAGAGAAGACTGGAGTTCCCCTTCAGAAACACACAGATCGCCAAC
GGGTTCCTGGAGAAGCTGAGCAACGTGCAGCAAGACATCAACGGCTGCCTGAAGAACATCATCAACTAC
GCCTACAAGGTGTTCGAGCAGAACGGCTTCGGCGTGATCGCCCTGGAGAACCTGGAGAACAGCAACTTC
GAGAAGACCCAAGTGCTGCCCACCATCAAGAGCCTGCTGAGATACCACAAGCTGGAGAACCAAAATATC
AATAATATCAATGCTAGCGACAAGGTGAAGGAGTACATCGAGAAGGAGTACTACGAGCTGACCACCAAC
GAGAACAACGAGATCGTGGACGCCAAGTACACTAAGAAGGGTATAATCAAGGTGAAGAAGGCCAACTTC
TTCAACCTGATGATGAAGAGCCTGCACTTCGCTAGCAACAAGGACGAGTTCATCCTGCTGAGCAACAAC
GGCAAGACAGATCGCACTGGTGCCTAGCGAGTACACATCTCAGATGGACAGCATCGAGCACTGCCTG
TACGTGGACAAGAACGGCAAGAAGGTGGACAAGAAGAAGGTGAGACAGAAGCAAGAGACCCACATCAAC
GGCCTGAACGCCGACTTCAACGCCGCCAACAACATCAAGTATATCATCGAGAACGAGAACCTGAGAAAG
CTGTTCTGCGGCAAGCTGAAGGTGAGCGGCTACAACACCCCCATCCTGAGAGCCACAAAGAAAGGGCAG
TTTAACATCCTGGCCGAGCTGAAGAAGCAGAACAAGATCAAGATCTTTGAGATCGAGAAG
```

TABLE 3-continued

Sequences corresponding to SEQ ID NOs: 59-66.

SEQ ID NO: 61

```
ATGACCACCAAGCAGGTGAAGAGCATCGTGCTGAAGGTGAAGAACACCAACGAGTGCCCCATCACCAAG
GACGTGATCAACGAGTACAAGAAGTACTACAACATCTGCAGCGAGTGGATCAAGGACAACCTGACCAGC
ATCACCATCGGCGACATCGCCAGCTTCCTGAAGGAGGCCACCAACAAGGACACCATCCCCACCTACATC
AACATGGGCCTGAGCGAGGAGTGGAAGTACAAGCCCATCTACCACCTGTTCACCGACCGGTACCACGAG
AAGAGCGCCAACAACCTGCTGTACGCCTACTTCAAGGAGAAGAACCTGGACTGCTACAACGGCAACATC
CTGAACCTGAGCGAGACCTACTACCGGCGGAACGGCTACTTCAAGAGCGTGGTGGGCAACTACCGGACC
AAGATCCGGACCCTGAACTACAAGATCAAGCGGAAGAACGTGGACGAGAACAGCACCAACGAGGACATC
GAGCTGCAGGTGATGTACGAGATCGCCAAGCGGAAGCTGAACATCAAGAAGGACTGGGAGAACTACATC
AGCTACATCGAGAACGTGGAGAACATCAACATCAAGAACATCGACCGGTACAACCTGCTGTACAAGCAC
TTCTGCGAGAACGAGAGCACCATCAACTGCAAGATGGAGCTGCTGAGCGTGGAGCAGCTGAAGGAGTTC
GGCGGCTGCGTGATGAAGCAGCACATCAACAGCATGACCATCAACATCCAGGACTTCAAGATCGAGAAC
AAGGAGAACAGCCTGGGCTTCATCCTGAACCTGCCCCTGAACAAGAAGAAGTACCAGATCGAGCTGTGG
GGCAACCGGCAGATCAAGAAGGGCAACAAGGACAACTACAAGACCCTGGTGGACTTCATCAACACCTAC
GGCCAGAACATCATCTTCACCATCAAGAACAACAAGATCTACGTGGTGTTCAGCTACGAGTGCGAGCTG
AAGGAGAAGGAGATCAACTTCGACAAGATCGTGGGCATCGACGTGAACTTCAAGCACGCCCTGTTCGTG
GCCAGCGAGCGGGACAAGAACCCCCTGCAGGACAACAACCAGCTGAAGGGCTACATCAACCTGTACGGC
TACCTGCTGGAGCACAACGAGTTCACCCAGCCTGCTGACCAAGGAGGAGCTGGACATCTACAAGGAGATC
GCCAAGGGCGTGACCTTCTGCCCCCTGGAGTACAACCTGCTGTTCACCCGGATCGAGAACAAGGGCGGC
AAGAGCAACGACAAGGAGCAGGTGCTGAGCAAGCTGCTGTACAGCCTGCAGATCAAGCTGAAGAACGAG
AACAAGATCCAGGAGTACATCTACGTGAGCTGCGTGAACAAGCTGCGGGCCAAGTACGTGAGCTACTTC
ATCCTGAAGGAGAAGTACTACGAGAAGCAGAAGGAGTACGACATCGAGATGGGCTTCACCGACGACAGC
ACCGAGAGCAAGGAGCATGGACAAGCGGCGGCTGGAGTTCCCCTTCCGGAACACCCAGATCGCCAAC
GGCTTCCTGGAGAAGCTGAGCAACGTGCAGCAGGACATCAACGGCTGCCTGAAGAACATCATCAACTAC
GCCTACAAGGTGTTCGAGCAGAACGGCTTCGGCGTGATCGCCCTGGAGAACCTGGAGAACGAGCAACTTC
GAGAAGACCCAGGTGCTGCCCACCATCAAGAGCCTGCTGCGGTACCACAAGCTGGAGAACCAGAACATC
AACAACATCAACGCCAGCGACAAGGTGAAGGAGTACATCGAGAAGGAGTACTACGAGCTGACCACCAAC
GAGAACAACGAGATCGTGGACGCCAAGTACACCAAGAAGGGCATCATCAAGGTGAAGAAGGCCAACTTC
TTCAACCTGATGATGAAGAGCCTGCACTTCGCCAGCAACAAGGACGAGTTCATCCTGCTGAGCAACAAC
GGCAAGACCCAGATCGCCCTGGTGCCCAGCGAGTACACCAGCCAGATGGACAGCATCGAGCACTGCCTG
TACGTGGACAAGAACGGCAAGAAGGTGGACAAGAAGAAGGTGCGGCAGAAGCAGGAGACCCACATCAAC
GGCCTGAACGCCGACTTCAACGCCGCCAACAACATCAAGTACATCATCGAGAACGAGAACCTGCGGAAG
CTGTTCTGCGGCAAGCTGAAGGTGAGCGGCTACAACACCCCATCCTGCGGGCCACCAAGAAGGGCCAG
TTCAACATCCTGGCCGAGCTGAAGAAGCAGAACAAGATCAAGATCTTCGAGATCGAGAAG
```

SEQ ID NO: 62

```
ATGACTACGAAACAAGTAAAGTCTATTGTGCTTAAAGTGAAGAATACTAACGAGTGTCCCATTACCAAG
GATGTTATAAATGAATACAAAAAATATTATAACATCTGCAGCGAATGGATAAAAGATAACCTTACTTCT
ATTACTATAGGGGATATAGCGTCCTTTCTGAAGGAGGCGACGAACAAAGACACTATCCCGACCTACATC
AACATGGGGCTCTCCGAAGAATGGAAGTACAAGCCCTATCTACCATCTTTTCACCGACAGATATCATGAG
AAATCCGCAAATAATTTGTTGTATGCTTACTTCAAAGAGAAGAACTTGGATTGCTACAACGGTAATATT
CTTAATCTCTCAGAGACTTATTACAGGAGGAACGGGTACTTTAAAAGCGTGGTCGGAAATTATCGCACA
AAAATACGCACATTGAATTATAAAATCAAGCGAAAAAACGTCGATGAAAACTCTACAAACGAGGATATT
GAGCTGCAAGTGATGTATGAAATCGCAAAGAGAAAACTGAACATCAAGAAGGATTGGGAGAATTACATA
TCCTATATCGAAAACGTGGAGAATATCAACATCAAGAACATAGATAGATAATCTGCTCTATAAGCAT
TTTTGCGAAAACGAGTCTACAATTAACTGCAAGATGGAGCTGCTTTCCGTAGAGCAACTTAAGGAATTT
GGTGGATGCGTTATGAAGCAGCATATCAACAGTATGACTATTAATATACAGGATTTTAAGATCGAGAAT
AAGGAAAACTCCCTGGGCTTTATTCTCAATCTGCCCCTGAACAAAAAAAAGTATCAGATAGAACTCTGG
GGCAATAGACAGATTAAGAAAGGTAATAAGGACAATTATAAAACCCTCGTAGACTTTATAAATACATAC
GGGCAAAACATCATTTTCACGATTAAGAATAACAAAATTTATGTTGTGTTCTCCTATGAGTGTGAACTG
AAGGAGAAAGAGATTAACTTCGATAAGATAGTTGGGATTGATGTGAACTTTAAACACGCCCTTTTCGTT
GCGTCCGAGAGGGACAAGAATCCCTTGCAGGATAATAATCAACTGAAGGGTTACATCAATCTCTATGGA
TACTTGCTGGAACACAACGAATTCACAAGTCTCCTGACGAAGGAGGAACTCGATATTTATAAGGAAATA
GCCAAAGGAGTTACCTTTTGTCCGCTCGAGTATAATCTTCTCTTCACACGGATCGAAAACAAAGGAGGA
AAGAGCAATGATAAAGAACAAGTACTTTCCAAACTTCTTTATAGTCTCCAAATTAAGCTGAAGAACGAG
AACAAGATCCAGGAGTATATATATGTGTCATGTGTGAATAAGCTGCGAGCGAAATACGTATCTTACTTC
ATTCTCAAAGAAAATATTATGAGAAGCAGAAAGAATACGATATTGAAATGGGCTTTACAGACGACTCA
ACCGAGTCCAAAGAGTCTATGGACAAAAGACGATTGGAGTTCCCGTTTCGAAATACACAGATCGCCAAT
GGTTTCCTCGAGAAGCTGAGTAATGTGCAGCAAGATATAAATGGCTGCCTTAAGAATATAATTAACTAC
GCTTACAAGGTGTTTGAACAAAATGGGTTCGGCGTTATCGCCCTCGAAAACCTTGAAAATTCTAACTTT
GAAAAGACGCAAGTCCTTCCTACAATTAAGTCCCTTCTTCGCTATCACAAACTGGAGAACCAAAATATC
AATAACATTAATGCTTCAGATAAAGTTAAGGAATACATAGAAAAAGGATCTACGAACTTACCACCAAC
GAAAACAATGAAATTGTAGACGCTAAGTACACAAAGAAGGGCATTATAAAAGTTAAAAAAGCGAACTTC
TTTAACTTGATGATGAAATCACTTCATTTTGCGTCAAACAAGACGAGTTTATCTTGCTCAGCAATAAT
GGTAAGACTCAAATCGCCCTCGTCCCTTCTGAGTATACAAGCCAGATGGATTCTATTGAGCACTGTCTC
TACGTGGATAAGAACGGAAAGAAAGTAGACAAGAAAAAGGTCAGGCAGAAACAAGAGACACACATCAAT
GGGCTGAATGCCGACTTTAATGCCGCAAACAACATAAAGTATATAATCGAGAACGAAAACCTCCGAAAG
CTGTTTTGCGGTAAACTGAAAGTGAGCGGGTACAATACACCTATCCTGCGCGCTACCAAAAAAGGCCAA
TTTAATATACTGGCTGAGCTCAAGAAGCAAAATAAAATCAAAATCTTTGAGATAGAGAAG
```

SEQ ID NO: 63

```
ATGACCACCAAGCAAGTGAAATCTATCGTGCTGAAGGTGAAGAACACCAACGAATGCCCTATCACCAAG
GATGTGATCAACGAGTACAAGAAGTATTATAACATCTGCAGCGAGTGGATCAAAGATAATTTGACAAGC
ATCACCATCGGCGACATCGCCTCCTTCCTGAAGGAAGCCACCAACAAGGATACAATACCCACCTACATC
```

TABLE 3-continued

Sequences corresponding to SEQ ID NOs: 59-66.

AACATGGGCCTGAGCGAGGAATGGAAATACAAGCCCATCTACCATCTGTTTACCGACCGCTACCACGAG
AAAAGCGCCAACAACCTGCTCTACGCTTATTTCAAGGAGAAGAACCTGGACTGCTACAATGGAAATATC
CTGAACCTGTCTGAGACATACTACAGAAGAAACGGCTATTTCAAGAGTGTGGTCGGAAACTACAGGACC
AAAATCCGGACCCTGAACTACAAGATCAAGCGGAAGAACGTGGACGAGAATTCTACCAACGAGGACATC
GAGCTGCAGGTGATGTACGAGATCGCTAAGCGGAAGCTGAATATCAAGAAAGACTGGGAGAACTACATC
AGCTACATCGAGAACGTGGAAAACATCAACATCAAGAATATCGATAGATACAATCTGCTGTACAAGCAC
TTCTGCGAGAACGAGAGCACCATCAACTGCAAGATGGAACTCCTGAGCGTGGAACAGCTGAAAGAGTTC
GGCGGCTGTGTGATGAAACAACACATCAATAGCATGACCATCAACATTCAGGACTTCAAGATCGAGAAC
AAGGAAAATAGCTTGGGCTTCATCCTGAACCTGCCTCTGAACAAGAAGAAGTACCAGATCGAGCTCTGG
GGCAACAGACAGATCAAGAAAGGCAATAAGGATAACTACAAAACCCTGGTCGATTTCATCAACACATAC
GGGCAGAACATAATCTTTACAATCAAGAACAACAAAATCTACGTGGTGTTCAGCTACGAATGTGAACTG
AAGGAAAAAGAAATCAACTTCGACAAGATTGTGGGCATCGACGTGAACTTTAAGCACGCCCTGTTCGTG
GCCTCTGAAAGAGATAAGAATCCTCTGCAAGACAACAATCAACTGAAGGGCTACATCAACCTCTACGGC
TACCTGCTGGAGCACAACGAGTTCACATCTCTGCTGACCAAGGAAGAACTGGATATCTATAAGGAGATT
GCCAAGGGTGTTACATTCTGCCCACTGGAATACAACCTGCTGTTCACCAGATCGAGAACAAGGGCGGA
AAGTCCAACGACAAGGAGCAGGTGCTGTCTAAGCTGCTGTACAGCCTGCAGATCAAGCTGAAGAATGAA
AACAAGATCCAGGAGTACATCTACGTGAGCTGCGTGAACAAGCTGCGGGCCAAATACGTGTCCTACTTC
ATCCTGAAGGAAAAATACTACGAGAAGCAGAAGGAATACGACATCGAGATGGGATTTACAGACGACAGC
ACCGAGAGCAAGGAAAAGCATGGACAAACGGAGACTGGAATTCCCCTTCAGAAACACCCAGATCGCCAAC
GGCTTCCTGGAAAAGCTGAGCAACGTGCAGCAGGACATCAACGGCTGTCTGAAAAACATCATTAACTAC
GCCTACAAAGTCTTCGAGCAGAACGGCTTTGGCGTGATAGCTCTGGAAAACCTGGAAAACAGCAACTTC
GAGAAGACCCAGGTGCTGCCTACCATCAAGAGCCTGCTGCGGTACCACAAGCTCGAGAACCAGAATATT
AACAACATTAATGCCAGCGACAAGGTGAAGGAGTATATTGAGAAGGAATACTACGAGCTGACAACCAAC
GAGAACAACGAAATCGTGGACGCCAAGTACACCAAGAAGGGCATCATCAAGGTGAAGAAGGCCAATTTT
TTCAACCTGATGATGAAGTCTCTGCACTTCGCCTCTAATAAAGATGAGTTCATCCTGCTGTCCAACAAT
GGCAAAACCCAGATCGCTCTGGTGCCTAGCGAGTATACTAGCCAGATGGATAGCATCGAGCACTGTCTG
TACGTGGACAAGAACGGCAAGAAGGTGGACAAGAAGAAAGTTGACAGAAACAGGAGACCCACATCAAC
GGACTTAACGCCGACTTTAACGCCGCTAACAACATAAAGTACATCATCGAGAATGAGAACCCTTAGAAAG
CTGTTTTGCGGCAAGCTGAAAGTCTCCGGCTACAACACCCCTATCCTGAGAGCCACAAAGAAAGGACAG
TTCAACATCCTGGCCGAGCTGAAGAAACAGAACAAGATCAAGATCTTCGAGATCGAGAAG

SEQ ID NO: 64

ATGACCACTAAGCAAGTGAAATCCATCGTCTTGAAAGTAAAGAATACCAATGAGTGCCCTATTACAAAG
GACGTTATCAATGAGTATAAAAAATACTACAACATCTGTTCTGAATGGATTAAAGACAACCTCACGAGC
ATCACTATAGGAGATATCGCATCCTTCCTGAAGGAGGCAACCAACAAGGATACCATCCCTACATATATA
AACATGGGGCTTTCAGAGGAGTGGAAATACAAGCCCATTTATCACCTTTTCACAGATAGATACCACGAA
AAAAGTGCAAATAACTTGCTTTACGCTTACTTTAAAGAGAAAAACTTGGACTGTTACAATGGTAACATT
CTGAACCTGTCCGAGACATACTACAGACGGAACGGCTACTTCAAATCAGTCGTCGGGAATTATAGGACC
AAGATCCGGACCTTGAACTACAAAATTAAAAGAAAAAATGTTGATGAGAATAGCACAAACGAAGACATT
TCCTACATTGAGAATGTGGAAAATATCAACATTAAGAATATAGACCGCTACAACCTGCTGTATAAACAC
TTCTGCGAGAATGAAAGCACTATAAATTGCAAGATGGAGCTGCTGTCAGTGGAGCAGTTGAAAGAATTT
GGAGGGTGTGTGATGAAGCAACATATCAATAGTATGACAATTAACATACAGGACTTCAAGATTGAAAAC
AAGGAGAATTCCCTGGGATTCATCCTCAATCTGCCATTGAATAAAAAGAAATACCAAATAGAATTGTGG
GGAAACCGACAGATCAAGAAGGGAAATAAGGACAACTATAAGACCCTGGTCGACTTTATCAACACATAT
GGCCAGAACATTATTTTCACTATAAAAACAACAAGATCTACGTGGTATTCAGCTACGAGTGCGAGCTG
AAAGAGAAAGAAATTAATTTTGACAAAATTGTAGGAATCGATGTGAACTTCAAACACGCCCTGTTCGTC
GCCAGCGAAAGAGACAAGAATCCGCTGCAGGATAACAATCAGCTGAAGGGCTACATCAATCTCTATGGT
TATCTCCTGGAGCACAATGAATTCACAAGTCTGCTGACCAAAGAGGAATTGGATATCTACAAGGAAATC
GCCAAGGGGGTCACCTTTTGTCCACTGGAGTACAACCTGCTGTTCACGCGCATCGAGAATAAAGGCGGG
AAAAGTAATGATAAAGAACAAGTACTGAGTAAGCTGTTGTATAGCCTGCAGATTAAGCTCAAGAATGAA
AACAAGATCCAGGAGTACATTTACGTGAGCTGCGTCAATAAGCTGAGGGCTAAGTACGTGCTCATATTT
ATTCTCAAAGAAAAGTATTATGAGAAACAGAAAGAGTACGACATCGAGATGGGATTTACAGACGATTCT
ACCGAAAGCAAGGAATCAATGGACAAGCGCCGCTTGGAGTTTCCTTTCAGAAACACTCAGATCGCCAAT
GGATTCCTGGAAAAGCTGAGTAACGTGCAACAGGACATCAATGGTTGTCTCAAGAACATTATTAACTAC
GCATACAAGGTGTTTGAACAGAACGGGTTCGGTGTGATTGCTCTTGAAAATCTGGAAAATAGCAACTTC
GAAAAGACACAGGTCCTCCCAACAATTAAATCACTGCTCAGATATCACAAGCTCGAAAACCAGAACATC
AATAATATCAACGCCTCCGATAAAGTGAAAGAGTACATTGAAAAGGAGTACTACGAGCTGACAACCAAC
GAAAACAATGAAATTGTGGATGCTAAGTACACCAAAAAAGGGAATTATCAAGGTGAAGAAAGCTAATTTT
TTCAACCTGATGATGAAGAGCCTGCATTTCGCTTCCAATAAGGATGAATTTATTCTTCTGTCAAACAAT
GGAAAGACCCAGATCGCCCTCGTGCCAAGTGAGTATACATCACAGATGGACTCTATTGAGCATTGTCTC
TATGTGGATAAGAACGGAAAGAAGGTCGATAAGAAGAAAGTGCGACAGAAACAAGAGACGCATATCAAT
GGCCTCAATGCTGATTTTAATGCCGCAAACAATATAAAATATATCATTGAAAACGAGAATTTGCGCAAG
CTGTTTTGCGGGAAGCTGAAAGTTTCTGGGTATAATACCCCTATCTTGCGCGCCACTAAGAAGGGACAA
TTTAATATCCTGGCTGAGCTGAAGAAACAAAATAAAATCAAATATTCGAGATCGAGAAG

SEQ ID NO: 65

ATGACCACCAAGCAGGTGAAATCAATTGTGCTGAAGGTGAAGAATACCAATGAGTGCCCCATCACAAAG
GACGTGATCAACGAGTACAAGAAGTACTATAATATCTGTAGCGAGTGGATCAAGGACAATCTGACATCC
ATCACTATCGGCGACATCGCCTCCTTCCTGAAGGAGGCCACCAACAAGGACACAATCCCTACTTACATC
AACATGGGACTGTCCGAGGAATGGAAGTACAAGCCAATCTACCACCTGTTTACCGATAGGTACCACGAG
AAATCCGCCAATAACCTGCTGTACGCATATTTCAAGGAAAAGAATCTGGACTGCTATAACGGCAACATC
CTGAACCTGTCCGAGACGTACTACCGGCGCAACGGATACTTCAAGAGCGTGGTGGGCAACTACCGCACC
AAGATCAGAACCCTGAATTACAAGATTAAGAGAAAAAACGTGGACGAAAATAGCACCAACGAGGATATC
GAGCTGCAGGTGATGTACGAGATCGCCAAACGGAAACTGAATATCAAGAAAGATTGGGAGAACTATATC
AGTTATATTGAGAATGTGGAGAATATCAACATCAAAAACATTGACAGATACAACCTGCTCTACAAACAC
TTTTGTGAAAACGAGTCTACCATCAATTGTAAGATGGAGCTGCTGTCCGTGGAACAGCTGAAGGAGTTT

TABLE 3-continued

Sequences corresponding to SEQ ID NOs: 59-66.

```
GGCGGCTGTGTGATGAAGCAGCATATCAACTCCATGACCATCAATATCCAGGACTTCAAGATCGAGAAT
AAGGAGAATAGCCTGGGGTTTATCCTGAACCTGCCTCTGAACAAGAAGAAGTATCAGATCGAGCTGTGG
GGAAACCGCCAGATCAAGAAGGGCAACAAAGATAACTATAAGACCCTGGTGGACTTCATCAACACATAC
GGGCAGAATATCATCTTCACCATTAAGAACAACAAGATCTATGTGGTGTTTAGTTACGAGTGCGAGCTG
AAGGAGAAGGAGATTAATTTCGACAAGATCGTGGGAATTGACGTGAATTTCAAGCACGCTCTGTTCGTG
GCTTCAGAGAGAGACAAGAATCCACTGCAGGACAACAACCAGCTGAAGGGTTACATTAACCTTTACGGC
TACCTGCTGGAGCACAATGAGTTTACCAGCCTGCTGACTAAGGAGGAGCTGGACATATACAAGGAAATC
GCCAAGGGCGTGACGTTCTGCCCACTGGAGTATAACCTGCTCTTTACACGGATCGAGAATAAAGGCGGG
AAAAGCAATGACAAGGAGCAGGTGCTGTCTAAACTGCTGTATTCACTGCAGATCAAGCTGAAAAACGAG
AACAAGATCCAGGAATACATTTACGTGAGCTGCGTGAACAAACTGAGGGCCAAGTATGTGTCATATTTC
ATCCTGAAGGAGAAGTACTATGAGAAGCAGAAGGAGTACGACATCGAAGATGGGATTTACTGACGACTCC
ACCGAGAGCAAGGAGAGCATGGATAAGAGAAGACTGGAGTTCCCATTCCGCAACACCCAGATCGCCAAC
GGCTTTCTGGAAAAACTGAGTAACGTGCAGCAGGACATTAATGGATGTCTGAAGAATATCATCAACTAC
GCTTACAAGGTGTTTGAGCAGAACGGATTTGGCGTTATCGCCCTGGAAAACCTGGAAAACTCCAACTTT
GAGAAGACACAGGTGCTGCCAACCATCAAGAGCCTGCTGAGGTACCACAAGCTGGAGAATCAGAACATT
AACAATATCAACGCTAGCGACAAAGTGAAGGAGTACATTGAGAAAGAATACTACGAGCTGACCACCAAT
GAAAACAACGAGATCGTGGACGCCAAGTATACCAAGAAAGGCATCATCAAGGTCAAAAAGGCTAATTTC
TTCAATCTGATGATGAAAAGCCTGCACTTTGCCTCCAATAAAGACGAGTTTATTCTCCTGAGTAATAAC
GGCAAGACCCAGATCGCCCTGGTGCCATCAGAGTATACCAGCCAGATGGATTCAATTGAGCACTGTCTG
TACGTGGACAAGAATGGCAAGAAAGTGGACAAGAAGAAAGTTCGACAGAAGCAGGAAACCCACATCAAT
GGACTCAATGCAGATTTCAATGCCGCCAACAATATCAAGTACATTATCGAGAACGAGAACCTCCGGAAG
CTGTTTTGCGGCAAGCTGAAGGTGTCCGGGTACAATACCCCCATCCTGCGCGCCACCAAGAAGGGGCAG
TTCAACATCCTGGCCGAACTGAAAAAGCAGAACAAGATCAAGATCTTTGAGATCGAGAAG
```

SEQ ID NO: 66

```
ATGACCACAAAGCAGGTGAAGAGCATCGTGCTGAAGGTGAAGAACACCAATGAGTGCCCAATCACAAAG
GACGTGATCAACGAGTACAAGAAGTACTATAATATCTGTTCCGAGTGGATCAAGGACAACCTGACCTCC
ATCACAATCGGCGATATCGCCTCTTTCCTGAAGGAGGCCACCAATAAGGATACCATCCCCACATATATC
AACATGGGCCTGTCCGAGGAGTGGAAGTACAAGCCTATCTATCACCTGTTCACAGACCGTTACCACGAG
AAGTCTGCCAACAATCTGCTGTACGCCTACTTCAAGGAGAAGAACCTGGACTGCTATAACGGCAATATC
CTGAATCTGTCCGAGACCTACTATCGGAGAAACGGCTACTTCAAGTCTGTGGTGGGCAATTATCGGACC
AAGATCAGAACACTGAACTACAAGATCAAGAGGAAGAATGTGGACGAGAACTCTACAAATGAGGATATC
GAGCTGCAGGTCATGTATGAGATCGCCAAGCGCAAGCTGAACATCAAGAAGGACTGGGAGAATTACATC
AGCTATATCGAGAACGTGGAGAACATCAATATCAAGAACATCGATAGGTACAATCTGCTGTATAAGCAC
TTCTGCGAGAACGAGAGCACCATCAATTGTAAGATGGAGCTGTCTGTCCGTGGAGCAGCTGAAGGAGTTT
GGCGGCTGCGTGATGAAGCAGCACATCAACTCTATGACAATCAATATCCAGGATTTCAAGATCGAGAAC
AAGGAGAATAGCCTGGCTTTATCCTGAACCTGCCCCTGAACAAGAAGAAGTACCAGATCGAGCTGTGG
GGCAACCGGCAGATCAAGAAGGGCAACAAGGACAATTACAAGACCCTGGTGGATTTCATCAACACATAT
GGCCAGAACATCATCTTTACCATCAAGAACAATAAGATCTACGTGGTGTTCTCCTATGAGTGTGAGCTG
AAGGAGAAGGAGATCAACTTTGACAAGATCGTGGGCATCGATGTGAATTTCAAGCACGCCCTGTTTGTG
GCCTCTGAGAGAGACAAGAACCCACTGCAGGATAACAATCAGCTGAAGGGCTACATCAACCTGTACGGC
TATCTGCTGGAGCACAATGAGTTCACCAGCCTGCTGACAAAGGAGGAGCTGGACATCTACAAGGAGATC
GCCAAGGGCGTGACCTTCTGCCCCCTGGAGTATAACCTGCTGTTTACAAGGATCGAGAACAAGGGCGGC
AAGTCCAATGATAAGGAGCAGGTGCTGAGCAAGCTGCTGTACTCCCTGCAGATCAAGCTGAAGAACGAG
AATAAGATCCAGGAGTACATCTACGTGAGCTGCGTGAATAAGCTGCGCGCCAAGTACGTGAGCTATTTC
ATCCTGAAGGAGAAGTACTATGAGAAGCAGAAGGAGTACGACATCGAGATGGGCTTTACCGACGATAGC
ACAGAGTCCAAGGAGTCTATGGATAAGAGGCGCCTGGAGTTCCCTTTTCGGAACACCCAGATCGCCAAT
GGCTTCCTGGAGAAGCTGAGCAACGTGCAGCAGGACATCAATGGCTGTCTGAAGAACATCATCAATTAC
GCCTATAAGGTGTTCGAGCAGAACGGCTTTGGCGTGATCGCCCTGGAGAATCTGGAGAACAGCAATTTT
GAGAAGACCCAGGTGCTGCCAACAATCAAGTCCCTGCTGCGTTACCACAAGCTGGAGAACCAGAATATC
AACAATATCAACGCCTCTGACAAGGTGAAGGAGTATATCGAGAAGGAGTACTATGAGCTGACCACAAAT
GAGAACAATGAGATCGTGGATGCCAAGTACACCAAGAAGGGCATCATCAAGGTGAAGAAGGCCAACTTC
TTTAATCTGATGATGAAGTCTCTGCACTTCGCCAGCAACAAGGACGAGTTTATCCTGCTGTCCAACAAT
GGCAAGACCCAGATCGCCCTGGTGCCCAGCGAGTACACATCCCAGATGGATTCTATCGAGCACTGCCTG
TATGTGGACAAGAACGGCAAGAAGGTGGATAAGAAGAAGGTGCGCAGAAGCAGGAGACCCACATCAAC
GGCCTGAATGCCGACTTCAATGCCGCCAACAATATCAAGTACATCATCGAGAACGAGAATCTGAGAAAG
CTGTTTTGTGGCAAGCTGAAGGTGTCCGGCTATAACACCCCTATCCTGCGTGCCACAAAGAAGGGCCAG
TTCAACATCCTGGCCGAGCTGAAGAAGCAGAATAAGATCAAGATCTTTGAGATCGAGAAG
```

Functionality of Variant Polypeptides

As used herein, a "biologically active portion" is a portion that retains at least one function (e.g., completely, partially, minimally) of the parent polypeptide (e.g., a "minimal" or "core" domain). In some embodiments, the variant polypeptide retains enzymatic activity at least as active as the parent polypeptide. Accordingly, in some embodiments, a variant polypeptide has enzymatic activity greater than the parent polypeptide.

In some embodiments, the variant polypeptide has reduced nuclease activity or is a nuclease dead polypeptide. As used herein, catalytic residues of a polypeptide disclosed herein comprise D336 and E545. In some embodiments, a variant polypeptide comprising a substitution at D336 and E545 (e.g., D336A and E545A) exhibits reduced nuclease activity or no nuclease activity relative to a parent polypeptide. In some embodiments, a variant polypeptide comprising a substitution at D695, D661, or D636 (e.g., D695A, D661A, or D636A) exhibits reduced nuclease activity or no nuclease activity relative to a parent polypeptide.

In an aspect, the invention provides methods for introducing an alteration or mutation into the parent polypeptide sequence to enhance binary complex formation, RNA guide binding activity, and/or RNA guide binding specificity.

In an aspect, the invention also provides methods for introducing an alteration or mutation into the parent polypeptide sequence to enhance ternary complex formation, on-target binding affinity, on-target binding activity, on-target binding, and/or on-target binding specificity. In an aspect, the invention also provides methods for introducing an alteration or mutation into the parent polypeptide sequence to enhance on-target binding affinity (e.g., affinity or time it takes to interact with target), on-target binding activity, on-target binding (e.g., strength of interaction with target), and/or on-target binding specificity (e.g., preference for specific target) of a binary complex (e.g., ribonucleoprotein). In some embodiments, an alteration or mutation is introduced to the parent polypeptide sequence to produce a variant polypeptide that has increased on-target binding and/or activity. Also, in such embodiments, off-target binding and/or activity can be decreased in the variant polypeptide, as compared to the parent polypeptide. Moreover, there can be increased or decreased specificity as to on-target binding vs. off-target binding. In some embodiments, an alteration or mutation is introduced to the parent polypeptide sequence to produce a variant polypeptide, that when complexed with an RNA guide, has increased on-target binding. Also, in such embodiments, off-target binding can be decreased in the complex comprising the variant polypeptide and RNA guide. Moreover, there can be increased or decreased specificity as to on-target binding/activity vs. off-target binding/activity. In certain embodiments, an alteration or mutation is introduced to the parent polypeptide sequence to produce a variant polypeptide that enhances stability and/or protein-RNA interactions. In certain embodiments, variant polypeptide includes at least one alteration that promotes stability and/or RNA interactions as well as enzymatic activity of the variant polypeptide, as compared to a parent polypeptide.

In some embodiments, the variant polypeptide of the present invention has enzymatic activity equivalent to or greater than the parent polypeptide. In some embodiments, the variant polypeptide of the present invention has enzymatic activity at a temperature range from about 20° C. to about 90° C. In some embodiments, the variant polypeptide of the present invention has enzymatic activity at a temperature of about 20° C. to about 25° C. or at a temperature of about 37° C.

In some embodiments, the variant polypeptide comprises at least one alteration that enhances affinity to RNA (e.g., RNA affinity), as compared to a parent polypeptide. In some embodiments, the variant polypeptide exhibits enhanced RNA affinity, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced RNA affinity, as compared to a parent polypeptide, in a buffer having a pH in a range of about 7.3 to about 8.6. In some embodiments, the variant polypeptide exhibits enhanced RNA affinity, as compared to a parent polypeptide, when the $T_m$ value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant polypeptide exhibits enhanced RNA affinity when the $T_m$ value of the variant polypeptide is at least 8° C. greater than the $T_m$ value of the parent polypeptide.

In some embodiments, the variant polypeptide comprises at least one alteration that enhances complex formation with an RNA guide (e.g., binary complex formation), as compared to a parent polypeptide. In some embodiments, the variant polypeptide exhibits enhanced binary complex formation, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced binary complex formation, as compared to a parent polypeptide, in a buffer having a pH in a range of about 7.3 to about 8.6. In some embodiments, the variant polypeptide exhibits enhanced binary complex formation, as compared to a parent polypeptide, when the $T_m$ value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant polypeptide exhibits enhanced binary complex formation when the $T_m$ value of the variant polypeptide is at least 8° C. greater than the $T_m$ value of the parent polypeptide.

In some embodiments, the variant polypeptide comprises at least one alteration that enhances binding activity to an RNA guide, as compared to a parent polypeptide. In some embodiments, the variant polypeptide exhibits enhanced RNA guide binding activity, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced RNA guide binding activity, as compared to a parent polypeptide, in a buffer having a pH in a range of about 7.3 to about 8.6. In some embodiments, the variant polypeptide exhibits enhanced RNA guide binding activity, as compared to a parent polypeptide, when the $T_m$ value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant polypeptide exhibits enhanced RNA guide binding activity when the $T_m$ value of the variant polypeptide is at least 8° C. greater than the $T_m$ value of the parent polypeptide.

In some embodiments, the variant polypeptide comprises at least one alteration that enhances binding specificity to an RNA guide, as compared to a parent polypeptide. In some embodiments, the variant polypeptide exhibits enhanced RNA guide binding specificity, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced RNA guide binding specificity, as compared to a parent polypeptide, in a buffer having a pH in a range of about 7.3 to about 8.6. In some embodiments, the variant polypeptide exhibits enhanced RNA guide binding specificity, as compared to a parent polypeptide, when the $T_m$ value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C.

greater than the $T_m$ value of a parent polypeptide. In one embodiment, the variant polypeptide exhibits enhanced RNA guide binding specificity when the $T_m$ value of the variant polypeptide is at least 8° C. greater than the $T_m$ value of the parent polypeptide.

In some embodiments, the variant polypeptide comprises at least one alteration that enhances protein-RNA interactions, as compared to a parent polypeptide. In some embodiments, the variant polypeptide exhibits enhanced protein-RNA interactions, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced protein-RNA interactions, as compared to a parent polypeptide, in a buffer having a pH in a range of about 7.3 to about 8.6. In some embodiments, the variant polypeptide exhibits enhanced protein-RNA interactions, as compared to a parent polypeptide, when the $T_m$ value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant polypeptide exhibits enhanced protein-RNA interactions when the $T_m$ value of the variant polypeptide is at least 8° C. greater than the $T_m$ value of the parent polypeptide.

In some embodiments, the variant polypeptide comprises at least one alteration that enhances protein stability, as compared to a parent polypeptide. In some embodiments, the variant polypeptide exhibits enhanced protein stability, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced protein stability, as compared to a parent polypeptide, in a buffer having a pH in a range of about 7.3 to about 8.6. In some embodiments, the variant polypeptide exhibits enhanced protein stability, as compared to a parent polypeptide, when the $T_m$ value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant polypeptide exhibits enhanced protein stability when the $T_m$ value of the variant polypeptide is at least 8° C. greater than the $T_m$ value of the parent polypeptide.

In some embodiments, the variant polypeptide comprises at least one alteration that decreases dissociation from an RNA guide (e.g., binary complex dissociation), as compared to a parent polypeptide. In some embodiments, the variant polypeptide exhibits decreased dissociation from an RNA guide, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits decreased dissociation from an RNA guide, as compared to a parent polypeptide, in a buffer having a pH in a range of about 7.3 to about 8.6. In some embodiments, the variant polypeptide exhibits decreased dissociation from an RNA guide, as compared to a parent polypeptide, when the $T_m$ value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant polypeptide exhibits decreased dissociation from an RNA guide when the $T_m$ value of the variant polypeptide is at least 8° C. greater than the $T_m$ value of the parent polypeptide. In some embodiments, the variant polypeptide exhibits decreased dissociation from an RNA guide, as compared to a parent polypeptide, over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours. In some embodiments, a variant ribonucleoprotein (RNP) complex does not exchange the RNA guide with a different RNA.

In some embodiments, the variant polypeptide comprises at least one alteration that enhances ternary complex formation with an RNA guide and a target nucleic acid, as compared to a parent polypeptide. In some embodiments, the variant polypeptide exhibits enhanced ternary complex formation, as compared to a parent polypeptide, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant polypeptide exhibits enhanced ternary complex formation, as compared to a parent polypeptide, in a buffer having a pH in a range of about 7.3 to about 8.6. In some embodiments, the variant polypeptide exhibits enhanced ternary complex formation, as compared to a parent polypeptide, when the $T_m$ value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant polypeptide exhibits enhanced ternary complex formation when the $T_m$ value of the variant polypeptide is at least 8° C. greater than the $T_m$ value of the parent polypeptide.

In some embodiments, the variant polypeptide comprises at least one alteration such that a binary complex comprising the variant polypeptide (e.g., a variant binary complex) exhibits enhanced binding affinity to a target nucleic acid, as compared to a parent binary complex. In some embodiments, the variant binary complex exhibits enhanced binding affinity to a target nucleic acid, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits enhanced binding affinity to a target nucleic acid, as compared to a parent binary complex, in a buffer having a pH in a range of about 7.3 to about 8.6. In some embodiments, the variant binary complex exhibits enhanced binding affinity to a target nucleic acid, as compared to a parent binary complex, when the $T_m$ value of the variant binary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent binary complex. In one embodiment, the variant binary complex exhibits enhanced binding affinity to a target nucleic acid when the $T_m$ value of the variant binary complex is at least 8° C. greater than the $T_m$ value of the parent binary complex.

In some embodiments, the variant polypeptide comprises at least one alteration such that a binary complex comprising the variant polypeptide (e.g., a variant binary complex) exhibits enhanced on-target binding activity, as compared to a parent binary complex. In some embodiments, the variant binary complex exhibits enhanced on-target binding activity, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits enhanced on-target binding activity, as compared to a parent binary complex, in a buffer having a pH in a range of about 7.3 to about 8.6. In some embodiments, the variant binary complex exhibits enhanced on-target binding activity, as compared to a parent binary complex, when the $T_m$ value of the variant binary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent binary complex. In one embodiment, the variant binary complex exhibits enhanced on-target binding activity when the $T_m$ value of the variant binary complex is at least 8° C. greater than the $T_m$ value of the parent binary complex.

In some embodiments, the variant polypeptide comprises at least one alteration such that a binary complex comprising the variant polypeptide (e.g., a variant binary complex) exhibits enhanced on-target binding specificity, as compared to a parent binary complex. In some embodiments, the variant binary complex exhibits enhanced on-target binding specificity, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits enhanced on-target binding specificity, as compared to a parent binary complex, in a buffer having a pH in a range of about 7.3 to about 8.6. In some embodiments, the variant binary complex exhibits enhanced on-target binding specificity, as compared to a parent binary complex, when the $T_m$ value of the variant binary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent binary complex. In one embodiment, the variant binary complex exhibits enhanced on-target binding specificity when the $T_m$ value of the variant binary complex is at least 8° C. greater than the $T_m$ value of the parent binary complex.

In some embodiments, the variant polypeptide comprises at least one alteration such that a binary complex comprising the variant polypeptide (e.g., a variant binary complex) exhibits decreased off-target binding to a non-target nucleic acid, as compared to a parent binary complex. In some embodiments, the variant binary complex exhibits decreased off-target binding to a non-target nucleic acid, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits decreased off-target binding to a non-target nucleic acid, as compared to a parent binary complex, in a buffer having a pH in a range of about 7.3 to about 8.6. In some embodiments, the variant binary complex exhibits decreased off-target binding to a non-target nucleic acid, as compared to a parent binary complex, when the $T_m$ value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant binary complex exhibits decreased off-target binding to a non-target nucleic acid when the $T_m$ value of the variant binary complex is at least 8° C. greater than the $T_m$ value of the parent polypeptide.

In some embodiments, the variant polypeptide comprises at least one alteration such that a binary complex comprising the variant polypeptide (e.g., a variant binary complex) exhibits decreased dissociation from the target nucleic acid, as compared to a parent binary complex. In some embodiments, the variant binary complex exhibits decreased dissociation from the target nucleic acid, as compared to a parent binary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant binary complex exhibits decreased dissociation from the target nucleic acid, as compared to a parent binary complex, in a buffer having a pH in a range of about 7.3 to about 8.6. In some embodiments, the variant binary complex exhibits decreased dissociation from the target nucleic acid, as compared to a parent binary complex, when the $T_m$ value of the variant polypeptide is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent polypeptide. In one embodiment, the variant binary complex exhibits decreased dissociation from the target nucleic acid when the $T_m$ value of the variant binary complex is at least 8° C. greater than the $T_m$ value of the parent polypeptide.

In some embodiments, the variant polypeptide comprises at least one alteration such that a ternary complex comprising the variant polypeptide (e.g., a variant ternary complex) exhibits enhanced stability, as compared to a parent ternary complex. In some embodiments, the variant ternary complex exhibits enhanced stability, as compared to a parent ternary complex, at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., 51° C., 52° C., 53° C., 54° C., 55° C., 56° C., 57° C., 58° C., 59° C., 60° C. or 65° C. In some embodiments, the variant ternary complex exhibits enhanced stability, as compared to a parent ternary complex, in a buffer having a pH in a range of about 7.3 to about 8.6. In some embodiments, the variant ternary complex exhibits enhanced stability, as compared to a parent ternary complex, when the $T_m$ value of the variant ternary complex is at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C. greater than the $T_m$ value of a parent ternary complex. In one embodiment, the variant ternary complex exhibits enhanced stability when the $T_m$ value of the variant ternary complex is at least 8° C. greater than the $T_m$ value of the parent ternary complex.

In some embodiments, at least one alteration is introduced into the parent polypeptide of SEQ ID NO: 3 to produce a variant polypeptide that exhibits (a) decreased enzymatic activity and (b) enhanced RNA affinity relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced RNA affinity, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced RNA affinity, relative to the parent polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that exhibits (a) decreased enzymatic activity and (b) enhanced binary complex formation relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced binary complex formation, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced binary complex formation, relative to the parent polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that exhibits (a) decreased enzymatic activity and (b) enhanced RNA guide binding activity relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced RNA guide binding activity, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced RNA guide binding activity, relative to the parent polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that exhibits (a) decreased enzymatic activity and (b) enhanced RNA guide binding specificity relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced RNA guide binding specificity, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced RNA guide binding specificity, relative to the parent polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that exhibits (a) decreased enzymatic activity and (b) enhanced protein-RNA interactions relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced protein-RNA interactions, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced protein-RNA interactions, relative to the parent polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that exhibits (a) decreased enzymatic activity and (b) enhanced protein stability relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced protein stability, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced protein stability, relative to the parent polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that exhibits (a) decreased enzymatic activity and (b) decreased dissociation from an RNA guide relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) decreased dissociation from an RNA guide, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) decreased dissociation from an RNA guide, relative to the parent polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that exhibits (a) decreased enzymatic activity and (b) enhanced ternary complex formation relative to the parent polypeptide of SEQ ID NO: 3. In some embodiments, at least one alteration is introduced into the parent polypeptide of SEQ ID NO: 3 to produce a variant polypeptide that exhibits (a) increased enzymatic activity and (b) enhanced ternary complex formation, relative to the parent polypeptide of SEQ ID NO: 3. In some embodiments, at least one alteration is introduced into the parent polypeptide of SEQ ID NO: 3 to produce a variant polypeptide that exhibits (a) retained enzymatic activity and (b) enhanced ternary complex formation, relative to the parent polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that forms a variant binary complex exhibiting (a) decreased enzymatic activity and (b) enhanced binding affinity to a target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) increased enzymatic activity and (b) enhanced binding affinity to a target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex that exhibits (a) retained enzymatic activity and (b) enhanced binding affinity to a target nucleic acid, relative to a parent binary complex comprising the polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that forms a variant binary complex exhibiting (a) decreased enzymatic activity and (b) enhanced on-target binding activity, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) increased enzymatic activity and (b) enhanced on-target binding activity, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex that exhibits (a) retained enzymatic activity and (b) enhanced on-target binding activity, relative to a parent binary complex comprising the polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that forms a variant binary complex exhibiting (a) decreased enzymatic activity and (b) enhanced on-target binding specificity, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) increased enzymatic activity and (b) enhanced on-target binding specificity, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex that exhibits (a) retained enzymatic activity and (b) enhanced on-target binding specificity, relative to a parent binary complex comprising the polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that forms a variant binary complex exhibiting (a) decreased enzymatic activity and (b) decreased off-target binding to a non-target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) increased enzymatic activity and (b) decreased off-target binding to a non-target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) retained enzymatic activity and (b) decreased off-target binding to a non-target nucleic acid, relative to a parent binary complex comprising the polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

In some embodiments, at least one alteration is introduced into the parent polypeptide of SEQ ID NO: 3 to produce a variant polypeptide that forms a variant binary complex exhibiting (a) decreased enzymatic activity and (b) decreased dissociation from the target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) increased enzymatic activity and (b) decreased dissociation from the target nucleic acid, relative to a parent binary complex comprising the polypeptide of SEQ ID NO: 3. In some embodiments, at least one alteration is introduced into the parent polypeptide of SEQ ID NO: 3 to produce a variant polypeptide that forms a variant binary complex exhibiting (a) retained enzymatic activity and (b) decreased dissociation from the target nucleic acid, relative to a parent binary complex comprising the polypeptide of SEQ ID NO: 3. In some embodiments, the variant polypeptide having a feature as described herein comprises an amino acid sequence having at least about 60%, 65%, 70%, 75%, 80%, 85%, 90%, 91%, 92%, 93%, 94%, 95%, 96%, 97%, 98%, 99%, or 100% identity to any one of SEQ ID NOs: 14-41 or 49-58.

RNA Guide

In some embodiments, a composition or complex as described herein comprises a targeting moiety (e.g., an RNA guide, antisense, oligonucleotides, peptide oligonucleotide conjugates) that binds the target nucleic acid and interacts with the variant polypeptide. The targeting moiety may bind a target nucleic acid (e.g., with specific binding affinity to the target nucleic acid).

In some embodiments, the targeting moiety comprises, or is, an RNA guide. In some embodiments, the RNA guide directs the variant polypeptide described herein to a particular nucleic acid sequence. Those skilled in the art reading the below examples of particular kinds of RNA guides will understand that, in some embodiments, an RNA guide is site-specific. That is, in some embodiments, an RNA guide associates specifically with one or more target nucleic acid sequences (e.g., specific DNA or genomic DNA sequences) and not to non-targeted nucleic acid sequences (e.g., non-specific DNA or random sequences).

In some embodiments, the composition as described herein comprises an RNA guide that associates with the variant polypeptide described herein and directs the variant polypeptide to a target nucleic acid sequence (e.g., DNA).

The RNA guide may target (e.g., associate with, be directed to, contact, or bind) one or more nucleotides of a target sequence, e.g., a site-specific sequence or a site-specific target. In some embodiments, the variant nucleoprotein (e.g., variant polypeptide plus an RNA guide) is activated upon binding to a target nucleic acid that is complementary to a DNA-targeting sequence in the RNA guide (e.g., a sequence-specific substrate or target nucleic acid).

In some embodiments, an RNA guide comprises a spacer having a length of from about 11 nucleotides to about 100 nucleotides. For example, the DNA-targeting segment can have a length of from about 11 nucleotides to about 80 nucleotides, from about 11 nucleotides to about 50 nucleotides, from about 11 nucleotides to about 40 nucleotides, from about 11 nucleotides to about 30 nucleotides, from about 11 nucleotides to about 25 nucleotides, from about 11 nucleotides to about 20 nucleotides, or from about 11 nucleotides to about 19 nucleotides. For example, the spacer can have a length of from about 19 nucleotides to about 20 nucleotides, from about 19 nucleotides to about 25 nucleotides, from about 19 nucleotides to about 30 nucleotides, from about 19 nucleotides to about 35 nucleotides, from about 19 nucleotides to about 40 nucleotides, from about 19 nucleotides to about 45 nucleotides, from about 19 nucleotides to about 50 nucleotides, from about 19 nucleotides to about 60 nucleotides, from about 19 nucleotides to about 70 nucleotides, from about 19 nucleotides to about 80 nucleotides, from about 19 nucleotides to about 90 nucleotides, from about 19 nucleotides to about 100 nucleotides, from about 20 nucleotides to about 25 nucleotides, from about 20 nucleotides to about 30 nucleotides, from about 20 nucleotides to about 35 nucleotides, from about 20 nucleotides to about 40 nucleotides, from about 20 nucleotides to about 45 nucleotides, from about 20 nucleotides to about 50 nucleotides, from about 20 nucleotides to about 60 nucleotides, from about 20 nucleotides to about 70 nucleotides, from about 20 nucleotides to about 80 nucleotides, from about 20 nucleotides to about 90 nucleotides, or from about 20 nucleotides to about 100 nucleotides.

In some embodiments, the spacer of the RNA guide may be generally designed to have a length of between 11 and 50 nucleotides (e.g., 11, 12, 13, 14, 15, 16, 17, 18, 19, 20, 21, 22, 23, 24, 25, 26, 27, 28, 29, 30, 31, 32, 33, 34, or 35 nucleotides) and be complementary to a specific target nucleic acid sequence. In some particular embodiments, the RNA guide may be designed to be complementary to a specific DNA strand, e.g., of a genomic locus. In some embodiments, the DNA targeting sequence is designed to be complementary to a specific DNA strand, e.g., of a genomic locus.

The RNA guide may be substantially identical to a complementary strand of a reference nucleic acid sequence. In some embodiments, the RNA guide comprises a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to a complementary strand of a reference nucleic acid sequence, e.g., target nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters.

In some embodiments, the RNA guide has at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to a complementary strand of a target nucleic acid.

In some embodiments, the RNA guide comprises a spacer that is a length of between 11 and 50 nucleotides (e.g., 11, 12, 13, 14, 15, 16, 17, 18, 19, 20, 21, 22, 23, 24, 25, 26, 27, 28, 29, 30, 31, 32, 33, 34, or 35 nucleotides) and at least 80%, at least 90%, at least 95%, at least 96%, at least 97%, at least 98%, at least 99% complementary to a target nucleic acid. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence. In some embodiments, the RNA guide comprises a sequence, e.g., RNA sequence, that is a length of up to 50 and at least 80%, at least 90%, at least 95%, at least 96%, at least 97%, at least 98%, at least 99% complementary to a target nucleic acid. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence.

In certain embodiments, the RNA guide includes, consists essentially of, or comprises a direct repeat sequence linked to a DNA targeting sequence. In some embodiments, the RNA guide includes a direct repeat sequence and a DNA targeting sequence or a direct repeat-DNA targeting sequence-direct repeat sequence. In some embodiments, the RNA guide includes a truncated direct repeat sequence and a DNA targeting sequence, which is typical of processed or mature crRNA. In some embodiments, the variant polypeptide described herein forms a complex with the RNA guide, and the RNA guide directs the complex to associate with site-specific target nucleic acid that is complementary to at least a portion of the RNA guide.

In some embodiments, the direct repeat sequence is at least 90% identical to a sequence set forth in Table 4 or a portion of a sequence set forth in Table 4. In some embodiments, the direct repeat sequence is at least 95% identical to a sequence set forth in Table 4 or a portion of a sequence set forth in Table 4. In some embodiments, the direct repeat sequence is identical to a sequence set forth in Table 4 or a portion of a sequence set forth in Table 4.

TABLE 4

Direct repeat sequences.

| Sequence identifier | Direct Repeat Sequence |
|---|---|
| SEQ ID NO: 4 | CCUGUUGUGAAUACUCUUUUAUAGGUAUCAAACAAC |
| SEQ ID NO: 5 | CCUGUUGUGAAUACUCUUUAUAGGUAUCAAACAAC |

In some embodiments, the direct repeat comprises a sequence set forth as CCUGUUGUGAAUACUC (SEQ ID NO: 6). In some embodiments, the direct repeat comprises a sequence set forth as UUAUAGGUAUCAAACAAC (SEQ ID NO: 7).

In some embodiments, the composition or complex described herein includes one or more (e.g., two, three, four, five, six, seven, eight, or more) RNA guides, e.g., a plurality of RNA guides.

In some embodiments, the RNA guide has an architecture similar to, for example International Publication Nos. WO 2014/093622 and WO 2015/070083, the entire contents of each of which are incorporated herein by reference.

Unless otherwise noted, all compositions and complexes and polypeptides provided herein are made in reference to the active level of that composition or complex or polypeptide, and are exclusive of impurities, for example, residual solvents or by-products, which may be present in commercially available sources. Enzymatic component weights are based on total active protein. All percentages and ratios are calculated by weight unless otherwise indicated. All percentages and ratios are calculated based on the total composition unless otherwise indicated. In the exemplified composition, the enzymatic levels are expressed by pure enzyme by weight of the total composition and unless otherwise specified, the ingredients are expressed by weight of the total compositions.

Modifications

The RNA guide or any of the nucleic acid sequences encoding the variant polypeptides may include one or more covalent modifications with respect to a reference sequence, in particular the parent polyribonucleotide, which are included within the scope of this invention.

Exemplary modifications can include any modification to the sugar, the nucleobase, the internucleoside linkage (e.g. to a linking phosphate/to a phosphodiester linkage/to the phosphodiester backbone), and any combination thereof. Some of the exemplary modifications provided herein are described in detail below.

The RNA guide or any of the nucleic acid sequences encoding components of the variant polypeptides may include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

In some embodiments, the modification may include a chemical or cellular induced modification. For example, some nonlimiting examples of intracellular RNA modifications are described by Lewis and Pan in "RNA modifications and structures cooperate to guide RNA-protein interactions" from Nat Reviews Mol Cell Biol, 2017, 18:202-210.

Different sugar modifications, nucleotide modifications, and/or internucleoside linkages (e.g., backbone structures) may exist at various positions in the sequence. One of ordinary skill in the art will appreciate that the nucleotide analogs or other modification(s) may be located at any position(s) of the sequence, such that the function of the sequence is not substantially decreased. The sequence may include from about 1% to about 100% modified nucleotides (either in relation to overall nucleotide content, or in relation to one or more types of nucleotide, i.e. any one or more of A, G, U or C) or any intervening percentage (e.g., from 1% to 20%>, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, sugar modifications (e.g., at the 2' position or 4' position) or replacement of the sugar at one or more ribonucleotides of the sequence may, as well as backbone modifications, include modification or replacement of the phosphodiester linkages. Specific examples of a sequence include, but are not limited to, sequences including modified backbones or no natural internucleoside linkages such as internucleoside modifications, including modification or replacement of the phosphodiester linkages. Sequences having modified backbones include, among others, those that do not have a phosphorus atom in the backbone. For the purposes of this application, and as sometimes referenced in the art, modified RNAs that do not have a phosphorus atom in their internucleoside backbone can also be considered to be oligonucleosides. In particular embodiments, a sequence will include ribonucleotides with a phosphorus atom in its internucleoside backbone.

Modified sequence backbones may include, for example, phosphorothioates, chiral phosphorothioates, phosphorodithioates, phosphotriesters, aminoalkylphosphotriesters, methyl and other alkyl phosphonates such as 3'-alkylene phosphonates and chiral phosphonates, phosphinates, phosphoramidates such as 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments, the sequence may be negatively or positively charged.

The modified nucleotides, which may be incorporated into the sequence, can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment.

In specific embodiments, a modified nucleoside includes an alpha-thio-nucleoside (e.g., 5'-O-(1-thiophosphate)-adenosine, 5'-O-(1-thiophosphate)-cytidine (a-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present invention, including internucleoside linkages which do not contain a phosphorous atom, are described herein.

In some embodiments, the sequence may include one or more cytotoxic nucleosides. For example, cytotoxic nucleosides may be incorporated into sequence, such as bifunctional modification. Cytotoxic nucleoside may include, but are not limited to, adenosine arabinoside, 5-azacytidine, 4'-thio-aracytidine, cyclopentenylcytosine, cladribine, clofarabine, cytarabine, cytosine arabinoside, 1-(2-C-cyano-2-deoxy-beta-D-arabino-pentofuranosyl)-cytosine, decitabine, 5-fluorouracil, fludarabine, floxuridine, gemcitabine, a combination of tegafur and uracil, tegafur ((RS)-5-fluoro-1-(tetrahydrofuran-2-yl)pyrimidine-2,4(1H,3H)-dione), troxacitabine, tezacitabine, 2'-deoxy-2'-methylidenecytidine (DMDC), and 6-mercaptopurine. Additional examples include fludarabine phosphate, N4-behenoyl-1-beta-D-arabinofuranosylcytosine, N4-octadecyl-1-beta-D-arabinofuranosylcytosine, N4-palmitoyl-1-(2-C-cyano-2-deoxy-beta-D-arabino-pentofuranosyl) cytosine, and P-4055 (cytarabine 5'-elaidic acid ester).

In some embodiments, the sequence includes one or more post-transcriptional modifications (e.g., capping, cleavage, polyadenylation, splicing, poly-A sequence, methylation, acylation, phosphorylation, methylation of lysine and arginine residues, acetylation, and nitrosylation of thiol groups and tyrosine residues, etc.). The one or more post-transcriptional modifications can be any post-transcriptional modification, such as any of the more than one hundred different nucleoside modifications that have been identified in RNA (Rozenski, J, Crain, P, and McCloskey, J. (1999). The RNA Modification Database: 1999 update. Nucl Acids Res 27: 196-197) In some embodiments, the first isolated nucleic acid comprises messenger RNA (mRNA). In some embodiments, the mRNA comprises at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, the mRNA comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In some embodiments, the mRNA comprises at least one nucleoside selected from the group consisting of 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine. In some embodiments, mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethyl-guanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The sequence may or may not be uniformly modified along the entire length of the molecule. For example, one or more or all types of nucleotide (e.g., naturally-occurring nucleotides, purine or pyrimidine, or any one or more or all of A, G, U, C, I, pU) may or may not be uniformly modified in the sequence, or in a given predetermined sequence region thereof. In some embodiments, the sequence includes a pseudouridine. In some embodiments, the sequence includes an inosine, which may aid in the immune system characterizing the sequence as endogenous versus viral RNAs. The incorporation of inosine may also mediate improved RNA stability/reduced degradation. See for example, Yu, Z. et al. (2015) RNA editing by ADAR1 marks dsRNA as "self". Cell Res. 25, 1283-1284, which is incorporated by reference in its entirety.

Target Nucleic Acid

The methods disclosed herein are applicable for a variety of target nucleic acids. In some embodiments, the target nucleic acid is a DNA, such as a DNA locus. In some embodiments, the target nucleic acid is an RNA, such as an RNA locus or mRNA. In some embodiments, the target nucleic acid is single-stranded (e.g., single-stranded DNA). In some embodiments, the target nucleic acid is double-stranded (e.g., double-stranded DNA). In some embodiments, the target nucleic acid comprises both single-stranded and double-stranded regions. In some embodiments, the target nucleic acid is linear. In some embodiments, the target nucleic acid is circular. In some embodiments, the target nucleic acid comprises one or more modified nucleotides, such as methylated nucleotides, damaged nucleotides, or nucleotides analogs. In some embodiments, the target nucleic acid is not modified.

The target nucleic acid may be of any length, such as about at least any one of 100 bp, 200 bp, 500 bp, 1000 bp, 2000 bp, 5000 bp, 10 kb, 20 kb, 50 kb, 100 kb, 200 kb, 500 kb, 1 Mb, or longer. The target nucleic acid may also comprise any sequence. In some embodiments, the target nucleic acid is GC-rich, such as having at least about any one of 40%, 45%, 50%, 55%, 60%, 65%, or higher GC content. In some embodiments, the target nucleic acid has a GC content of at least about 70%, 80%, or more. In some embodiments, the target nucleic acid is a GC-rich fragment in a non-GC-rich target nucleic acid. In some embodiments, the target nucleic acid is not GC-rich. In some embodiments, the target nucleic acid has one or more secondary structures or higher-order structures. In some embodiments, the target nucleic acid is not in a condensed state, such as in a chromatin, to render the target nucleic acid inaccessible by the variant polypeptide/RNA guide complex.

In some embodiments, the target nucleic acid is present in a cell. In some embodiments, the target nucleic acid is present in the nucleus of the cell. In some embodiments, the target nucleic acid is endogenous to the cell. In some embodiments, the target nucleic acid is a genomic DNA. In some embodiments, the target nucleic acid is a chromosomal DNA. In one embodiment, the target nucleic acid is an extrachromosomal nucleic acid. In some embodiments, the target nucleic acid is a protein-coding gene or a functional region thereof, such as a coding region, or a regulatory element, such as a promoter, enhancer, a 5' or 3' untranslated region, etc. In some embodiments, the target nucleic acid is a non-coding gene, such as transposon, miRNA, tRNA, ribosomal RNA, ribozyme, or lincRNA. In some embodiments, the target nucleic acid is a plasmid.

In some embodiments, the target nucleic acid is exogenous to a cell. In some embodiments, the target nucleic acid is a viral nucleic acid, such as viral DNA or viral RNA. In some embodiments, the target nucleic acid is a horizontally transferred plasmid. In some embodiments, the target nucleic acid is integrated in the genome of the cell. In some embodiments, the target nucleic acid is not integrated in the genome of the cell. In some embodiments, the target nucleic acid is a plasmid in the cell. In some embodiments, the target nucleic acid is present in an extrachromosomal array.

In some embodiments, the target nucleic acid is an isolated nucleic acid, such as an isolated DNA or an isolated RNA. In some embodiments, the target nucleic acid is present in a cell-free environment. In some embodiments, the target nucleic acid is an isolated vector, such as a plasmid. In some embodiments, the target nucleic acid is an ultrapure plasmid.

The target nucleic acid is a segment of the target nucleic acid that hybridizes to the RNA guide. In some embodiments, the target nucleic acid has only one copy of the target nucleic acid. In some embodiments, the target nucleic acid has more than one copy, such as at least about any one of 2, 3, 4, 5, 10, 100, or more copies of the target nucleic acid. For example, a target nucleic acid comprising a repeated sequence in a genome of a viral nucleic acid or a bacterium may be targeted by the variant nucleoprotein.

The target sequence is adjacent to a protospacer adjacent motif or PAM of the disclosure as described herein. The PAM may be immediately adjacent to the target sequence or, for example, within a small number (e.g., 1, 2, 3, 4, or 5) of nucleotides of the target sequence. In the case of a double-stranded target, the targeting moiety (e.g., an RNA guide) binds to a first strand of the target and a PAM sequence as described herein is present in the second, complementary strand. In such a case, the PAM sequence is immediately adjacent to (or within a small number, e.g., 1, 2, 3, 4, or 5 nucleotides of) a sequence in the second strand that is complementary to the sequence in the first strand to which the binding moiety binds.

In some embodiments, the sequence-specificity requires a complete match of the spacer sequence in the RNA guide to the non-PAM strand of a target nucleic acid. In other embodiments, the sequence specificity requires a partial (contiguous or non-contiguous) match of the spacer sequence in the RNA guide to the non-PAM strand of a target nucleic acid.

In some embodiments, the RNA guide or a complex comprising the RNA guide and a variant polypeptide described herein binds to a target nucleic acid at a sequence defined by the region of complementarity between the RNA guide and the target nucleic acid. In some embodiments, the PAM sequence described herein is located directly upstream of the target sequence of the target nucleic acid (e.g., directly 5' of the target sequence). In some embodiments, the PAM sequence described herein is located directly 5' of the target sequence on the non-spacer-complementary strand (e.g., non-target strand) of the target nucleic acid.

In some embodiments, PAMs corresponding to a variant polypeptide of the present invention include 5'-NNR-3', 5'-TNR-3', 5'-NTTN-3', 5'-NTTR-3', or 5'-TTTN-3'. As used herein, N's can each be any nucleotide (e.g., A, G, T, or C) or a subset thereof (e.g., R (A or G), Y (C or T), K (G or T), B (G, T, or C), H (A, C, or T). In some embodiments, the PAM comprises 5'-TTTG-3', 5'-TTCG-3', 5'-TTAG-3', 5'-TACG-3', 5'-ATTG-3', 5'-ATCG-3', 5'-TCTG-3', 5'-TTGG-3', 5'-CGTG-3', 5'-GTTA-3', 5'-TTAA-3', 5'-TTCA-3', or 5'-TGCG-3'. In some embodiments, a binary complex comprising a variant polypeptide of the present invention binds to a target nucleic acid adjacent to a 5'-NNR-3', 5'-TNR-3', 5'-NTTN-3', 5'-NTTR-3', or 5'-TTTN-3' sequence. In some embodiments, a binary complex comprising a variant polypeptide of the present invention binds to a target nucleic acid adjacent to a 5'-TTTG-3', 5'-TTCG-3', 5'-TTAG-3', 5'-TACG-3', 5'-ATTG-3', 5'-ATCG-3', 5'-TCTG-3', 5'-TTGG-3', 5'-CGTG-3', 5'-GTTA-3', 5'-TTAA-3', 5'-TTCA-3', or 5'-TGCG-3' sequence.

In some embodiments, the target nucleic acid is present in a readily accessible region of the target nucleic acid. In some embodiments, the target nucleic acid is in an exon of a target gene. In some embodiments, the target nucleic acid is across an exon-intron junction of a target gene. In some embodiments, the target nucleic acid is present in a non-coding region, such as a regulatory region of a gene. In some embodiments, wherein the target nucleic acid is exogenous to a cell, the target nucleic acid comprises a sequence that is not found in the genome of the cell.

Suitable DNA/RNA binding conditions include physiological conditions normally present in a cell. Other suitable DNA/RNA binding conditions (e.g., conditions in a cell-free system) are known in the art; see, e.g., Sambrook, supra. The strand of the target nucleic acid that is complementary to and hybridizes with the RNA guide is referred to as the "complementary strand" and the strand of the target nucleic acid that is complementary to the "complementary strand" (and is therefore not complementary to the RNA guide) is referred to as the "noncomplementary strand" or "non-complementary strand".

Preparation

In some embodiments, the variant polypeptide of the present invention can be prepared by (a) culturing bacteria which produce the variant polypeptide of the present invention, isolating the variant polypeptide, optionally, purifying the variant polypeptide, and complexing the variant polypeptide with RNA guide. The variant polypeptide can be also prepared by (b) a known genetic engineering technique, specifically, by isolating a gene encoding the variant polypeptide of the present invention from bacteria, constructing a recombinant expression vector, and then transferring the vector into an appropriate host cell that expresses the RNA guide for expression of a recombinant protein that complexes with the RNA guide in the host cell. Alternatively, the variant polypeptide can be prepared by (c) an in vitro coupled transcription-translation system and then complexes with RNA guide. Bacteria that can be used for preparation of the variant polypeptide of the present invention are not particularly limited as long as they can produce the variant polypeptide of the present invention. Some nonlimiting examples of the bacteria include *E. coli* cells described herein.

Vectors

The present invention provides a vector for expressing the variant polypeptide described herein or nucleic acids encoding the variant described herein may be incorporated into a vector. In some embodiments, a vector of the invention includes a nucleotide sequence encoding variant polypeptide. In some embodiments, a vector of the invention includes a nucleotide sequence encoding the variant polypeptide.

The present invention also provides a vector that may be used for preparation of the variant polypeptide or compositions comprising the variant polypeptide as described herein. In some embodiments, the invention includes the composition or vector described herein in a cell. In some embodiments, the invention includes a method of expressing the composition comprising the variant polypeptide, or vector or nucleic acid encoding the variant polypeptide, in a cell. The method may comprise the steps of providing the composition, e.g., vector or nucleic acid, and delivering the composition to the cell.

Expression of natural or synthetic polynucleotides is typically achieved by operably linking a polynucleotide encoding the gene of interest, e.g., nucleotide sequence encoding the variant polypeptide, to a promoter and incorporating the construct into an expression vector. The expression vector is not particularly limited as long as it includes a polynucleotide encoding the variant polypeptide of the present invention and can be suitable for replication and integration in eukaryotic cells.

Typical expression vectors include transcription and translation terminators, initiation sequences, and promoters useful for expression of the desired polynucleotide. For example, plasmid vectors carrying a recognition sequence for RNA polymerase (pSP64, pBluescript, etc.). may be used. Vectors including those derived from retroviruses such as lentivirus are suitable tools to achieve long-term gene transfer since they allow long-term, stable integration of a transgene and its propagation in daughter cells. Examples of vectors include expression vectors, replication vectors, probe generation vectors, and sequencing vectors. The expression vector may be provided to a cell in the form of a viral vector.

Viral vector technology is well known in the art and described in a variety of virology and molecular biology manuals. Viruses which are useful as vectors include, but are not limited to phage viruses, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers.

The kind of the vector is not particularly limited, and a vector that can be expressed in host cells can be appropriately selected. To be more specific, depending on the kind of the host cell, a promoter sequence to ensure the expression of the variant polypeptide from the polynucleotide is appropriately selected, and this promoter sequence and the polynucleotide are inserted into any of various plasmids etc. for preparation of the expression vector.

Additional promoter elements, e.g., enhancing sequences, regulate the frequency of transcriptional initiation. Typically, these are located in the region 30-110 bp upstream of the start site, although a number of promoters have recently been shown to contain functional elements downstream of the start site as well. Depending on the promoter, it appears that individual elements can function either cooperatively or independently to activate transcription.

Further, the disclosure should not be limited to the use of constitutive promoters. Inducible promoters are also contemplated as part of the disclosure. The use of an inducible promoter provides a molecular switch capable of turning on expression of the polynucleotide sequence which it is operatively linked when such expression is desired or turning off the expression when expression is not desired. Examples of inducible promoters include, but are not limited to a metallothionine promoter, a glucocorticoid promoter, a progesterone promoter, and a tetracycline promoter.

The expression vector to be introduced can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate transcriptional control sequences to enable expression in the host cells. Examples of such a marker include a dihydrofolate reductase gene and a neomycin resistance gene for eukaryotic cell culture; and a tetracycline resistance gene and an ampicillin resistance gene for culture of *E. coli* and other bacteria. By use of such a selection marker, it can be confirmed whether the polynucleotide encoding the variant polypeptide of the present invention has been transferred into the host cells and then expressed without fail.

The preparation method for recombinant expression vectors is not particularly limited, and examples thereof include methods using a plasmid, a phage or a cosmid.

Methods of Expression

The present invention includes a method for protein expression, comprising translating the variant polypeptide described herein.

In some embodiments, a host cell described herein is used to express the variant polypeptide. The host cell is not particularly limited, and various known cells can be preferably used. Specific examples of the host cell include bacteria such as *E. coli*, yeasts (budding yeast, *Saccharomyces cerevisiae*, and fission yeast, *Schizosaccharomyces pombe*), nematodes (*Caenorhabditis elegans*), *Xenopus laevis* oocytes, and animal cells (for example, CHO cells, COS cells and HEK293 cells). The method for transferring the expression vector described above into host cells, i.e., the transformation method, is not particularly limited, and known methods such as electroporation, the calcium phosphate method, the liposome method and the DEAE dextran method can be used.

After a host is transformed with the expression vector, the host cells may be cultured, cultivated or bred, for production of the variant polypeptide. After expression of the variant polypeptide, the host cells can be collected and variant polypeptide purified from the cultures etc. according to conventional methods (for example, filtration, centrifugation, cell disruption, gel filtration chromatography, ion exchange chromatography, etc.).

In some embodiments, the methods for variant polypeptide expression comprises translation of at least 5 amino acids, at least 10 amino acids, at least 15 amino acids, at least 20 amino acids, at least 50 amino acids, at least 100 amino acids, at least 150 amino acids, at least 200 amino acids, at least 250 amino acids, at least 300 amino acids, at least 400 amino acids, at least 500 amino acids, at least 600 amino acids, at least 700 amino acids, at least 800 amino acids, at least 900 amino acids, or at least 1000 amino acids of the variant polypeptide. In some embodiments, the methods for protein expression comprises translation of about 5 amino acids, about 10 amino acids, about 15 amino acids, about 20 amino acids, about 50 amino acids, about 100 amino acids, about 150 amino acids, about 200 amino acids, about 250 amino acids, about 300 amino acids, about 400 amino acids, about 500 amino acids, about 600 amino acids, about 700 amino acids, about 800 amino acids, about 900 amino acids, about 1000 amino acids or more of the variant polypeptide.

A variety of methods can be used to determine the level of production of a mature variant polypeptide in a host cell. Such methods include, but are not limited to, for example, methods that utilize either polyclonal or monoclonal antibodies specific for the variant polypeptide or a labeling tag as described elsewhere herein. Exemplary methods include, but are not limited to, enzyme-linked immunosorbent assays (ELISA), radioimmunoassays (MA), fluorescent immunoassays (FIA), and fluorescent activated cell sorting (FACS). These and other assays are well known in the art (See, e.g., Maddox et al., J. Exp. Med. 158:1211 [1983]).

The present disclosure provides methods of in vivo expression of the variant polypeptide in a cell, comprising providing a polyribonucleotide encoding the variant polypeptide to a host cell wherein the polyribonucleotide encodes the variant polypeptide, expressing the variant polypeptide in the cell, and obtaining the variant polypeptide from the cell.

Introduction of Alteration or Mutation

Nucleic acid sequences encoding variant polypeptides or variant polypeptides may be generated by synthetic methods known in the art. Using the nucleic acid sequence encoding the parent polypeptide itself as a framework, alternations or mutations can be inserted one or more at a time to alter the nucleic acid sequence encoding the parent polypeptide. Along the same lines, the parent polypeptide may be altered or mutated by introducing the changes into the polypeptide sequence as it is synthetically synthesized. This may be accomplished by methods well known in the art.

The production and introduction of alteration or mutation into a parent polypeptide sequence can be accomplished using any methods known by those of skill in the art. In particular, in some embodiments, oligonucleotide primers for PCR may be used for the rapid synthesis of a DNA template including the one or more alterations or mutations in the nucleic acid sequence encoding for the variant polypeptide. Site-specific mutagenesis may also be used as a technique useful in the preparation of individual peptides, or biologically functional equivalent proteins or peptides, through specific mutagenesis of the underlying DNA. The technique further provides a ready ability to prepare and test variants, incorporating one or more of the foregoing considerations, by introducing one or more nucleotide sequence changes into the DNA. Site-specific mutagenesis allows the production of variants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

Introduction of structural variations, such as fusion of polypeptides as amino- and/or carboxyl-terminal extensions can be accomplished in a similar fashion as introduction of alterations or mutations into the parent polypeptide. The additional peptides may be added to the parent polypeptide or variant polypeptide by including the appropriate nucleic acid sequence encoding the additional peptides to the nucleic acid sequence encoding the parent polypeptide or variant polypeptide. Optionally, the additional peptides may be appended directly to the variant polypeptide through synthetic polypeptide production.

In an aspect, the invention also provides methods for introducing an alteration or mutation into the parent polypeptide sequence to produce a variant polypeptide that has increased on-target binding with two or more loci (e.g., 2, 3, 4, 5, 6, 7, 8, 9, or more) of a target nucleic acid, as compared to a parent polypeptide.

In an aspect, the invention also provides methods for introducing an alteration or mutation into the parent polypeptide sequence to produce a plurality of variant polypeptides (e.g., separate variant polypeptides having the same amino acid sequence), that when individually complexed with a plurality of distinct RNA guides, have increased on-target binding with two or more loci of a target nucleic acid, as compared to a plurality of parent polypeptides and RNA guides.

In an aspect, the invention also provides methods for introducing an alteration or mutation into the parent polypeptide sequence to produce a variant polypeptide that has increased on-target ternary complex formation with two or more target loci of a target nucleic acid, as compared to a parent polypeptide.

In an aspect, the invention also provides methods for introducing an alteration or mutation into the parent polypeptide sequence to produce a plurality of variant polypeptides (e.g., separate variant polypeptides having the same amino acid sequence), that when individually complexed with a plurality of distinct RNA guides, have increased ternary complex formation with two or more loci of a target nucleic acid, as compared to a plurality of parent polypeptides and RNA guides.

In an aspect, the invention also provides methods for introducing an alteration or mutation into the parent polypeptide sequence to produce a variant polypeptide that exhibits targeting of an increased number of target nucleic acids or target loci, as compared to a parent polypeptide.

In an aspect, the invention also provides methods for introducing an alteration or mutation into the parent polypeptide sequence to produce a plurality of variant polypeptides (e.g., separate variant polypeptides having the same amino acid sequence), that when individually complexed with a plurality of distinct RNA guides, exhibit targeting of an increased number of target nucleic acids or target loci, as compared to a plurality of parent polypeptides and RNA guides.

In an aspect, the invention also provides methods for introducing an alteration or mutation into the parent polypeptide sequence to enhance stability of the variant polypeptide. Stability of the variant polypeptide can be determined by or may include a technique not limited to thermal denaturation assays, thermal shift assays, differential scanning calorimetry (DSC), differential scanning fluorimetry (DSF), isothermal titration calorimetry (ITC), pulse-chase methods, bleach-chase methods, cycloheximide-chase methods, circular dichroism (CD) spectroscopy, crystallization, and fluorescence-based activity assays.

Variant Binary Complexing

Generally, the variant polypeptide and the RNA guide bind to each other in a molar ratio of about 1:1 to form the variant binary complex. The variant polypeptide and the RNA guide, either alone or together, do not naturally occur.

In some embodiments, the variant polypeptide can be overexpressed in a host cell and purified as described herein, then complexed with the RNA guide (e.g., in a test tube) to form a variant ribonucleoprotein (RNP) (e.g., variant binary complex).

In some embodiments, the variant binary complex exhibits increased binding affinity to a target nucleic acid, increased on-target binding activity, increased on-target binding specificity, increased ternary complex formation with a target nucleic acid, and/or increased stability over a range of incubation times. In some embodiments, the variant binary complex exhibits decreased off-target binding to a non-target nucleic acid and/or decreased dissociation from a target nucleic acid over a range of incubation times. In some embodiments, the variant binary complex exhibits increased target nucleic acid complex formation, target nucleic acid activity, and/or target nucleic acid specificity over a range of incubation times.

In some embodiments, complexation of a binary complex occurs at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., or 55° C. In some embodiments, the variant polypeptide does not dissociate from the RNA guide or bind to a free RNA at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours. In some embodiments, after binary complex formation, the variant ribonucleoprotein complex does not exchange the RNA guide with a different RNA.

In some embodiments, the variant polypeptide and RNA guide are complexed in a binary complexation buffer. In some embodiments, the variant polypeptide is stored in a buffer that is replaced with a binary complexation buffer to form a complex with the RNA guide. In some embodiments, the variant polypeptide is stored in a binary complexation buffer.

In some embodiments, the binary complexation buffer has a pH in a range of about 7.3 to 8.6. In one embodiment, the pH of the binary complexation buffer is about 7.3. In one embodiment, the pH of the binary complexation buffer is about 7.4. In one embodiment, the pH of the binary complexation buffer is about 7.5. In one embodiment, the pH of the binary complexation buffer is about 7.6. In one embodiment, the pH of the binary complexation buffer is about 7.7. In one embodiment, the pH of the binary complexation buffer is about 7.8. In one embodiment, the pH of the binary complexation buffer is about 7.9. In one embodiment, the pH of the binary complexation buffer is about 8.0. In one embodiment, the pH of the binary complexation buffer is about 8.1. In one embodiment, the pH of the binary complexation buffer is about 8.2. In one embodiment, the pH of the binary complexation buffer is about 8.3. In one embodiment, the pH of the binary complexation buffer is about 8.4. In one embodiment, the pH of the binary complexation buffer is about 8.5. In one embodiment, the pH of the binary complexation buffer is about 8.6.

The thermostability of the variant polypeptide can increase under favorable conditions such as the addition of an RNA guide, e.g., binding an RNA guide.

In some embodiments, the variant polypeptide can be overexpressed and complexed with the RNA guide in a host cell prior to purification as described herein. In some embodiments, mRNA or DNA encoding the variant polypeptide is introduced into a cell so that the variant polypeptide is expressed in the cell. The RNA guide, which guides the variant polypeptide to the desired target nucleic acid is also introduced into the cell, whether simultaneously, separately or sequentially from a single mRNA or DNA construct, such that the necessary ribonucleoprotein complex is formed in the cell.

Assessing Variant Binary Complex Stability and Functionality

Provided herein in certain embodiments are methods for identifying an optimal variant polypeptide/RNA guide complex (referred to herein as the variant binary complex) including (a) combining a variant polypeptide and an RNA guide in a sample to form the variant binary complex; (b) measuring a value of the variant binary complex; and (c) determining the variant binary complex is optimal over the reference molecule, if the value of the variant binary complex is greater than a value of a reference molecule. In some embodiments, the value may include, but is not limited to, a stability measurement (e.g., $T_m$ value, thermostability), a rate of binary complex formation, RNA guide binding specificity, and/or complex activity.

In some embodiments, an optimal variant polypeptide/RNA guide complex (i.e., a variant binary complex) is identified by the steps of: (a) combining a variant polypeptide and an RNA guide in a sample to form the variant binary complex; (b) detecting a $T_m$ value of the variant binary complex; and (c) determining the variant binary complex is stable if the $T_m$ value of the variant binary complex is greater than a $T_m$ value of a reference molecule or a $T_m$ reference value by at least 8° C.

The methods involving a step of measuring the thermostability of a variant polypeptide/RNA guide complex (i.e., a variant binary complex) may include, without limitation, methods of determining the stability of a variant binary complex, methods of determining a condition that promotes a stable variant binary complex, methods of screening for a stable variant binary complex, and methods for identifying an optimal gRNA to form a stable variant binary complex. In certain embodiments, a thermostability value of a variant binary complex may be measured.

Additionally, in certain embodiments, a thermostability value of a reference molecule may also be measured. In certain embodiments, a variant binary complex may be determined to be stable if the measured thermostability value of the variant binary complex is greater than the measured thermostability value of the reference molecule or a thermostability reference value, measured under the same experimental conditions, as described herein. In certain embodiments, the reference molecule may be the variant polypeptide absent an RNA guide.

In certain embodiments, the thermostability value that is measured may be a denaturation temperature value. In these embodiments, the thermostability reference value is a denaturation temperature reference value. In certain embodiments, the thermostability value that is measured may be a $T_m$ value. In these embodiments, the thermostability reference value may be a $T_m$ reference value. In certain embodiments, the thermostability value may be measured using a thermal shift assay. In certain embodiments, an assay used to measure thermostability may involve a technique described herein including, but not limited to, thermal denaturation assays, thermal shift assays, differential scanning calorimetry (DSC), differential scanning fluorimetry (DSF), isothermal titration calorimetry (ITC), pulse-chase methods, bleach-chase methods, cycloheximide-chase methods, circular dichroism (CD) spectroscopy, crystallization, and fluorescence-based activity assays.

In certain embodiments, a variant binary complex may be identified if the rate of variant polypeptide/RNA guide complex formation, RNA guide binding specificity, and/or complex activity of the variant binary complex is greater than a value of the reference molecule or the reference value (e.g., a value of a parent polypeptide/RNA guide complex, referred to herein as a parent binary complex). For example, in certain embodiments, the variant binary complex may be identified if the value of a rate of variant polypeptide/RNA guide complex formation, RNA guide binding specificity, and/or complex activity of the variant binary complex is at least X % greater than a value of the reference molecule or the reference value (e.g., a value of a parent binary complex). In certain embodiments, the methods described herein may further comprise steps that include measuring the activity of the variant binary complex as described herein.

Variant Ternary Complexing

In some embodiments, the variant polypeptide, RNA guide, and target nucleic acid, as described herein, form a variant ternary complex (e.g., in a test tube or cell). Generally, the variant polypeptide, the RNA guide, and the target nucleic acid associate with each other in a molar ratio of about 1:1:1 to form the variant ternary complex. The variant polypeptide, the RNA guide, and the target nucleic acid, either alone or together, do not naturally occur.

In some embodiments, the variant binary complex (e.g., complex of variant polypeptide and RNA guide) as described herein, is further complexed with the target nucleic acid (e.g., in a test tube or cell) to form a variant ternary complex.

In some embodiments, complexation of the ternary complex occurs at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., or 55° C. In some embodiments, the variant binary complex does not dissociate from the target nucleic acid or bind to a free nucleic acid (e.g., free DNA) at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours. In some embodiments, after ternary complex formation, a variant binary complex does not exchange the target nucleic acid with a different nucleic acid.

In some embodiments, the variant polypeptide, RNA guide, and target nucleic acid are complexed in a ternary complexation buffer. In some embodiments, the variant polypeptide is stored in a buffer that is replaced with a ternary complexation buffer to form a complex with the RNA guide and target nucleic acid. In some embodiments, the variant polypeptide is stored in a ternary complexation buffer.

In some embodiments, the variant binary complex and target nucleic acid are complexed in a ternary complexation buffer. In some embodiments, the variant binary complex is stored in a buffer that is replaced with a ternary complexation buffer to form a complex with the target nucleic acid. In some embodiments, the variant binary complex is stored in a ternary complexation buffer.

In some embodiments, the ternary complexation buffer has a pH in a range of about 7.3 to 8.6. In one embodiment, the pH of the ternary complexation buffer is about 7.3. In one embodiment, the pH of the ternary complexation buffer is about 7.4. In one embodiment, the pH of the ternary complexation buffer is about 7.5. In one embodiment, the pH of the ternary complexation buffer is about 7.6. In one embodiment, the pH of the ternary complexation buffer is about 7.7. In one embodiment, the pH of the ternary complexation buffer is about 7.8. In one embodiment, the pH of the ternary complexation buffer is about 7.9. In one embodiment, the pH of the ternary complexation buffer is about 8.0. In one embodiment, the pH of the ternary complexation buffer is about 8.1. In one embodiment, the pH of the ternary complexation buffer is about 8.2. In one embodiment, the pH of the ternary complexation buffer is about 8.3. In one embodiment, the pH of the ternary complexation buffer is about 8.4. In one embodiment, the pH of the ternary complexation buffer is about 8.5. In one embodiment, the pH of the ternary complexation buffer is about 8.6.

The thermostability of a variant polypeptide can increase under favorable conditions such as the addition of an RNA guide and target nucleic acid.

Assessing Variant Ternary Complex Stability and Functionality

Provided herein in certain embodiments are methods for identifying an optimal variant ternary complex including (a) combining a variant polypeptide, an RNA guide, and a target nucleic acid in a sample to form the variant ternary complex; (b) measuring a value of the variant ternary complex; and (c) determining the variant ternary complex is optimal over the reference molecule, if the value of the variant ternary complex is greater than a value of a reference molecule. In some embodiments, the value may include, but is not limited to, a stability measurement (e.g., $T_m$ value, thermostability), a rate of ternary complex formation, a DNA binding affinity measurement, a DNA binding specificity measurement, and/or a complex activity measurement (e.g., nuclease activity measurement).

In some embodiments, an optimal variant ternary complex is identified by the steps of: (a) combining a variant polypeptide, an RNA guide, and a target nucleic acid in a sample to form the variant ternary complex; (b) detecting a $T_m$ value of the variant ternary complex; and (c) determining the variant ternary complex is stable if the $T_m$ value of the variant ternary complex is greater than a $T_m$ value of a reference molecule or a $T_m$ reference value by at least 8° C.

The methods involving a step of measuring the thermostability of a variant ternary complex may include, without limitation, methods of determining the stability of a variant ternary complex, methods of determining a condition that promotes a stable variant ternary complex, methods of screening for a stable variant ternary complex, and methods for identifying an optimal binary complex to form a stable variant ternary complex. In certain embodiments, a thermostability value of a variant ternary complex may be measured.

Additionally, in certain embodiments, a thermostability value of a reference molecule may also be measured. In certain embodiments, a variant ternary complex may be determined to be stable if the measured thermostability value of the variant ternary complex is greater than the measured thermostability value of the reference molecule or a thermostability reference value, measured under the same experimental conditions, as described herein. In certain embodiments, the reference molecule may be the variant polypeptide absent an RNA guide and/or target nucleic acid.

In certain embodiments, the thermostability value that is measured may be a denaturation temperature value. In these embodiments, the thermostability reference value is a denaturation temperature reference value. In certain embodiments, the thermostability value that is measured may be a $T_m$ value. In these embodiments, the thermostability reference value may be a $T_m$ reference value. In certain embodiments, the thermostability value may be measured using a thermal shift assay. In certain embodiments, an assay used to measure thermostability may involve a technique described herein including, but not limited to, differential scanning fluorimetry (DSF), differential scanning calorimetry (DSC), or isothermal titration calorimetry (ITC).

In certain embodiments, a variant ternary complex may be identified if the rate of ternary complex formation, DNA binding affinity, DNA binding specificity, and/or complex activity (e.g., nuclease activity) of the variant ternary complex is greater than a value of the reference molecule or the reference value (e.g., a value of a parent ternary complex). For example, in certain embodiments, the variant ternary complex may be identified if the value of a rate of ternary complex formation, DNA binding affinity, DNA binding specificity, and/or complex activity of the variant ternary complex is at least X % greater than a value of the reference molecule or the reference value (e.g., a value of a parent ternary complex). In certain embodiments, the methods described herein may further comprise steps that include measuring the activity of the variant ternary complex as described herein.

Delivery

Compositions or complexes described herein may be formulated, for example, including a carrier, such as a carrier and/or a polymeric carrier, e.g., a liposome, and delivered by known methods to a cell (e.g., a prokaryotic, eukaryotic, plant, mammalian, etc.). Such methods include, but not limited to, transfection (e.g., lipid-mediated, cationic polymers, calcium phosphate, dendrimers); electroporation or other methods of membrane disruption (e.g., nucleofection), viral delivery (e.g., lentivirus, retrovirus, adenovirus, AAV), microinjection, microprojectile bombardment ("gene gun"), fugene, direct sonic loading, cell squeezing, optical transfection, protoplast fusion, impalefection, magnetofection, exosome-mediated transfer, lipid nanoparticle-mediated transfer, and any combination thereof.

In some embodiments, the method comprises delivering one or more nucleic acids (e.g., nucleic acids encoding the variant polypeptide, RNA guide, donor DNA, etc.), one or more transcripts thereof, and/or a pre-formed variant polypeptide/RNA guide complex (i.e., variant binary complex) to a cell. Exemplary intracellular delivery methods, include, but are not limited to: viruses or virus-like agents; chemical-based transfection methods, such as those using calcium phosphate, dendrimers, liposomes, or cationic polymers (e.g., DEAE-dextran or polyethylenimine); non-chemical methods, such as microinjection, electroporation, cell squeezing, sonoporation, optical transfection, impalefection, protoplast fusion, bacterial conjugation, delivery of plasmids or transposons; particle-based methods, such as using a gene gun, magnetofection or magnet assisted transfection, particle bombardment; and hybrid methods, such as nucleofection. In some embodiments, the present application further provides cells produced by such methods, and organisms (such as animals, plants, or fungi) comprising or produced from such cells.

Cells

Polypeptides, compositions or complexes described herein may be delivered to a variety of cells. In some embodiments, the cell is an isolated cell. In some embodiments the cell is in cell culture. In some embodiments, the cell is ex vivo. In some embodiments, the cell is obtained from a living organism, and maintained in a cell culture. In some embodiments, the cell is a single-cellular organism.

In some embodiments, the cell is a prokaryotic cell. In some embodiments, the cell is a bacterial cell or derived from a bacterial cell. In some embodiments, the bacterial cell is not related to the bacterial species from which the parent polypeptide is derived. In some embodiments, the cell is an archaeal cell or derived from an archaeal cell. In some embodiments, the cell is a eukaryotic cell. In some embodiments, the cell is a plant cell or derived from a plant cell. In some embodiments, the cell is a fungal cell or derived from a fungal cell. In some embodiments, the cell is an animal cell or derived from an animal cell. In some embodiments, the cell is an invertebrate cell or derived from an invertebrate cell. In some embodiments, the cell is a vertebrate cell or derived from a vertebrate cell. In some embodiments, the cell is a mammalian cell or derived from a mammalian cell. In some embodiments, the cell is a human cell. In some embodiments, the cell is a zebra fish cell. In some embodiments, the cell is a rodent cell. In some embodiments, the cell is synthetically made, sometimes termed an artificial cell.

In some embodiments, the cell is derived from a cell line. A wide variety of cell lines for tissue culture are known in the art. Examples of cell lines include, but are not limited to, 293T, MF7, K562, HeLa, and transgenic varieties thereof. Cell lines are available from a variety of sources known to those with skill in the art (see, e.g., the American Type Culture Collection (ATCC) (Manassas, Va.)). In some embodiments, a cell transfected with one or more nucleic acids (such as Ago-coding vector and gDNA) or Ago-gDNA complex described herein is used to establish a new cell line comprising one or more vector-derived sequences to establish a new cell line comprising modification to the target nucleic acid. In some embodiments, cells transiently or non-transiently transfected with one or more nucleic acids (such as variant polypeptide-encoding vector and RNA guide) or variant polypeptide/RNA guide complex (i.e., variant binary complex) described herein, or cell lines derived from such cells are used in assessing one or more test compounds.

In some embodiments, the method comprises introducing into a host cell one or more nucleic acids comprising nucleotide sequences encoding a DNA-targeting RNA (e.g., RNA guide) and/or the variant polypeptide. In one embodiment, a cell comprising a target DNA is in vitro, in vivo, or ex vivo. In other embodiments, nucleic acids comprising nucleotide sequences encoding a DNA-targeting RNA (e.g., RNA guide) and/or the variant polypeptide include recombinant expression vectors e.g., including but not limited to adeno-associated virus constructs, recombinant adenoviral constructs, recombinant lentiviral constructs, recombinant retroviral constructs, and the like.

In some embodiments, the cell is a primary cell. For example, cultures of primary cells can be passaged 0 times, 1 time, 2 times, 4 times, 5 times, 10 times, 15 times or more. In some embodiments, the primary cells are harvest from an individual by any known method. For example, leukocytes may be harvested by apheresis, leukocytapheresis, density gradient separation, etc. Cells from tissues such as skin, muscle, bone marrow, spleen, liver, pancreas, lung, intestine, stomach, etc. can be harvested by biopsy. An appropriate solution may be used for dispersion or suspension of the harvested cells. Such solution can generally be a balanced salt solution, (e.g. normal saline, phosphate-buffered saline (PBS), Hank's balanced salt solution, etc.), conveniently supplemented with fetal calf serum or other naturally occurring factors, in conjunction with an acceptable buffer at low concentration. Buffers can include HEPES, phosphate buffers, lactate buffers, etc. Cells may be used immediately, or they may be stored (e.g., by freezing). Frozen cells can be thawed and can be capable of being reused. Cells can be frozen in a DMSO, serum, medium buffer (e.g., 10% DMSO, 50% serum, 40% buffered medium), and/or some other such common solution used to preserve cells at freezing temperatures.

In some embodiments, the variant polypeptide has nuclease activity that induces double-stranded breaks or single-stranded breaks in a target nucleic acid, (e.g. genomic DNA). The double-stranded break can stimulate cellular endogenous DNA-repair pathways, including Homology Directed Recombination (HDR), Non-Homologous End Joining (NHEJ), or Alternative Non-Homologues End-Joining (A-NHEJ). NHEJ can repair cleaved target nucleic acid without the need for a homologous template. This can result in deletion or insertion of one or more nucleotides into the target nucleic acid. HDR can occur with a homologous template, such as the donor DNA. The homologous template can comprise sequences that are homologous to sequences flanking the target nucleic acid cleavage site. In some cases, HDR can insert an exogenous polynucleotide sequence into the cleaved target nucleic acid. The modifications of the target DNA due to NHEJ and/or HDR can lead to, for example, mutations, deletions, alterations, integrations, gene correction, gene replacement, gene tagging, transgene knock-in, gene disruption, and/or gene knock-outs.

In some embodiments, the cell culture is synchronized to enhance the efficiency of the methods. In some embodiments, cells in S and G2 phases are used for HDR-mediated gene editing. In some embodiments, the cell can be subjected to the method at any cell cycle. In some embodiments, cell over-plating significantly reduces the efficacy of the method. In some embodiments, the method is applied to a cell culture at no more than about any one of 40%, 45%, 50%, 55%, 60%, 65%, or 70% confluency.

In some embodiments, binding of the variant polypeptide/RNA guide complex (i.e., variant binary complex) to the target nucleic acid in the cell recruits one or more endogenous cellular molecules or pathways other than DNA repair pathways to modify the target nucleic acid. In some embodiments, binding of the variant binary complex blocks access of one or more endogenous cellular molecules or pathways to the target nucleic acid, thereby modifying the target nucleic acid. For example, binding of the variant binary complex may block endogenous transcription or translation machinery to decrease the expression of the target nucleic acid.

In some embodiments, a method for modifying a target DNA molecule in a cell is provided. The method comprises contacting the target DNA molecule inside of a cell with a variant polypeptide described herein; and a single molecule DNA-targeting RNA comprising, in 5' to 3' order, a first nucleotide segment that hybridizes with a target sequence of the target DNA molecule; a nucleotide linker; and a second nucleotide segment that hybridizes with the first nucleotide segment to form a double-stranded RNA duplex. The variant polypeptide forms a complex with the single molecule DNA-targeting RNA inside the cell and the target DNA molecule is modified.

Kits

The invention also provides kits that can be used, for example, to carry out a method described herein. In some embodiments, the kits include a variant polypeptide of the invention, e.g., a variant of Table 2. In some embodiments, the kits include a polynucleotide that encodes such a variant polypeptide, and optionally the polynucleotide is comprised within a vector, e.g., as described herein. The kits also can optionally include an RNA guide, e.g., as described herein. The RNA guide of the kits of the invention can be designed to target a sequence of interest, as is known in the art. The variant polypeptide and the RNA guide can be packaged within the same vial or other vessel within a kit or can be packaged in separate vials or other vessels, the contents of which can be mixed prior to use. The kits can additionally include, optionally, a buffer and/or instructions for use of the variant polypeptide and/or RNA guide.

All references and publications cited herein are hereby incorporated by reference.

EXAMPLES

The following examples are provided to further illustrate some embodiments of the present invention but are not Example 1—Engineering of Variant Constructs In this Example, variant constructs were generated.

DNA templates comprising single mutations were constructed via two PCR steps using mutagenic forward and mutagenic reverse primers ordered from IDT™ (Integrated DNA Technologies, Inc.). In the first step, two sets of PCR reactions were conducted in 384 plates to generate two fragments. The overlapping regions of two PCR fragments contained the desired single mutations and allowed the assembly of the entire DNA template via a second PCR. In the second step, the purified fragments from the first step were used as the template for the overlapping PCR (OL PCR) and the Fw and Rv oligos annealing to the vector backbone as the OL PCR primers. The resulting linear DNA templates contained a T7 promoter, a T7 terminator, and the open-reading frame for the polypeptide.

These linear DNA templates were used directly in a cell-free transcription and translation system to express the polypeptide variants containing the single mutations. The variant constructs were further individually transferred into transient transfection vectors. Additionally, DNA templates comprising combinatorial mutations were prepared by PCR and subsequently transferred into transient transfection vectors.

Example 2—Florescence Polarization Assay for Variant Binary Complex Detection

In this Example, the ability of a wild-type or variant nuclease polypeptide and an RNA guide to form a binary complex is assessed through a fluorescence polarization assay.

Linear ssDNA fragments comprising the reverse complement of the T7 RNA polymerase promoter sequence upstream of the direct repeat sequence and desired 20 bp RNA guide target are synthesized by IDT™. Linear dsDNA in vitro transcription (IVT) templates are then generated by annealing a universal T7 forward oligo (95-4° C. at 5° C./minute) to the reverse complement ssDNA and filled in with Klenow fragment (New England Biolabs®) for 15 minutes at 25° C. The resulting IVT template is then transcribed into an RNA guide using the HiScribe T7 High Yield RNA Synthesis Kit (New England Biolabs®) at 37° C. for 4 hours. Following transcription, each RNA guide is purified using an RNA Clean and Concentrator Kit (Zymo) and stored at −20° C. until use.

The RNA guide is then labeled with 6-carboxyfluorescein (6-FAM) (IDT™). 25 nM nuclease polypeptide (wild-type or variant polypeptide) in 1× assay buffer (20 mM Tris-HCl (pH 7.5), 150 mM KCl, 5 mM $MgCl_2$, 1 mM DTT) is titrated with increasing concentrations of labeled RNA guide (7.5-250 nM). Complexes are incubated at 37° C. for 30 minutes before taking fluorescence polarization measurements using a microplate reader (Infinite® 200 Pro, Tecan).

Binary complex formation at different temperatures is also investigated. Further binding experiments as described above are performed isothermally at 25, 50, 60, and 70° C.

Formation of a binary complex upon titration of a nuclease polypeptide (wild-type or variant polypeptide) with increasing concentrations of RNA guide (or formation of a binary complex upon titration of RNA guide with increasing concentrations of a nuclease polypeptide) results in changes in fluorescence polarization signal, in millipolarization (mP) units. A binding curve is generated by plotting changes in fluorescence polarization signal over a range of RNA guide concentrations.

This Example indicates how binding affinities of nuclease polypeptides (wild-type or variant polypeptide) to RNA guides can be determined and compared.

Example 3—RNA Electrophoretic Mobility Shift Assay for Variant Binary Complex Detection This Example describes use of an RNA EMSA to determine the ability of a nuclease polypeptide (wild-type or variant) to bind to an RNA guide.

Synthetic RNA guides from IDT™ are labeled with a 5' IRDye® 800CW (also referred to as IR800 dye or IR800) using 5' EndTag Labeling Kit (Vector® Laboratories) and IRDye® 800CW Maleimide (LI-COR® Biosciences), as previously detailed in Yan et al., 2018. After labeling, the RNA guides are cleaned and concentrated via phenol chloroform extraction. Concentrations are quantified by Nanodrop™.

For RNA binding assays, nuclease polypeptides (wild-type or variant polypeptides) are diluted to 2.5 µM in 1× binding buffer (50 mM NaCl, 10 mM Tris-HCl, 10 mM $MgCl_2$, 1 mM DTT, pH 7.9. Polypeptides are then serially diluted from 2.5 µM to 37.5 µM in 1× binding buffer. The polypeptides are again diluted 1:10 in 1× binding buffer plus 50 nM IR800 labeled RNA guide and mixed thoroughly. These reactions can further include 0.5-5 µg tRNA, which serves as a competitive inhibitor to decrease nonspecific binding of polypeptide to RNA and thereby facilitate accurate specific binding determinations. Reactions are incubated at 37° C. for 1 hour. 1 µL 100× bromophenol blue is added to the reactions for dye front visualization, then the entire reaction is loaded onto a 6% DNA Retardation Gel (ThermoFisher Scientific™), which runs for 90 minutes at 80V. The gel is imaged on the Licor® Odyssey® CLx.

This assay relies on the principle that the rate at which RNA migrates through the gel is determined by its size. An RNA only sample is able to migrate a particular distance. However, if the RNA binds to a polypeptide, a band that represents a larger, less mobile RNA complex appears, which is "upshifted" on the gel.

Therefore, the intensities of two bands are measured: 1) an RNA only band and 2) a polypeptide-bound "upshifted" RNA band. If all RNA is bound to a polypeptide, only an upshifted band is observed. As the concentration of polypeptide decreases, the intensity of the upshifted band decreases, while the intensity of the RNA only band increases. In comparing RNA binding affinities for nuclease polypeptides (wild-type or variant polypeptides), a higher polypeptide/RNA affinity is characterized by more specific binding at lower concentrations of polypeptide.

This Example indicates how binding affinities of wild-type nuclease polypeptides to RNA guides and binding affinities of variant polypeptides to RNA guides can be determined and compared.

Example 4—In Vitro Cleavage Assay for Variant Binary Complexes

This Example describes methods for preparing RNPs and for determining in vitro biochemical activity of the RNPs.

Vectors encoding a wild-type or variant polypeptide are transformed into E. coli BL21 (DE3) (New England Biolabs®) and expressed under a T7 promoter. Transformed cells are initially grown overnight in 5 mL Luria Broth (TEKNOVA™)+50 µg/mL kanamycin, followed by inoculation into 1 L Terrific Broth media (TEKNOVA™)+50 µg/mL kanamycin. Cells are grown at 37° C. until an $OD_{600}$ of 0.6-0.8, then protein expression is induced with 0.5 mM IPTG. Cultures are then grown at 18° C. for an additional 14-18 hours. Cultures are harvested and pelleted via centrifugation, then resuspended in 1 mL extraction buffer per 5 g cell pellet (50 mM HEPES, pH 7.5, 500 mM NaCl, 5% glycerol, 0.5 mM TCEP). Cells are lysed via cell disruptor (Constant System Limited), then centrifuged at 20,000×g for 20 minutes at 4° C. in order to clarify the lysate. 0.2% polyethylenimine (PEI) is added to the clarified lysate and incubated at 4° C. with constant end-over-end rotation for 20 minutes. The lysate is then centrifuged again at 20,000×g for 10 minutes. The lysate is purified via ion exchange chromatography. After purification, fractions are run on SDS-PAGE gels, and fractions containing protein of the appropriate size are pooled and concentrated using 30 kD Amicon Ultra15 Centrifugal Units. Proteins are buffer exchanged into 12.5 mM HEPES pH 7.0, 120 mM NaCl, 0.5 mM TCEP, and 50% glycerol. Concentrations are then measured using the Nanodrop (ThermoFisher Scientific™), and proteins are stored at −20° C.

RNPs are prepared using a 2:1 ratio of synthetic crRNA (Integrated DNA Technologies) to protein. The RNPs are complexed for 30 minutes at 37° C. in 1×NEBuffer™ 2 (NEB2; New England Biolabs®; 50 mM NaCl, 10 mM Tris-HCl, 10 mM $MgCl_2$, 1 mM DTT, pH 7.9). After complexing, the RNPs are diluted using 1×NEB2 as a dilution buffer. Apo reactions (protein without RNA guide) are prepared in the same manner, making up the volume of crRNA with $H_2O$.

A target dsDNA substrate (Integrated DNA Technologies) is added at 20 nM to the RNP and apo samples. Reactions are mixed thoroughly then incubated at 37° C. for 1 hour, then quenched with 1 µL 20 mg/mL Proteinase K (ThermoFisher Scientific™). Reactions were incubated for another 15 minutes at 50° C., then the entire reaction was run on a 2% agarose E-gel (ThermoFisher Scientific™). Gels were visualized by ethidium bromide on a Gel Doc™ EZ Gel Imager (BioRad®).

The intensities of two types of bands are measured: 1) a full-length (uncleaved) DNA band and 2) one or more downshifted cleaved DNA bands. An inactive RNP is characterized by a full-length DNA band. An active RNP yields one or more downshifted cleaved DNA bands. As the concentration of an active RNP decreases, the intensity of the full-length band increases, and the intensity of the cleaved band(s) decreases. In comparing activity of multiple RNPs, an RNP having higher activity than another is characterized by more intense cleaved bands at lower RNP concentrations.

The method of this Example allows for the comparison of in vitro cleavage activity of wild-type or variant RNPs (binary complexes) on target DNA.

Example 5—In Vitro Stability Assays of Variant Polypeptides and Variant Binary Complexes In this Example, the stability of a variant RNP is assessed. For the accelerated stability study, RNPs (5 µM) are generated in the same manner as described in Example 4, and the samples are subsequently stored at 25° C. for 48 hours.

In vitro cleavage assays (as described in Example 4) are performed on the RNP samples. These results are compared with those of Example 4 to determine the extent to which variant RNPs stored at 25° C. for 48 hours retain biochemical activity.

Apo polypeptide (without RNA guide) is also incubated at 25° C. for 48 hours. RNA EMSA assays are performed on the apo samples using the method described in Example 3. These results are compared with those of Example 3 to determine the extent to which a variant polypeptide is able to form a binary complex with an RNA guide.

Apo samples incubated at 25° C. for 48 hours are also complexed with RNA guides to form RNPs, using the method described in Example 4. In vitro cleavage assays are then performed according to the methods of Example 4. The assay results are compared with those of Example 4 to assess activity levels of variant RNPs formed with protein incubated at 25° C.

The methods of this Example allow for comparison of the stability of wild-type and variant polypeptides and wild-type and variant RNPs (binary complexes). An nuclease polypeptide demonstrating greater specific binding to an RNA guide than another nuclease polypeptide to the RNA guide is indicative of a more stable polypeptide. An RNP demonstrating more robust in vitro cleavage of a target DNA than cleavage by another RNP is indicative of a more stable binary complex.

Example 6—DNA Electrophoretic Mobility Shift Assay for Variant Ternary Complex Detection This Example describes use of a DNA EMSA to determine the ability of an RNA guide, a nuclease polypeptide (wild-type or variant polypeptide), and a target DNA substrate to form a ternary complex.

Vectors encoding a wild-type or variant polypeptide are transformed into E. coli BL21 (DE3) (New England Biolabs®) and BL21(DE3)pLySS (Novagen®). Transformed cells are initially grown overnight in 5 mL Luria Broth (TEKNOVA™)+50 µg/mL kanamycin, followed by inoculation into 1 L Terrific Broth media (TEKNOVA™)+50 µg/mL kanamycin. Cells are grown at 37° C. until an $OD_{600}$ of 0.6-0.8, then protein expression is induced with 0.5 mM IPTG. Cultures are then grown at 18° C. for an additional 14-18 hours. Cultures are harvested and pelleted via centrifugation, then resuspended in 1 mL extraction buffer per 5 g cell pellet (50 mM HEPES, pH 7.5, 500 mM NaCl, 5% glycerol, 0.5 mM TCEP). Cells are lysed via cell disruptor (Constant System Limited), then centrifuged at 20,000×g for 20 minutes at 4° C. in order to clarify the lysate. 0.2% polyethylenimine (PEI) is added to the clarified lysate and incubated at 4° C. with constant end-over-end rotation for 20 minutes. The lysate is then centrifuged again at 20,000×g for 10 minutes. The lysate is purified via ion exchange chromatography. After purification, fractions are run on SDS-PAGE gels, and fractions containing protein of the appropriate size are pooled and concentrated using 30 kD Amicon® Ultra15 Centrifugal Units. Proteins were buffer exchanged into 12.5 mM HEPES pH 7.0, 120 mM NaCl, 0.5 mM TCEP, and 50% glycerol. Concentrations were then measured using the Nanodrop™ (ThermoFisher Scientific™) and proteins were stored at −20° C.

RNPs are prepared using a 2:1 ratio of synthetic RNA guide (Integrated DNA Technologies, IDT™) to polypeptide. Targets adjacent to the PAM sequences disclosed herein are selected, and RNA guides are designed using a direct repeat sequence as described herein. The RNPs are complexed for 30 minutes at 37° C. in 1×NEBuffer™ (NEB2; New England Biolabs®; 50 mM NaCl, 10 mM Tris-HCl, 10 mM MgCl₂, 1 mM DTT, pH 7.9). After complexing, a 5 point 1:2 serial dilution from 5 µM to 37.5 µM is performed, using 1×NEB2 as a dilution buffer. Apo reactions (polypeptide without RNA guide) are prepared in the same manner, making up the volume of RNA guide with H₂O.

dsDNA target substrates are generated by PCR from an oligo (Integrated DNA Technologies). Before PCR, the 5' end of the forward primer is labeled an IR800 dye, as described in Yan et al., 2018. Using Amplitaq Gold® (ThermoFisher Scientific™), the dsDNA substrate is then amplified with the IR800 labeled forward primer and unlabeled reverse primer. The resulting dsDNA is purified with a DNA Clean and Concentrator Kit (Zymo) and quantified by Nanodrop™ (ThermoFisher Scientific™).

RNP samples and Apo (control) samples are diluted 1:10 into 1× binding buffer (50 mM NaCl, 10 mM Tris-HCl, 1 mM TCEP, 10% glycerol, 2 mM EDTA, pH 8.0) plus 20 nM IR800 labeled target DNA substrate and mixed thoroughly. Reactions are incubated at 37° C. for 1 hour. Bromophenol blue is added to the reactions for dye front visualization, then the entire reaction is loaded onto a 6% DNA Retardation Gel (ThermoFisher Scientific™), which ran for 90 minutes at 80V. The gel is imaged on the Licor® Odyssey® CLx.

In this assay, the rate at which DNA migrates through the gel is determined by its size. A DNA only sample is able to migrate a particular distance. However, if an RNP binds to the DNA, a band that represents a larger, less mobile DNA complex appears, which is "upshifted" on the gel.

This Example shows how the affinity of variant RNPs (variant binary complexes) to DNA targets (to produce a ternary complex) can be compared to the affinity of wild-type RNPs (wild-type binary complexes to the DNA targets.

Example 7—Targeting of Mammalian Genes by Variant Polypeptides

This Example describes indel assessment on multiple targets using variants introduced into mammalian cells by transient transfection.

Variants of SEQ ID NO: 3 were cloned into a pcda3.1 backbone (Invitrogen®). RNA guides were cloned into a pUC19 backbone (New England Biolabs®). The plasmids were then maxi-prepped and diluted. The RNA guide and target sequences are shown in Table 5. The PAM sequence used was 5'-TTTG-3'.

TABLE 5

Mammalian targets and corresponding crRNAs.

| Target identifier | crRNA sequence | Target sequence |
|---|---|---|
| EMX1 | CCUGUUGUGAAUACUCUUUUAU AGGUAUCAAACAACAGCCAGUG UUGCUAGUCAAGGGCAG (SEQ ID NO: 8) | AGCCAGTGTTGCTAG TCAAGGGCAG (SEQ ID NO: 9) |
| VEGFA | CCUGUUGUGAAUACUCUUUUAU AGGUAUCAAACAACGAAAUCUA UUGAGGCUCUGGAGAGA (SEQ ID NO: 10) | GAAATCTATTGAGGC TCTGGAGAGA (SEQ ID NO: 11) |

TABLE 5-continued

Mammalian targets and corresponding crRNAs.

| Target identifier | crRNA sequence | Target sequence |
|---|---|---|
| AAVS1 | CCUGUUGUGAAUACUCUUUUAU AGGUAUCAAACAACUAGCCUC UCCCGCUCUGGUUCAGGG (SEQ ID NO: 12) | TAGCCTCTCCCGCTC TGGTTCAGGG (SEQ ID NO: 13) |

Approximately 16 hours prior to transfection, 25,000 HEK293T cells in DMEM/10% FBS+Pen/Strep (D10 media) were plated into each well of a 96-well plate. On the day of transfection, the cells were 70-90% confluent. For each well to be transfected, a mixture of Lipofectamine™ 2000 and Opti-MEM™ was prepared and incubated at room temperature for 5 minutes (Solution 1). After incubation, the Lipofectamine 2000™:Opti-MEM™ mixture was added to a separate mixture containing nuclease plasmid, RNA guide plasmid, and Opti-MEM™ (Solution 2). In the case of negative controls, the RNA guide plasmid was not included in Solution 2. Solutions 1 and 2 were mixed by pipetting up and down, then incubated at room temperature for 25 minutes. Following incubation, the Solution 1 and 2 mixture was added dropwise to each well of a 96-well plate containing the cells. Approximately 72 hours post transfection, cells were trypsinized by adding TrypLE™ to the center of each well and incubating at 37° C. for approximately 5 minutes. D10 media was then added to each well and mixed to resuspend cells. The resuspended cells were centrifuged at 500 g for 10 minutes to obtain a pellet, and the supernatant was discarded. The cell pellet was then resuspended in QuickExtract™ buffer (Lucigen®), and cells were incubated at 65° C. for 15 minutes, 68° C. for 15 minutes, and 98° C. for 10 minutes.

Samples for Next Generation Sequencing were prepared by two rounds of PCR. The first round (PCR1) was used to amplify specific genomic regions depending on the target. Round 2 PCR (PCR2) was performed to add Illumina adapters and indices. Reactions were then pooled and purified by column purification. Sequencing runs were performed using a 150 Cycle NextSeq 500/550 Mid or High Output v2.5 Kit.

Variant polypeptides comprising a single E38R, T60R, D89R, S223R, P353G, L354G, L360G, K368G, E566R, or D730R substitution relative to SEQ ID NO: 3 exhibited increased indel activity relative to the parent polypeptide of SEQ ID NO: 3. The increase in indel activity for each of the variant polypeptides was approximately 2-4-fold higher compared to indel activity by the parent polypeptide. Indel activity for variant polypeptides with D89R, L354G, K368G, or E566R substitutions is shown in FIG. 1.

Combination mutations of Table 6 were further screened in HEK293T cells. As shown in FIG. 1, each of the combination mutants exhibited higher indel activity than that of the wild-type polypeptide of SEQ ID NO: 3.

TABLE 6

Variants relative to the polypeptide of SEQ ID NO: 3.

| SEQ ID NO | Substitutions | Sequence |
|---|---|---|
| SEQ ID NO: 14 | D89R | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLEYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILD ATKKGQFNIL AELKKQNKIK IFEIEK |
| SEQ ID NO: 15 | L354G | MTTKQVKSIV LKVKNTNECP ITKDVINEYK KYYNICSEWI KDNLTSITIG DIASFLKEAT NKDTIPTYIN MGLSEEWKYK PIYHLFTDDY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLEYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYTIENEN LRKLFCGKLK VSGYNTPILD ATKKGQFNIL AELKKQNKIK IFEIEK |
| SEQ ID NO: 16 | K368G | MTTKQVKSIV LKVKNTNECP ITKDVINEYK KYYNICSEWI KDNLTSITIG DIASFLKEAT NKDTIPTYIN MGLSEEWKYK PIYHLFTDDY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQDNNQL KGYINLYGYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLEYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILD ATKKGQFNIL AELKKQNKIK IFEIEK |
| SEQ ID NO: 17 | E566R | MTTKQVKSIV LKVKNTNECP ITKDVINEYK KYYNICSEWI KDNLTSITIG DIASFLKEAT NKDTIPTYIN MGLSEEWKYK PIYHLFTDDY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQDNNQL KGYINLYKYL LEHNEFTSLL TKEELIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILD ATKKGQFNIL AELKKQNKIK IFEIEK |
| SEQ ID NO: 18 | D730R | MTTKQVKSIV LKVKNTNECP ITKDVINEYK KYYNICSEWI KDNLTSITIG DIASFLKEAT NKDTIPTYIN MGLSEEWKYK PIYHLFTDDY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILEKYYEKQ KEYDIEMGFT DDSTESKESM DKRRLEFPFR NTQIANGFLE KLSNVQQDIN GCLKNIINYA YKVFEQNGF VIALENLENS NFEKTQVLPT IKSLLEYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK EFEIEK |
| SEQ ID NO: 19 | D89R L354G | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN |

TABLE 6-continued

Variants relative to the polypeptide of SEQ ID NO: 3.

| SEQ ID NO | Substitutions | Sequence |
|---|---|---|
| | | SMTINIQDFK IENKENSLGF ILNLPLNKKK YQIELWGNRQ IKKGNKDNYK TLVDFINTYG<br>QNIIFTIKNN KIYVVFSYEC ELKEKEINFD KIVGIDVNFK HALFVASERD KNPGQDNNQL<br>KGYINLYKYL LEHNEFTSLL TKEELDIYKE IAKGVTFCPL EYNLLFTRIE NKGGKSNDKE<br>QVLSKLLYSL QIKLKNENKI QEYIYVSCVN KLRAKYVSYF ILKEKYYEKQ KEYDIEMGFT<br>DDSTESKESM DKRRLEFPFR NTQIANGFLE KLSNVQQDIN GCLKNIINYA YKVFEQNGFG<br>VIALENLENS NFEKTQVLPT IKSLLEYHKL ENQNINNINA SDKVKEYIEK EYYELTTNEN<br>NEIVDAKYTK KGIIKVKKAN FFNLMMKSLH FASNKDEFIL LSNNGKTQIA LVPSEYTSQM<br>DSIEHCLYVD KNGKKVDKKK VRQKQETHIN GLNADFNAAN NIKYIIENEN LRKLFCGKLK<br>VSGYNTPILD ATKKGQFNIL AELKKQNKIK IFEIEK |
| SEQ ID NO: 20 | D89R D730R | MTTKQVKSIV LKVKNTNECP ITKDVINEYK KYYNICSEWI KDNLTSITIG DIASFLKEAT<br>NKDTIPTYIN MGLSEEWKYK PIYHLFTDRY HEKSANNLLY AYFKEKNLDC YNGNILNLSE<br>TYYRRNGYFK SVVGNYRTKI RTLNYKIKRK NVDENSTNED IELQVMYEIA KRKLNIKKDW<br>ENYISYIENV ENINIKNIDR YNLLYKHFCE NESTINCKME LLSVEQLKEF GGCVMKQHIN<br>SMTINIQDFK IENKENSLGF ILNLPLNKKK YQIELWGNRQ IKKGNKDNYK TLVDFINTYG<br>QNIIFTIKNN KIYVVFSYEC ELKEKEINFD KIVGIDVNFK HALFVASERD KNPLQDNNQL<br>KGYINLYKYL LEHNEFTSLL TKEELDIYKE IAKGVTFCPL EYNLLFTRIE NKGGKSNDKE<br>QVLSKLLYSL QIKLKNENKI QEYIYVSCVN KLRAKYVSYF ILKEKYYEKQ KEYDIEMGFT<br>DDSTESKESM DKRRLEFPFR NTQIANGFLE KLSNVQQDIN GCLKNIINYA YKVFEQNGFG<br>VIALENLENS NFEKTQVLPT IKSLLEYHKL ENQNINNINA SDKVKEYIEK EYYELTTNEN<br>NEIVDAKYTK KGIIKVKKAN FFNLMMKSLH FASNKDEFIL LSNNGKTQIA LVPSEYTSQM<br>DSIEHCLYVD KNGKKVDKKK VRQKQETHIN GLNADFNAAN NIKYIIENEN LRKLFCGKLK<br>VSGYNTPILR ATKKGQFNIL AELKKQNKIK IFEIEK |
| SEQ ID NO: 21 | L354G K386G | MTTKQVKSIV LKVKNTNECP ITKDVINEYK KYYNICSEWI KDNLTSITIG DIASFLKEAT<br>NKDTIPTYIN MGLSEEWKYK PIYHLFTDDY HEKSANNLLY AYFKEKNLDC YNGNILNLSE<br>TYYRRNGYFK SVVGNYRTKI RTLNYKIKRK NVDENSTNED IELQVMYEIA KRKLNIKKDW<br>ENYISYIENV ENINIKNIDR YNLLYKHFCE NESTINCKME LLSVEQLKEF GGCVMKQHIN<br>SMTINIQDFK IENKENSLGF ILNLPLNKKK YQIELWGNRQ IKKGNKDNYK TLVDFINTYG<br>QNIIFTIKNN KIYVVFSYEC ELKEKEINFD KIVGIDVNFK HALFVASERD KNPGQDNNQL<br>KGYINLYGYL LEHNEFTSLL TKEELDIYKE IAKGVTFCPL EYNLLFTRIE NKGGKSNDKE<br>QVLSKLLYSL QIKLKNENKI QEYIYVSCVN KLRAKYVSYF ILKEKYYEKQ KEYDIEMGFT<br>DDSTESKESM DKRRLEFPFR NTQIANGFLE KLSNVQQDIN GCLKNIINYA YKVFEQNGFG<br>VIALENLENS NFEKTQVLPT IKSLLEYHKL ENQNINNINA SDKVKEYIEK EYYELTTNEN<br>NEIVDAKYTK KGIIKVKKAN FFNLMMKSLH FASNKDEFIL LSNNGKTQIA LVPSEYTSQM<br>DSIEHCLYVD KNGKKVDKKK VRQKQETHIN GLNADFNAAN NIKYIIENEN LRKLFCGKLK<br>VSGYNTPILD ATKKGQFNIL AELKKQNKIK IFEIEK |
| SEQ ID NO: 22 | L345G D730R | MTTKQVKSIV LKVKNTNECP ITKDVINEYK KYYNICSEWI KDNLTSITIG DIASFLKEAT<br>NKDTIPTYIN MGLSEEWKYK PTYHLFTDDY HEKSANNLLY AYFKEKNLDC YNGNILNLSE<br>TYYRRNGYFK SVVGNYRTKI RTLNYKIKRK NVDENSTNED IELQVMYEIA KRKLNIKKDW<br>ENYISYIENV ENINIKNIDR YNLLYKHFCE NESTINCKME LLSVEQLKEF GGCVMKQHIN<br>SMTINIQDFK IENKENSLGF ILNLPLNKKK YQIELWGNRQ IKKGNKDNYK TLVDFINTYG<br>QNIIFTIKNN KIYVVFSYEC ELKEKEINFD KIVGIDVNFK HALFVASERD KNPLQDNNQL<br>KGYINLYKYL LEHNEFTSLL TKEELDIYKE IAKGVTFCPL EYNLLFTRIE NKGGKSNDKE<br>QVLSKLLYSL QIKLKNENKI QEYIYVSCVN KLRAKYVSYF ILKEKYYEKQ KEYDIEMGFT<br>DDSTESKESM DKRRLEFPFR NTQIANGFLE KLSNVQQDIN GCLKNIINYA YKVFEQNGFG<br>VIALENLENS NFEKTQVLPT IKSLLEYHKL ENQNINNINA SDKVKEYIEK EYYELTTNEN<br>NEIVDAKYTK KGIIKVKKAN FFNLMMKSLH FASNKDEFIL LSNNGKTQIA LVPSEYTSQM<br>DSIEHCLYVD KNGKKVDKKK VRQKQETHIN GLNADFNAAN NIKYIIENEN LRKLFCGKLK<br>VSGYNTPILR ATKKGQFNIL AELKKQNKIK IFEIEK |
| SEQ ID NO: 23 | K368G E566R | MTTKQVKSIV LKVKNTNECP ITKDVINEYK KYYNICSEWI KDNLTSITIG DIASFLKEAT<br>NKDTIPTYIN MGLSEEWKYK PIYHLFTDDY HEKSANNLLY AYFKEKNLDC YNGNILNLSE<br>TYYRRNGYFK SVVGNYRTKI RTLNYKIKRK NVDENSTNED IELQVMYEIA KRKLNIKKDW<br>ENYISYIENV ENINIKNIDR YNLLYKHFCE NESTINCKME LLSVEQLKEF GGCVMKQHIN<br>SMTINIQDFK IENKENSLGF ILNLPLNKKK YQIELWGNRQ IKKGNKDNYK TLVDFINTYG<br>QNIIFTIKNN KIYVVFSYEC ELKEKEINFD KIVGIDVNFK HALFVASERD KNPLQDNNQL<br>KGYINLYGYL LEHNEFTSLL TKEELDIYKE IAKGVTFCPL EYNLLFTRIE NKGGKSNDKE<br>QVLSKLLYSL QIKLKNENKI QEYIYVSCVN KLRAKYVSYF ILKEKYYEKQ KEYDIEMGFT<br>DDSTESKESM DKRRLEFPFR NTQIANGFLE KLSNVQQDIN GCLKNIINYA YKVFEQNGFG<br>VIALENLENS NFEKTQVLPT IKSLLRYHKL ENQNINNINA SDKVKEYIEK EYYELTTNEN<br>NEIVDAKYTK KGIIKVKKAN FFNLMMKSLH FASNKDEFIL LSNNGKTQIA LVPSEYTSQM<br>DSIEHCLYVD KNGKKVDKKK VRQKQETHIN GLNADFNAAN NIKYIIENEN LRKLFCGKLK<br>VSGYNTPILD ATKKGQFNIL AELKKQNKIK IFEIEK |
| SEQ ID NO: 24 | K368G D730R | MTTKQVKSIV LKVKNTNECP ITKDVINEYK KYYNICSEWI KDNLTSITIG DIASFLKEAT<br>NKDTIPTYIN MGLSEEWKYK PIYHLFTDDY HEKSANNLLY AYFKEKNLDC YNGNILNLSE<br>TYYRRNGYFK SVVGNYRTKI RTLNYKIKRK NVDENSTNED IELQVMYEIA KRKLNIKKDW<br>ENYISYIENV ENINIKNIDR YNLLYKHFCE NESTINCKME LLSVEQLKEF GGCVMKQHIN<br>SMTINIQDFK IENKENSLGF ILNLPLNKKK YQIELWGNRQ IKKGNKDNYK TLVDFINTYG<br>QNIIFTIKNN KIYVVFSYEC ELKEKEINFD KIVGIDVNFK HALFVASERD KNPLQDNNQL<br>KGYINLYGYL LEHNEFTSLL TKEELDIYKE IAKGVTFCPL EYNLLFTRIE NKGGKSNDKE<br>QVLSKLLYSL QIKLKNENKI QEYIYVSCVN KLRAKYVSYF ILKEKYYEKQ KEYDIEMGFT |

TABLE 6-continued

Variants relative to the polypeptide of SEQ ID NO: 3.

| SEQ ID NO | Substitutions | Sequence |
|---|---|---|
| | | DDSTESKESM DKRRLEFPFR NTQIANGFLE KLSNVQQDIN GCLKNIINYA YKVFEQNGFG VIALENLENS NFEKTQVLPT IKSLLEYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 25 | E566R D730R | MTTKQVKSIV LKVKNTNECP ITKDVINEYK KYYNICSEWI KDNLTSITIG DIASFLKEAT NKDTIPTYIN MGLSEEWKYK PIYHLFTDDY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 26 | D89R L354G K368G | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYGYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILD ATKKGQFNIL AELKKQNKIK IFEIEK |
| SEQ ID NO: 27 | D89R L354G E566R | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILD ATKKGQFNIL AELKKQNKIK IFEIEK |
| SEQ ID NO: 28 | D89R L354G D730R | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 29 | D89R K368G E566R | MTTKQVKSIV LKVKNTNECP ITKDVINEYK KYYNICSEWI KDNLTSITIG DIASFLKEAT NKDTIPTYIN MGLSEEWKYK PTYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQDNNQL KGYINLYGYL LEHNEFTSLL TKEELDIYKE IAKGVTFCPL EYNLLFTRIE NKGGKSNDKE QVLSKLLYSL QIKLKNENKI QIYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK |

TABLE 6-continued

Variants relative to the polypeptide of SEQ ID NO: 3.

| SEQ ID NO | Substitutions | Sequence |
|---|---|---|
| | | VSGYNTPILD ATKKGQFNIL AELKKQNKIK IFEIEK |
| SEQ ID NO: 30 | D89R K368G D730R | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIRKR NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQDNNQL KGYINLYGYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLEYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 31 | D89R E566R D730R | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIRKR NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 32 | L354G K368G E566R | MTTKQVKSIV LKVKNTNECP ITKDVINEYK KYYNICSEWI KDNLTSITIG DIASFLKEAT NKDTIPTYIN MGLSEEWKYK PIYHLFTDDY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYGYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILD ATKKGQFNIL AELKKQNKIK IFEIEK |
| SEQ ID NO: 33 | L354G K368G D730R | MTTKQVKSIV LKVKNTNECP ITKDVINEYK KYYNICSEWI KDNLTSITIG DIASFLKEAT NKDTIPTYIN MGLSEEWKYK PIYHLFTDDY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYGYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLEYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 34 | L354G E566R D730R | MTTKQVKSIV LKVKNTNECP ITKDVINEYK KYYNICSEWI KDNLTSITIG DIASFLKEAT NKDTIPTYIN MGLSEEWKYK PIYHLFTDDY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| | L354G E566R | MTTKQVKSIV LKVKNTNECP ITKDVINEYK KYYNICSEWI KDNLTSITIG DIASFLKEAT NKDTIPTYIN MGLSEEWKYK PIYHLFTDDY HEKSANNLLY AYFKEKNLDC YNGNILNLSE |

TABLE 6-continued

Variants relative to the polypeptide of SEQ ID NO: 3.

| SEQ ID NO | Substitutions | Sequence |
|---|---|---|
| NO: 35 | D730R | TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 36 | D89R L354G K368G E566R | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGDNNQL KGYINLYGYL LEHNEFTSLL TKEELDIYKE IAKGVTFCPL EYNLLFRTIE NKGGKSNDKE QVLSKLLYSL QIKLKNENKI QEYIYVSCVN KLRAKYVSYF ILKEKYYEKQ KEYDIEMGFT DDSTESKESM KDRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILD ATKKGQFNIL AELKKQNKIK IFEIEK |
| SEQ ID NO: 37 | D89R L354G K368G D730R | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGDNNQL KGYINLYGYL LEHNEFTSLL TKEELDIYKE IAKGVTFCPL EYNLLFTRIE NKGGKSNDKE QVLSKLLYSL QIKLKNINKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLEYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 38 | D89R L354G E566R D730R | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGDNNQL KGYINLYKYL LEHNEFTSLL TKEELDIYKE IAKGVTFCPL EYNLLFTRIE NKGGKSNDKE QVLSKLLYSL QIKLKNINKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 39 | D89R K368G E566R D730R | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLFG ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQDNNQL KGYINLYGYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |

TABLE 6-continued

Variants relative to the polypeptide of SEQ ID NO: 3.

| SEQ ID NO | Substitutions | Sequence |
|---|---|---|
| SEQ ID NO: 40 | L354G K368G E566R D730R | MTTKQVKSIV LKVKNTNECP ITKDVINEYK KYYNICSEWI KDNLTSITIG DIASFLKEAT NKDTIPTYIN MGLSEEWKYK PIYHLFTDDY HEKSANNLLY AYFKEKNLDC YNGNILNLSE TYYRRNGYFK SVVGNYRTKI TRLNYKIKRK NVDENSTNED IELQVMYEIA KRKLNIKKDW ENYISYIENV ENINIKNIDR YNLLYKLFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYGYL LEHNEFTSLL TKEELKIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 41 | D89R L354G K368G E566R D730R | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI TRLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYGYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |

This Example shows that the polypeptide of SEQ ID NO: 3 was engineered to increase indel (e.g., nuclease) activity.

Example 8—Targeting of Mammalian Genes by Variant Polypeptides Comprising Point Mutations This Example describes indel assessment on multiple targets using variants introduced into mammalian cells by transient transfection.

Forty-five variant polypeptides, each comprising a single amino acid substitution relative to SEQ ID NO: 3, were engineered and tested for activity at the three targets listed in Table 7. The variant polypeptides were cloned into a pcDNA3.1 backbone (Invitrogen®). The RNA guides (crRNAs) of Table 7 were cloned into a pUC19 backbone (New England Biolabs®). The plasmids were then prepped, column purified, and diluted.

TABLE 7

Mammalian targets and corresponding crRNAs.

| Target identifier | crRNA sequence | Target sequence | PAM sequence |
|---|---|---|---|
| AAVS1 | CCUGUUGUGAAUACU CUUUUAUAGGUAUCA AACAACUGAGAAUGG UGCGUCCUAGG (SEQ ID NO: 42) | TGAGAATGGT GCGTCCTAGG (SEQ ID NO: 43) | 5'-TTTG-3' |
| VEGFA | CCUGUUGUGAAUACU CUUUUAUAGGUAUCA AACAACUCCAGACCA CCAAUGGGCAC (SEQ ID NO: 44) | TCCAGACCAC CAATGGGCAC (SEQ ID NO: 45) | 5'-TTTA-3' |

TABLE 7-continued

Mammalian targets and corresponding crRNAs.

| Target identifier | crRNA sequence | Target sequence | PAM sequence |
|---|---|---|---|
| EMX1 | CCUGUUGUGAAUACU CUUUUAUAGGUAUCA AACAACCCGCCGCUU CCUGAGCCAUC (SEQ ID NO: 46) | CCGCCGCTTC CTGAGCCATC (SEQ ID NO: 47) | 5'-ATTG-3' |

Approximately 16 hours prior to transfection, 25,000 HEK293T cells in DMEM/10% FBS+Pen/Strep (D10 media) were plated into each well of a 96-well plate. On the day of transfection, the cells were 70-90% confluent. For each well to be transfected, a mixture of Lipofectamine 2000™ and Opti-MEM™ was prepared and incubated at room temperature for 5 minutes (Solution 1). After incubation, the Lipofectamine 2000™:Opti-MEM™ mixture was added to a separate mixture containing nuclease plasmid, RNA guide plasmid, and Opti-MEM™ (Solution 2). In the case of negative controls, the RNA guide plasmid was not included in Solution 2. Solutions 1 and 2 were mixed by pipetting up and down, then incubated at room temperature for 25 minutes. Following incubation, the Solution 1 and 2 mixture was added dropwise to each well of a 96-well plate containing the cells. Approximately 72 hours post transfection, cells were trypsinized by adding TrypLE™ to the center of each well and incubating at 37° C. for approximately 5 minutes. D10 media was then added to each well and mixed to resuspend cells. The resuspended cells were centrifuged at 500 g for 10 minutes to obtain a pellet, and the supernatant was discarded. The cell pellet was then resuspended in QuickExtract™ buffer (Lucigen®), and cells were incubated at 65° C. for 15 minutes, 68° C. for 15 minutes, and 98° C. for 10 minutes.

Samples for Next Generation Sequencing were prepared by two rounds of PCR. The first round (PCR1) was used to amplify specific genomic regions depending on the target. Round 2 PCR (PCR2) was performed to add Illumina adapters and indices. Reactions were then pooled and purified by column purification. Sequencing runs were performed using a 150 Cycle NextSeq 500/550 Mid or High Output v2.5 Kit.

Figure 2A:
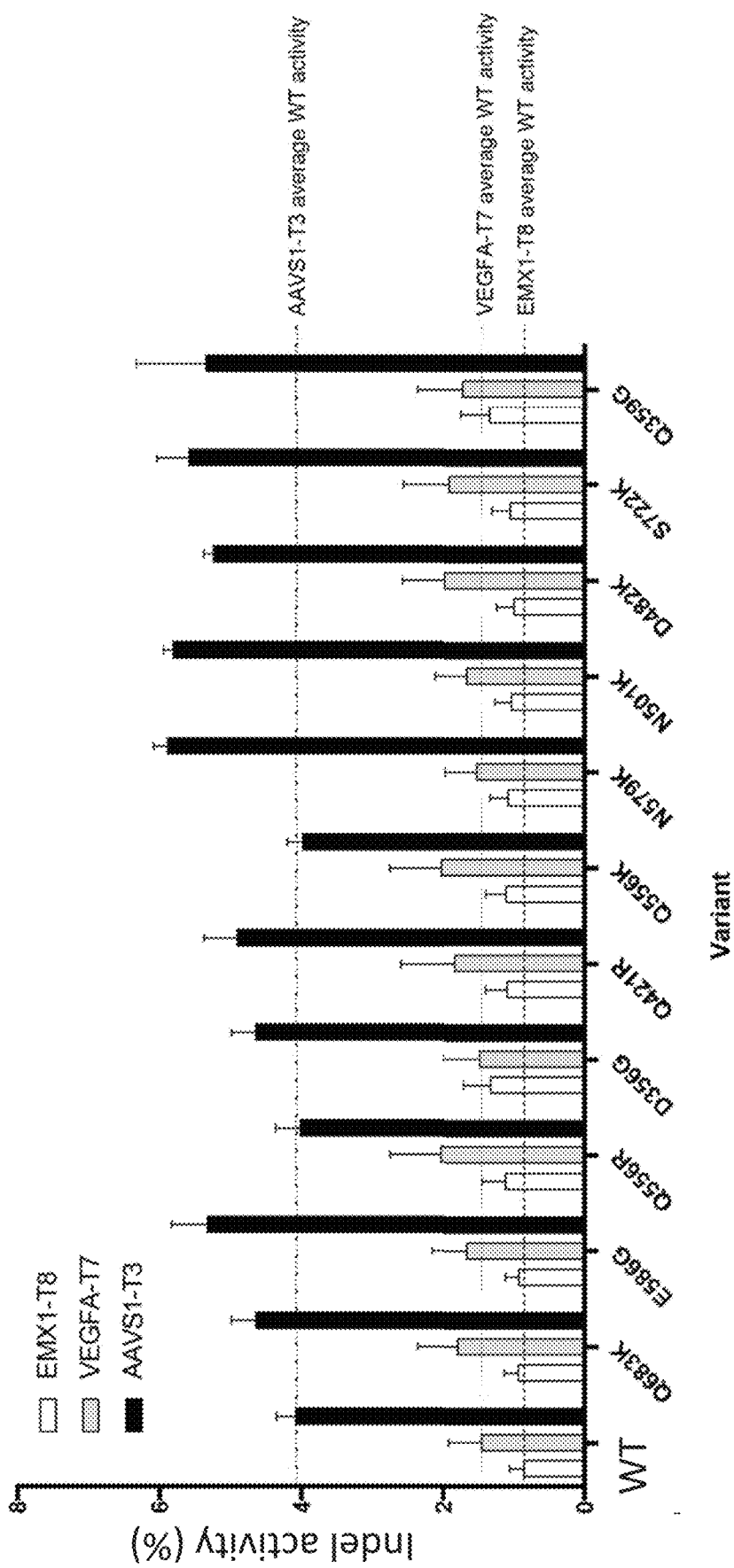
FIG. 2A and FIG. 2B show % indels induced in an AAVS1 target (SEQ ID NO: 42), EMX1 target (SEQ ID NO: 46), and a VEGFA target (SEQ ID NO: 44) by variant polypeptides having point substitutions relative to SEQ ID NO: 3. The dotted lines depict the average indel activity by the parent polypeptide of SEQ ID NO: 3 at each of the three targets. Data shown is an average of two bioreplicates of two technical replicates each.
Figure 2B:
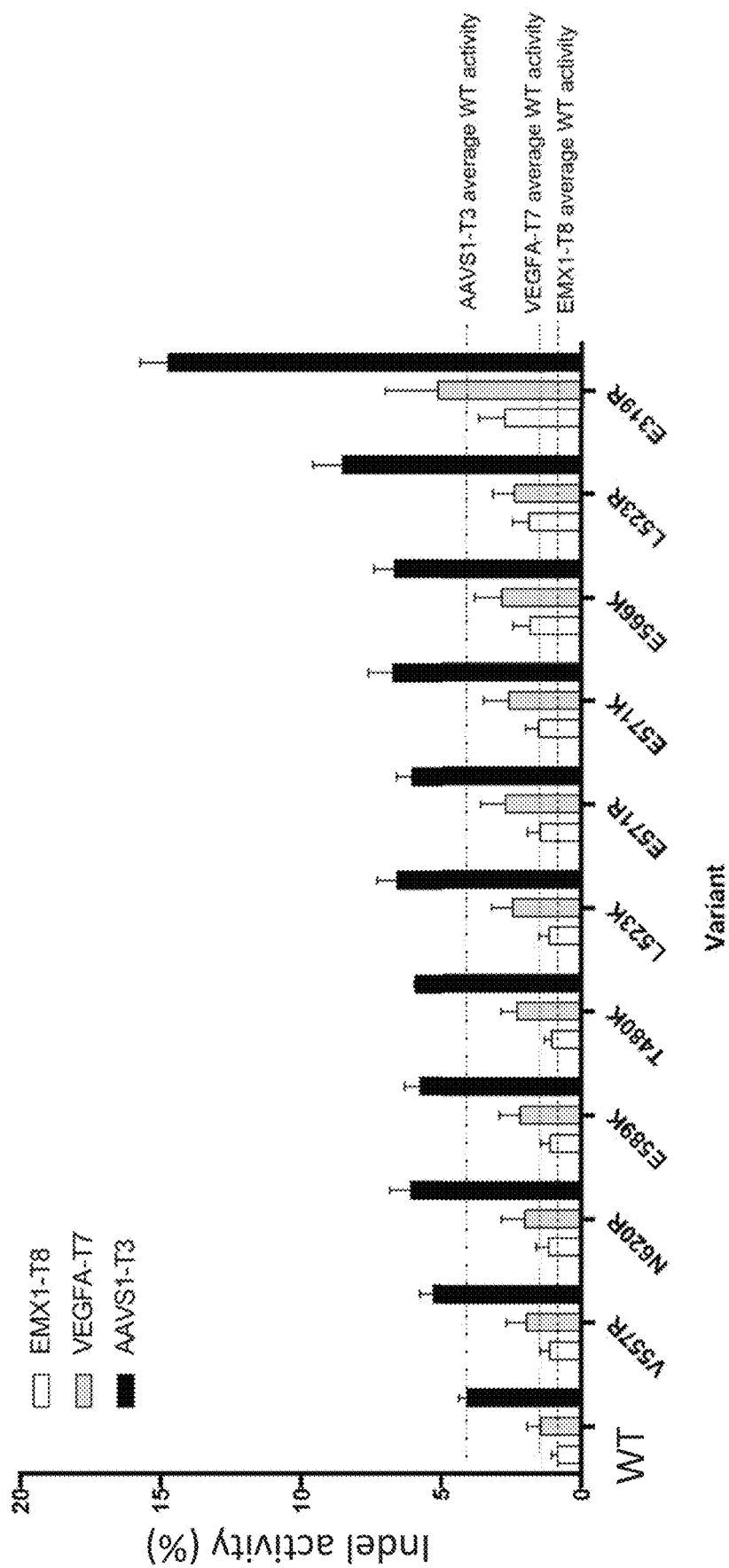

Indel activity for the variant polypeptides, calculated as the percentage of NGS reads exhibiting an indel, is shown in FIGS. 2A and 2B. The following twenty-one variants exhibited increased indel activity compared to the parent polypeptide of SEQ ID NO: 3: Q683K, E586G, Q556R, D356G, Q421R, Q556K, N579K, N501K, D482K, S722K, Q359G, V557R, N620R, E589K, T480K, L523K, E571R, E571K, E566K, L523R, and E319R. The twenty-one variants yielded increased indel activity compared to the parent polypeptide at each of the targets with the exception of Q556R and Q556K, which resulted in similar indel levels to the parent polypeptide at the AAVS 1 target. Averaging indel activity over the three targets, indel activity for each of the twenty-one variants was approximately 1.2- to 3.4-fold higher relative to that of the parent polypeptide. E319R yielded the highest increase in indel activity of all variants tested.

Example 9—Targeting of Mammalian Genes by Combinatorial Variant Polypeptides

In this Example, combinatorial variants were introduced into mammalian cells by transient transfection and assessed for indel activity on multiple targets.

Eleven combinatorial variants comprising 4 to 8 substitutions relative to SEQ ID NO: 3 were cloned into a pcDNA3.1 backbone (Invitrogen®). The substitutions introduced were associated with increased indel activity in Examples 7 and 8. The amino acid sequences are shown in Table 8. The target and RNA guide sequences are shown in Table 7. The cell transfection protocol was performed as described in Example 8.

TABLE 8

Variants relative to the polypeptide of SEQ ID NO: 3.

| SEQ ID NO | Subst. | Sequence |
|---|---|---|
| SEQ ID NO: 39 | D89R K368G E566R D730R | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQDNNQL KGYINLYGYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 49 | D89R K368G E566R D730R T60R D356G | MTTKQVKSIV LKVKNTNECP ITKDVINEYK KYYNICSEWI KDNLTSITIG DIASFLKEAR NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQGNNQL KGYINLYGYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 50 | D89R K368G E566R D730R T60R D356G P353G | MTTKQVKSIV LKVKNTNECP ITKDVINEYK KYYNICSEWI KDNLTSITIG DIASFLKEAR NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNGLQGNNQL KGYINLYGYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 51 | D89R K368G E566R D730R T60R D356G | MTTKQVKSIV LKVKNTNECP ITKDVINEYK KYYNICSEWI KDNLTSITIG DIASFLKEAR NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPLQGNNQL |

TABLE 8-continued

Variants relative to the polypeptide of SEQ ID NO: 3.

| SEQ ID NO | Subst. | Sequence |
|---|---|---|
| | E571R | KGYINLYGYL LEHNEFTSLL TKEELDIYKE IAKGVTFCPL EYNLLFTRIE NKGGDSNDKE QVLSKLLYSL QIKLKNENKI QEYIYVSCVN KLRAKYVSYF ILKEKYYEKQ KEYDIEMGFT DDSTESKESM DKRRLEFPFR NTQIANFGLE KLSNVQQDIN GCLKNIIYNA YKVFEQNGFG VIALENLENS NFEKTQVLPT IKSLLRYHKL RNQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 52 | D89R K368G E566R D730R T60R D356G P353G E571R | MTTKQVKSIV LKVKNTNECP ITKDVINEYK KYYNICSEWI KDNLTSITIG DIASFLKEAR NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNGLQGNNQL KGYINLYGYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIIYNA YKVFEQNGFG VIALENLENS NFEKTQVLPT IKSLLRYHKL RNQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 53 | D89R L354G E566R D730R T60R | MTTKQVKSIV LKVKNTNECP ITKDVINEYK KYYNICSEWI KDNLTSITIG DIASFLKEAR NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIIYNA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD NKGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 54 | D89R L354G E566R D730R D456G | MTTKQVKSIV LKVKNTNECP ITKDVINEYK KYYNICSEWI KDNLTSITIG DIASFLKEAT NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYKYL LEHNEFTSLL TKEELDIYKE IAKGVTFCPL EYNLLFTRIE NKGGKSNDKE QVLSKLLYSL QIKLKNENKI QIYIYVSCVN KLRAKYVSYF ILKEKYYEKQ KEYDIEMGFT DDSTESKESM DKRRLEFPFR NTQIANGFLE KLSNVQQDIN GCLKNIIYNA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 55 | D89R L354G E566R D730R T60R D356G | MTTKQVKSIV LKVKNTNECP ITKDVINEYK KYYNICSEWI KDNLTSITIG DIASFLKEAR NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIIYNA YKVFEQNGFG VIALENLENS NFEKTQVLPT IKSLLRYHKL ENQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 56 | D89R L354G E566R D730R T60R P353G | MTTKQVKSIV LKVKNTNECP ITKDVINEYK KYYNICSEWI KDNLTSITIG DIASFLKEAR NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNGGQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIIYNA YKVFEQNGFG VIALENLENS NFEKTQVLPT IKSLLRYHKL ENQNINNINA SDKVKEYIEK EYYELTTNEN |

TABLE 8-continued

Variants relative to the polypeptide of SEQ ID NO: 3.

| SEQ ID NO | Subst. | Sequence |
|---|---|---|
| | | NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 57 | D89R L354G E566R D730R T60R E571R | MTTKQVKSIV LKVKNTNECP ITKDVINEYK KYYNICSEWI KDNLTSITIG DIASFLKEAR NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNPGQDNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL RNQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |
| SEQ ID NO: 58 | D89R L354G E566R D730R T60R P353G D356G E571R | MTTKQVKSIV LKVKNTNECP ITKDVINEYK KYYNICSEWI KDNLTSITIG DIASFLKEAR NKDTIPTYIN MGLSEEWKYK PIYHLFTDRY HEKSANNLLY AYFKEKNLDC YNGNILNLSE TYYRRNGYFK SVVGNYRTKI RTLNYKIKRK NVDENSTNED IELQVMYEIA KRKLNIKKDW ENYISYIENV ENINIKNIDR YNLLYKHFCE NESTINCKME LLSVEQLKEF GGCVMKQHIN SMTINIQDFK IENKENSLGF ILNLPLNKKK YQIELWGNRQ IKKGNKDNYK TLVDFINTYG QNIIFTIKNN KIYVVFSYEC ELKEKEINFD KIVGIDVNFK HALFVASERD KNGGQGNNQL KGYINLYKYL LEHNEFTSLL TKEELDIYKE IAKGVTFCPL EYNLLFTRIE NKGGKSNDKE QVLSKLLYSL QIKLKNENKI QEYIYVSCVN KLRAKYVSYF ILKEKYYEKQ KEYDIEMGFT DDSTESKESM DKRRLEFPFR NTQIANGFLE KLSNVQQDIN GCLKNIINYA YKVFEQNGFG VIALENLENS NFEKTQVLPT IKSLLRYHKL RNQNINNINA SDKVKEYIEK EYYELTTNEN NEIVDAKYTK KGIIKVKKAN FFNLMMKSLH FASNKDEFIL LSNNGKTQIA LVPSEYTSQM DSIEHCLYVD KNGKKVDKKK VRQKQETHIN GLNADFNAAN NIKYIIENEN LRKLFCGKLK VSGYNTPILR ATKKGQFNIL AELKKQNKIK IFEIEK |

Figure 3:
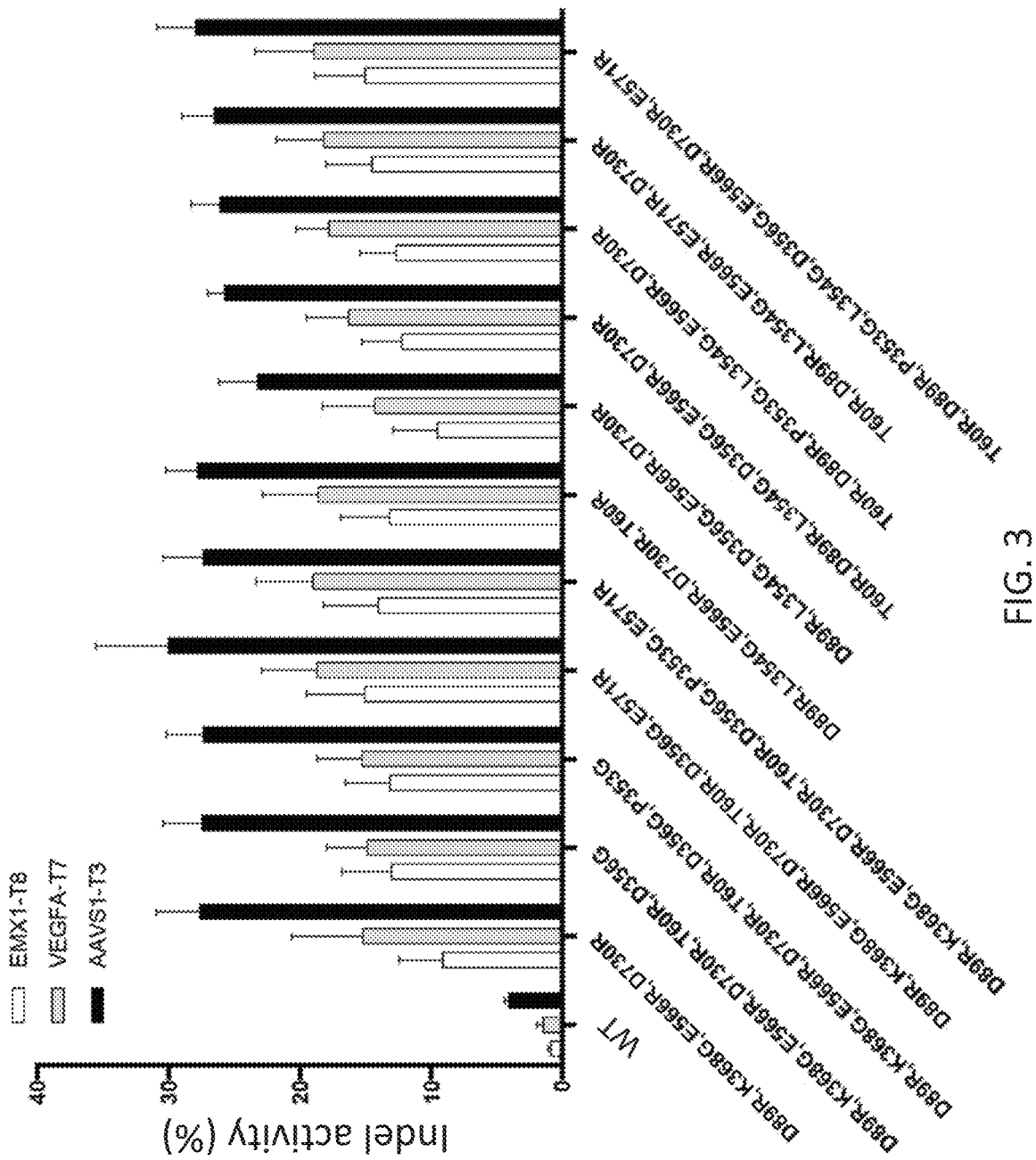
FIG. 3 shows % indels induced in an AAVS1 target (SEQ ID NO: 42), EMX1 target (SEQ ID NO: 46), and a VEGFA target (SEQ ID NO: 44) by variant polypeptides having combinatorial substitutions relative to SEQ ID NO: 3. Data shown is an average of two bioreplicates of two technical replicates each.

As shown in FIG. 3, all variants exhibited higher indel activity relative to the parent polypeptide of SEQ ID NO: 3. The indel activity for the combinatorial mutants averaged across the three targets tested was approximately 7.3- to 9.9-fold higher compared to the indel activity of the parent polypeptide. The highest performing variant tested in this Example, SEQ ID NO: 51, comprised the following seven substitutions: D89R, K368G, E566R, D730R, T60R, D356G, P353G, and E571R.

What is claimed is:

1. A variant polypeptide comprising the sequence set forth in SEQ ID NO: 51.

2. The variant polypeptide of claim 1, which further comprises a nuclear localization signal (NLS).

3. The variant polypeptide of claim 1, which further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

4. A composition comprising a variant polypeptide of claim 1, wherein the composition further comprises an RNA guide or a nucleic acid encoding the RNA guide, wherein the RNA guide comprises a direct repeat sequence and a spacer sequence.

5. The composition of claim 4, wherein the direct repeat sequence is at least 90% identical to SEQ ID NO: 4 or SEQ ID NO: 5 or comprises a sequence having at least 90% identity to SEQ ID NO: 6 or SEQ ID NO: 7.

6. The composition of claim 4, wherein the direct repeat sequence is at least 95% identical to SEQ ID NO: 4 or SEQ ID NO: 5 or comprises a sequence having at least 95% identity to SEQ ID NO: 6 or SEQ ID NO: 7.

7. The composition of claim 4, wherein the direct repeat sequence is SEQ ID NO: 4 or SEQ ID NO: 5 or comprises a sequence of SEQ NO: 6 or SEQ ID NO: 7.

8. The composition of claim 4, wherein the spacer sequence is about 15 nucleotides to about 35 nucleotides in length.

9. The composition of claim 4, wherein the spacer sequence binds to a target strand sequence of a target nucleic acid, and wherein a non-target strand sequence of the target nucleic acid sequence is adjacent to a protospacer adjacent motif (PAM) sequence.

10. The composition of claim 9, wherein the PAM sequence is 5'-NNR-3', 5'-TNR-3', 5'-NTTN-3', 5'-NTTR-3', or 5'-TTTN-3', wherein N is any nucleotide and R is A or G.

11. The composition of claim 4, wherein the composition is present in a delivery system comprising a nanoparticle, a liposome, an exosome, a microvesicle, or a gene-gun.

12. The composition of claim 11, wherein the nanoparticle comprises a lipid nanoparticle.

13. A nucleic acid molecule encoding the variant polypeptide of claim 1.

14. The nucleic acid molecule of claim 13, wherein the nucleic acid is mRNA.

15. The nucleic acid molecule of claim 13, wherein the nucleic acid is codon-optimized for expression in a cell.

16. The nucleic acid molecule of claim 13, wherein the nucleic acid encoding the variant polypeptide is operably linked to a promoter.

17. A cell comprising the variant polypeptide of claim 1.

18. The cell of claim 17, which is a mammalian cell.

19. The cell of claim 18, which is a human cell.

20. A method of making a variant binary complex, the method comprising contacting the variant polypeptide of claim 1 with an RNA guide, wherein the RNA guide comprises a direct repeat sequence and a spacer sequence.

21. A method of complexing a variant binary complex to a target nucleic acid, the method comprising contacting the variant binary complex with the target nucleic acid, wherein the variant binary complex comprises the variant polypeptide of claim 1 and an RNA guide, wherein the RNA guide comprises a direct repeat sequence and a spacer sequence.

22. A method for editing a gene in a cell, the method comprising the cell with a composition of claim 4.

23. A plurality of cells produced by the method of claim 22.

* * * * *

SEQUENCE LISTING

```
Sequence total quantity: 66
SEQ ID NO: 1              moltype = DNA   length = 1792
FEATURE                   Location/Qualifiers
misc_feature              1..1792
                          note = Description of Unknown: parent sequence
source                    1..1792
                          mol_type = other DNA
                          organism = unidentified
SEQUENCE: 1
attggtgata tcgcgagctt cctgaaagaa gcgaccaaca aggataccat cccgacctat   60
attaacatgg gcctgagcga ggaatggaag tacaaaccga tttatcacct gttcaccgac  120
gattaccacg agaagagcgc gaacaacctg ctgtacgcgt attttaagga gaaaaacctg  180
gactgctata acggtaacat cctgaacctg agcgaaacct actatcgtcg taacggttac  240
ttcaaaagcg tggttggcaa ctatcgtacc aagatccgta ccctgaacta caagattaag  300
cgtaagaacg tggacgagaa cagcaccaac gaggatatcg aactgcaggt tatgtatgaa  360
atcgcgaagc gtaagctgaa cattaagaaa gactgggaga actacatcag ctatattgag  420
aacgtgaaa  acatcaacat caagaacatc gatcgttaca acctgctgta taagcacttc  480
tgcgagaacg aaagcaccat taactgcaag atggaactgc tgagcgtgga gcaactgaaa  540
gaatttggtg gctgcgttat gaagcagcac atcaacagca tgaccatcaa cattcaagat  600
ttcaaaatcg agaacaagga aaacagcctg ggtttttatt tgaacctgcc gctgaacaag  660
aaaaagtacc agatcgagct gtggggtaac cgtcaaatta aaaagggcaa caagataac   720
tacaagaccc tggtggattt catcaacacc tatggccaga acatcatctt caccatcaag  780
aacaacaaga tctacgtggt tttcagctat gagtgcgaac tgaaggagaa ggaaatcaac  840
ttcgacaaga tcgtgggtat tgatgttaac ttcaagcacg cgctgtttgt tgcgagcgag  900
```

-continued

```
cgtgacaaaa accgctgca ggataacaac caactgaaag gctacatcaa cctgtacaag    960
tatctgctgg agcacaacga gttcaccagc ctgctgacca agaggagct ggacatctac   1020
aaagaaattg cgaagggtgt gaccttctgc ccgctggagt ataacctgct gtttacccgt   1080
atcgaaaaca aaggtggcaa gagcaacgat aaagagcagg ttctgagcaa gctgctgtac   1140
agcctgcaaa ttaaactgaa gaacgagaac aaaatccagg aatacattta tgtgagctgc   1200
gttaacaaac tgcgtgcgaa gtacgtgagc tatttcatcc tgaaagagaa gtactatgaa   1260
aaacaaaagg agtacgacat tgaaatgggc tttaccgacg atagcaccga gagcaaagaa   1320
agcatggata agcgtcgtct ggagttcccg tttcgtaaca cccagatcgc gaacggtttc   1380
ctggagaagc tgagcaacgt tcagcaagac attaacggct gcctgaaaaa catcattaac   1440
tacgcgtata aggtgttcga acaaaacggt tttggcgtta tcgcgctgga gaacctggaa   1500
aacagcaact ttgagaaaac ccaagtgctg ccgaccatta aaagcctgct ggagtaccac   1560
aagctggaaa accagaacat caacaacatt aacgcgagcg acaaagttaa ggagtatatc   1620
gagaaggaat actatgaact gaccaccaac gagaacaacg aaattgtgga tcgcgaaatac  1680
accaaaaagg gtatcattaa ggttaaaaag gcgaacttct ttaacctgat gatgaaaagc   1740
ctgcacttcg cgagcaacaa ggacgaattt atcctgctga gcaacaacgg ca            1792

SEQ ID NO: 2           moltype = DNA  length = 2268
FEATURE                Location/Qualifiers
misc_feature           1..2268
                       note = Description of Unknown: parent sequence
source                 1..2268
                       mol_type = other DNA
                       organism = unidentified
SEQUENCE: 2
atgaccacaa agcaggtgaa gagcatcgtg ctgaaggtga agaacaccaa tgagtgccca    60
atcacaaagg acgtgatcaa cgagtacaag aagtactata atatctgttc cgagtggatc   120
aaggacaacc tgacctccat cacaatcggc gatatcgcct cttttcctga ggaggccacc   180
aataaggata ccatccccac atatatcaac atggggcctgt ccgaggagtg gaagtacaag   240
cctatctatc acctgttcac agacgattac cacgagaagt ctgccaacaa tctgctgtac   300
gcctacttca aggagaagaa cctggactgc tataacgaca atatcctgaa tctgtccgga   360
acctactatc ggagaaacgg ctacttcaag tctgtggtgg gcaattatcg gaccaagatc   420
agaacactga actacaagat caagaggaag aatgtggacg agaactctac aaatgaggat   480
atcgagctgc aggtcatgta tgagatcgcc aagcgcaagc tgaacatcaa gaaggactgg   540
gagaattaca tcagctatat cgagaacgtg gagaacatca atatcaagaa catcgataag   600
tacaatctgc tgtataagca cttctgcgag aacgagaca ccatcaattg taagatggag    660
ctgctgtccg tggagcagct gaaggagttt ggcggctgcg tgatgaagca gcacatcaac   720
tctatgacaa tcaatatcca ggatttcaag atcgagaaca aggagaatag cctgggcttt   780
atcctgaacc tgccctgaa caagaagaag taccagatcg agctgtgggg caaccggcag   840
atcaagaagg gcaacaagga caattacaag accctggtgg atttcatcaa cacatatggc   900
cagaacatca tctttaccat caagaacaat aagatctacg tggtgttctc ctatgagtgt   960
gagctgaagg agaaggagat caactttgac aagatcgtgg catcgatgt gaatttcaag   1020
cacgccctgt ttgtggcctc tgagagagac aagaacccac tgcaggataa caatcagctg   1080
aagggctaca tcaacctgta caagtatctg ctggagcaca tgagttcac cagcctgctg   1140
acaaaggagg agctggacat ctacaaggag atcgccaagg cgtgaccttt ctgccccctg   1200
gagtataacc tgctgtttac aaggatcgag aacaagggcg gcaagtccaa tgataaggag   1260
caggtgctga gcaagctgct gtactccctg cagatcaagc tgaagaacga gaataagatc   1320
caggagtaca tctacgtgag ctgcgtgaat aagctgcgcg ccaagtacgt gagctatttc   1380
atcctgaagg agaagtacta tgaagcag aaggagtacg acatcgagat gggctttacc   1440
gacgatagca cagagtccaa ggagtctatg gataagaggc gcctggagtt cccttttcgg   1500
aacacccaga tcgccaatgg cttcctggag aagctgagca cgtgcagca ggacatcaat   1560
ggctgtctga gaacatcat caattacgcc tataagtgt tcgagcagaa cggctttgcg   1620
gtgatcgccc tggagaatct ggagaacagc aattttgaga gaccaggt gctgccaaca   1680
atcaagtccc tgctggagta ccacaagctg gagaaccaga atatcaacaa tatcaacgcc   1740
tctgacaagt gaaggagta tatcgagaag gagtactatg agctgaccac aaatgagaac   1800
aatgagatcg tggatgccaa gtacaccaag aagggcatca tcaaggtgaa gaaggccaac   1860
ttctttaatc tgatgatgaa gtctctgcac ttcgccagca acaaggacga gtttatcctg   1920
ctgtccaaca atggcaagac ccagatcgcc ctggtgccca gcgtacac atcccagatg   1980
gattctatcg agcactgcct gtatgtggac aagaacggca gaaggtgga taagaagaag   2040
gtgcggcaga agcaggagac ccacatcaac ggcctgaatg cgacttcaa tgccgccaac   2100
aatatcaagt acatcatcga gaacgagaat ctgagaaagc tgttttgtgg caagctgaag   2160
gtgtccggct ataacacccc tatcctggat gccacaaaga agggccagtt caacatcctg   2220
ccgagctga gaagcagaa taagatcaag atctttgaga tcgagaag               2268

SEQ ID NO: 3           moltype = AA  length = 756
FEATURE                Location/Qualifiers
REGION                 1..756
                       note = Description of Unknown: parent sequence
source                 1..756
                       mol_type = protein
                       organism = unidentified
SEQUENCE: 3
MTTKQVKSIV LKVKNTNECP ITKDVINEYK KYYNICSEWI KDNLTSITIG DIASFLKEAT    60
NKDTIPTYIN MGLSEEWKYK PIYHLFTDDY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPLQDNNQL   360
KGYINLYKYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
```

```
DDSTESKESM DKRRLEFPFR NTQIANGFLE KLSNVQQDIN GCLKNIINYA YKVFEQNGFG   540
VIALENLENS NFEKTQVLPT IKSLLEYHKL ENQNINNINA SDKVKEYIEK EYYELTTNEN   600
NEIVDAKYTK KGIIKVKKAN FFNLMMKSLH FASNKDEFIL LSNNGKTQIA LVPSEYTSQM   660
DSIEHCLYVD KNGKKVDKKK VRQKQETHIN GLNADFNAAN NIKYIIENEN LRKLFCGKLK   720
VSGYNTPILD ATKKGQFNIL AELKKQNKIK IFEIEK                             756

SEQ ID NO: 4              moltype = RNA   length = 36
FEATURE                   Location/Qualifiers
misc_feature              1..36
                          note = Description of Artificial Sequence: Synthetic
                            oligonucleotide
source                    1..36
                          mol_type = other RNA
                          organism = synthetic construct
SEQUENCE: 4
cctgttgtga atactctttt ataggtatca aacaac                              36

SEQ ID NO: 5              moltype = RNA   length = 35
FEATURE                   Location/Qualifiers
misc_feature              1..35
                          note = Description of Artificial Sequence: Synthetic
                            oligonucleotide
source                    1..35
                          mol_type = other RNA
                          organism = synthetic construct
SEQUENCE: 5
cctgttgtga atactcttta taggtatcaa acaac                               35

SEQ ID NO: 6              moltype = RNA   length = 16
FEATURE                   Location/Qualifiers
misc_feature              1..16
                          note = Description of Artificial Sequence: Synthetic
                            oligonucleotide
source                    1..16
                          mol_type = other RNA
                          organism = synthetic construct
SEQUENCE: 6
cctgttgtga atactc                                                   16

SEQ ID NO: 7              moltype = RNA   length = 18
FEATURE                   Location/Qualifiers
misc_feature              1..18
                          note = Description of Artificial Sequence: Synthetic
                            oligonucleotide
source                    1..18
                          mol_type = other RNA
                          organism = synthetic construct
SEQUENCE: 7
ttataggtat caaacaac                                                 18

SEQ ID NO: 8              moltype = RNA   length = 61
FEATURE                   Location/Qualifiers
misc_feature              1..61
                          note = Description of Artificial Sequence: Synthetic
                            oligonucleotide
source                    1..61
                          mol_type = other RNA
                          organism = synthetic construct
SEQUENCE: 8
cctgttgtga atactctttt ataggtatca aacaacagcc agtgttgcta gtcaagggca   60
g                                                                   61

SEQ ID NO: 9              moltype = DNA   length = 25
FEATURE                   Location/Qualifiers
misc_feature              1..25
                          note = Description of Unknown: EMX1 mammalian target
                            sequence
source                    1..25
                          mol_type = genomic DNA
                          organism = unidentified
SEQUENCE: 9
agccagtgtt gctagtcaag ggcag                                         25

SEQ ID NO: 10             moltype = RNA   length = 61
FEATURE                   Location/Qualifiers
misc_feature              1..61
                          note = Description of Artificial Sequence: Synthetic
                            oligonucleotide
source                    1..61
```

```
                         mol_type = other RNA
                         organism = synthetic construct
SEQUENCE: 10
cctgttgtga atactctttt ataggtatca aacaacgaaa tctattgagg ctctggagag    60
a                                                                    61

SEQ ID NO: 11           moltype = DNA  length = 25
FEATURE                 Location/Qualifiers
misc_feature            1..25
                        note = Description of Unknown: VEGFA mammalian target
                          sequence
source                  1..25
                        mol_type = genomic DNA
                        organism = unidentified
SEQUENCE: 11
gaaatctatt gaggctctgg agaga                                          25

SEQ ID NO: 12           moltype = RNA  length = 61
FEATURE                 Location/Qualifiers
misc_feature            1..61
                        note = Description of Artificial Sequence: Synthetic
                          oligonucleotide
source                  1..61
                        mol_type = other RNA
                        organism = synthetic construct
SEQUENCE: 12
cctgttgtga atactctttt ataggtatca aacaactagc ctctcccgct ctggttcagg    60
g                                                                    61

SEQ ID NO: 13           moltype = DNA  length = 25
FEATURE                 Location/Qualifiers
misc_feature            1..25
                        note = Description of Unknown: AAVS1 mammalian target
                          sequence
source                  1..25
                        mol_type = genomic DNA
                        organism = unidentified
SEQUENCE: 13
tagcctctcc cgctctggtt caggg                                          25

SEQ ID NO: 14           moltype = AA  length = 756
FEATURE                 Location/Qualifiers
REGION                  1..756
                        note = Description of Artificial Sequence: Synthetic
                          polypeptide
source                  1..756
                        mol_type = protein
                        organism = synthetic construct
SEQUENCE: 14
MTTKQVKSIV LKVKNTNECP ITKDVINEYK KYYNICSEWI KDNLTSITIG DIASFLKEAT    60
NKDTIPTYIN MGLSEEWKYK PIYHLFTDRY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPLQDNNQL   360
KGYINLYKYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
DDSTESKESM DKRRLEFPFR NTQIANGFLE KLSNVQQDIN GCLKNIINYA YKVFEQNGFG   540
VIALENLENS NFEKTQVLPT IKSLLEYHKL ENQNINNINA SDKVKEYIEK EYYELTTNEN   600
NEIVDAKYTK KGIIKVKKAN FFNLMMKSLH FASNKDEFIL LSNNGKTQIA LVPSEYTSQM   660
DSIEHCLYVD KNGKKVDKKK VRQKQETHIN GLNADFNAAN NIKYIIENEN LRKLFCGKLK   720
VSGYNTPILD ATKKGQFNIL AELKKQNKIK IFEIEK                             756

SEQ ID NO: 15           moltype = AA  length = 756
FEATURE                 Location/Qualifiers
REGION                  1..756
                        note = Description of Artificial Sequence: Synthetic
                          polypeptide
source                  1..756
                        mol_type = protein
                        organism = synthetic construct
SEQUENCE: 15
MTTKQVKSIV LKVKNTNECP ITKDVINEYK KYYNICSEWI KDNLTSITIG DIASFLKEAT    60
NKDTIPTYIN MGLSEEWKYK PIYHLFTDDY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPGQDNNQL   360
KGYINLYKYL LEHNEFTSLL TKEELDIYKE IAKGVTFCPL EYNLLFTRIE NKGGKSNDKE   420
```

```
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIIYNA YKVFEQNGFG    540
VIALENLENS NFEKTQVLPT IKSLLEYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILD ATKKGQFNIL AELKKQNKIK IFEIEK                              756

SEQ ID NO: 16           moltype = AA  length = 756
FEATURE                 Location/Qualifiers
REGION                  1..756
                        note = Description of Artificial Sequence: Synthetic
                        polypeptide
source                  1..756
                        mol_type = protein
                        organism = synthetic construct
SEQUENCE: 16
MTTKQVKSIV LKVKNTNECP ITKDVINEYK KYYNICSEWI KDNLTSITIG DIASFLKEAT     60
NKDTIPTYIN MGLSEEWKYK PIYHLFTDDY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPLQDNNQL    360
KGYINLYGYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIIYNA YKVFEQNGFG    540
VIALENLENS NFEKTQVLPT IKSLLEYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILD ATKKGQFNIL AELKKQNKIK IFEIEK                              756

SEQ ID NO: 17           moltype = AA  length = 756
FEATURE                 Location/Qualifiers
REGION                  1..756
                        note = Description of Artificial Sequence: Synthetic
                        polypeptide
source                  1..756
                        mol_type = protein
                        organism = synthetic construct
SEQUENCE: 17
MTTKQVKSIV LKVKNTNECP ITKDVINEYK KYYNICSEWI KDNLTSITIG DIASFLKEAT     60
NKDTIPTYIN MGLSEEWKYK PIYHLFTDDY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPLQDNNQL    360
KGYINLYKYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIIYNA YKVFEQNGFG    540
VIALENLENS NFEKTQVLPT IKSLLRYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILD ATKKGQFNIL AELKKQNKIK IFEIEK                              756

SEQ ID NO: 18           moltype = AA  length = 756
FEATURE                 Location/Qualifiers
REGION                  1..756
                        note = Description of Artificial Sequence: Synthetic
                        polypeptide
source                  1..756
                        mol_type = protein
                        organism = synthetic construct
SEQUENCE: 18
MTTKQVKSIV LKVKNTNECP ITKDVINEYK KYYNICSEWI KDNLTSITIG DIASFLKEAT     60
NKDTIPTYIN MGLSEEWKYK PIYHLFTDDY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPLQDNNQL    360
KGYINLYKYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIIYNA YKVFEQNGFG    540
VIALENLENS NFEKTQVLPT IKSLLEYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILR ATKKGQFNIL AELKKQNKIK IFEIEK                              756

SEQ ID NO: 19           moltype = AA  length = 756
FEATURE                 Location/Qualifiers
REGION                  1..756
```

```
                        note = Description of Artificial Sequence: Synthetic
                        polypeptide
source                  1..756
                        mol_type = protein
                        organism = synthetic construct
SEQUENCE: 19
MTTKQVKSIV LKVKNTNECP ITKDVINEYK KYYNICSEWI KDNLTSITIG DIASFLKEAT    60
NKDTIPTYIN MGLSEEWKYK PIYHLFTDRY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPGQDNNQL   360
KGYINLYKYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
DDSTESKESM DKRRLEFPFR NTQIANGFLE KLSNVQQDIN GCLKNIINYA YKVFEQNGFG   540
VIALENLENS NFEKTQVLPT IKSLLEYHKL ENQNINNINA SDKVKEYIEK EYYELTTNEN   600
NEIVDAKYTK KGIIKVKKAN FFNLMMKSLH FASNKDEFIL LSNNGKTQIA LVPSEYTSQM   660
DSIEHCLYVD KNGKKVDKKK VRQKQETHIN GLNADFNAAN NIKYIIENEN LRKLFCGKLK   720
VSGYNTPILD ATKKGQFNIL AELKKQNKIK IFEIEK                             756

SEQ ID NO: 20           moltype = AA  length = 756
FEATURE                 Location/Qualifiers
REGION                  1..756
                        note = Description of Artificial Sequence: Synthetic
                        polypeptide
source                  1..756
                        mol_type = protein
                        organism = synthetic construct
SEQUENCE: 20
MTTKQVKSIV LKVKNTNECP ITKDVINEYK KYYNICSEWI KDNLTSITIG DIASFLKEAT    60
NKDTIPTYIN MGLSEEWKYK PIYHLFTDRY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPLQDNNQL   360
KGYINLYKYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
DDSTESKESM DKRRLEFPFR NTQIANGFLE KLSNVQQDIN GCLKNIINYA YKVFEQNGFG   540
VIALENLENS NFEKTQVLPT IKSLLEYHKL ENQNINNINA SDKVKEYIEK EYYELTTNEN   600
NEIVDAKYTK KGIIKVKKAN FFNLMMKSLH FASNKDEFIL LSNNGKTQIA LVPSEYTSQM   660
DSIEHCLYVD KNGKKVDKKK VRQKQETHIN GLNADFNAAN NIKYIIENEN LRKLFCGKLK   720
VSGYNTPILR ATKKGQFNIL AELKKQNKIK IFEIEK                             756

SEQ ID NO: 21           moltype = AA  length = 756
FEATURE                 Location/Qualifiers
REGION                  1..756
                        note = Description of Artificial Sequence: Synthetic
                        polypeptide
source                  1..756
                        mol_type = protein
                        organism = synthetic construct
SEQUENCE: 21
MTTKQVKSIV LKVKNTNECP ITKDVINEYK KYYNICSEWI KDNLTSITIG DIASFLKEAT    60
NKDTIPTYIN MGLSEEWKYK PIYHLFTDDY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPGQDNNQL   360
KGYINLYGYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
DDSTESKESM DKRRLEFPFR NTQIANGFLE KLSNVQQDIN GCLKNIINYA YKVFEQNGFG   540
VIALENLENS NFEKTQVLPT IKSLLEYHKL ENQNINNINA SDKVKEYIEK EYYELTTNEN   600
NEIVDAKYTK KGIIKVKKAN FFNLMMKSLH FASNKDEFIL LSNNGKTQIA LVPSEYTSQM   660
DSIEHCLYVD KNGKKVDKKK VRQKQETHIN GLNADFNAAN NIKYIIENEN LRKLFCGKLK   720
VSGYNTPILD ATKKGQFNIL AELKKQNKIK IFEIEK                             756

SEQ ID NO: 22           moltype = AA  length = 756
FEATURE                 Location/Qualifiers
REGION                  1..756
                        note = Description of Artificial Sequence: Synthetic
                        polypeptide
source                  1..756
                        mol_type = protein
                        organism = synthetic construct
SEQUENCE: 22
MTTKQVKSIV LKVKNTNECP ITKDVINEYK KYYNICSEWI KDNLTSITIG DIASFLKEAT    60
NKDTIPTYIN MGLSEEWKYK PIYHLFTDDY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
```

```
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPGQDNNQL    360
KGYINLYKYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIINYA YKVFEQNGFG    540
VIALENLENS NFEKTQVLPT IKSLLEYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILR ATKKGQFNIL AELKKQNKIK IFEIEK                             756

SEQ ID NO: 23          moltype = AA  length = 756
FEATURE                Location/Qualifiers
REGION                 1..756
                       note = Description of Artificial Sequence: Synthetic
                        polypeptide
source                 1..756
                       mol_type = protein
                       organism = synthetic construct
SEQUENCE: 23
MTTKQVKSIV LKVKNTNECP ITKDVINEYK KYYNICSEWI KDNLTSITIG DIASFLKEAT     60
NKDTIPTYIN MGLSEEWKYK PIYHLFTDDY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPLQDNNQL    360
KGYINLYGYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIINYA YKVFEQNGFG    540
VIALENLENS NFEKTQVLPT IKSLLRYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILD ATKKGQFNIL AELKKQNKIK IFEIEK                             756

SEQ ID NO: 24          moltype = AA  length = 756
FEATURE                Location/Qualifiers
REGION                 1..756
                       note = Description of Artificial Sequence: Synthetic
                        polypeptide
source                 1..756
                       mol_type = protein
                       organism = synthetic construct
SEQUENCE: 24
MTTKQVKSIV LKVKNTNECP ITKDVINEYK KYYNICSEWI KDNLTSITIG DIASFLKEAT     60
NKDTIPTYIN MGLSEEWKYK PIYHLFTDDY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPLQDNNQL    360
KGYINLYGYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIINYA YKVFEQNGFG    540
VIALENLENS NFEKTQVLPT IKSLLEYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILR ATKKGQFNIL AELKKQNKIK IFEIEK                             756

SEQ ID NO: 25          moltype = AA  length = 756
FEATURE                Location/Qualifiers
REGION                 1..756
                       note = Description of Artificial Sequence: Synthetic
                        polypeptide
source                 1..756
                       mol_type = protein
                       organism = synthetic construct
SEQUENCE: 25
MTTKQVKSIV LKVKNTNECP ITKDVINEYK KYYNICSEWI KDNLTSITIG DIASFLKEAT     60
NKDTIPTYIN MGLSEEWKYK PIYHLFTDDY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPLQDNNQL    360
KGYINLYKYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIINYA YKVFEQNGFG    540
VIALENLENS NFEKTQVLPT IKSLLRYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILR ATKKGQFNIL AELKKQNKIK IFEIEK                             756
```

| SEQ ID NO: 26 | moltype = AA  length = 756 |
| --- | --- |
| FEATURE | Location/Qualifiers |
| REGION | 1..756 |
| | note = Description of Artificial Sequence: Synthetic polypeptide |
| source | 1..756 |
| | mol_type = protein |
| | organism = synthetic construct |

SEQUENCE: 26

```
MTTKQVKSIV LKVKNTNECP ITKDVINEYK KYYNICSEWI KDNLTSITIG DIASFLKEAT   60
NKDTIPTYIN MGLSEEWKYK PIYHLFTDRY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNPGQDNNQL  360
KGYINLYGYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIIYNA YKVFEQNGFG  540
VIALENLENS NFEKTQVLPT IKSLLEYHKL ENQNINNINA SDKVKEYIEK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILD ATKKGQFNIL AELKKQNKIK IFEIEK                           756
```

| SEQ ID NO: 27 | moltype = AA  length = 756 |
| --- | --- |
| FEATURE | Location/Qualifiers |
| REGION | 1..756 |
| | note = Description of Artificial Sequence: Synthetic polypeptide |
| source | 1..756 |
| | mol_type = protein |
| | organism = synthetic construct |

SEQUENCE: 27

```
MTTKQVKSIV LKVKNTNECP ITKDVINEYK KYYNICSEWI KDNLTSITIG DIASFLKEAT   60
NKDTIPTYIN MGLSEEWKYK PIYHLFTDRY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNPGQDNNQL  360
KGYINLYKYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIIYNA YKVFEQNGFG  540
VIALENLENS NFEKTQVLPT IKSLLRYHKL ENQNINNINA SDKVKEYIEK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILD ATKKGQFNIL AELKKQNKIK IFEIEK                           756
```

| SEQ ID NO: 28 | moltype = AA  length = 756 |
| --- | --- |
| FEATURE | Location/Qualifiers |
| REGION | 1..756 |
| | note = Description of Artificial Sequence: Synthetic polypeptide |
| source | 1..756 |
| | mol_type = protein |
| | organism = synthetic construct |

SEQUENCE: 28

```
MTTKQVKSIV LKVKNTNECP ITKDVINEYK KYYNICSEWI KDNLTSITIG DIASFLKEAT   60
NKDTIPTYIN MGLSEEWKYK PIYHLFTDRY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNPGQDNNQL  360
KGYINLYKYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIIYNA YKVFEQNGFG  540
VIALENLENS NFEKTQVLPT IKSLLEYHKL ENQNINNINA SDKVKEYIEK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILR ATKKGQFNIL AELKKQNKIK IFEIEK                           756
```

| SEQ ID NO: 29 | moltype = AA  length = 756 |
| --- | --- |
| FEATURE | Location/Qualifiers |
| REGION | 1..756 |
| | note = Description of Artificial Sequence: Synthetic polypeptide |
| source | 1..756 |
| | mol_type = protein |
| | organism = synthetic construct |

SEQUENCE: 29

```
MTTKQVKSIV LKVKNTNECP ITKDVINEYK KYYNICSEWI KDNLTSITIG DIASFLKEAT   60
```

```
NKDTIPTYIN MGLSEEWKYK PIYHLFTDRY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPLQDNNQL   360
KGYINLYGYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
DDSTESKESM DKRRLEFPFR NTQIANGFLE KLSNVQQDIN GCLKNIIINYA YKVFEQNGFG   540
VIALENLENS NFEKTQVLPT IKSLLRYHKL ENQNINNINA SDVKEYIEK EYYELTTNEN    600
NEIVDAKYTK KGIIKVKKAN FFNLMMKSLH FASNKDEFIL LSNNGKTQIA LVPSEYTSQM   660
DSIEHCLYVD KNGKKVDKKK VRQKQETHIN GLNADFNAAN NIKYIIENEN LRKLFCGKLK   720
VSGYNTPILD ATKKGQFNIL AELKKQNKIK IFEIEK                              756

SEQ ID NO: 30          moltype = AA   length = 756
FEATURE                Location/Qualifiers
REGION                 1..756
                       note = Description of Artificial Sequence: Synthetic
                       polypeptide
source                 1..756
                       mol_type = protein
                       organism = synthetic construct
SEQUENCE: 30
MTTKQVKSIV LKVKNTNECP ITKDVINEYK KYYNICSEWI KDNLTSITIG DIASFLKEAT    60
NKDTIPTYIN MGLSEEWKYK PIYHLFTDRY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPLQDNNQL   360
KGYINLYGYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
DDSTESKESM DKRRLEFPFR NTQIANGFLE KLSNVQQDIN GCLKNIIINYA YKVFEQNGFG   540
VIALENLENS NFEKTQVLPT IKSLLEYHKL ENQNINNINA SDVKEYIEK EYYELTTNEN    600
NEIVDAKYTK KGIIKVKKAN FFNLMMKSLH FASNKDEFIL LSNNGKTQIA LVPSEYTSQM   660
DSIEHCLYVD KNGKKVDKKK VRQKQETHIN GLNADFNAAN NIKYIIENEN LRKLFCGKLK   720
VSGYNTPILR ATKKGQFNIL AELKKQNKIK IFEIEK                              756

SEQ ID NO: 31          moltype = AA   length = 756
FEATURE                Location/Qualifiers
REGION                 1..756
                       note = Description of Artificial Sequence: Synthetic
                       polypeptide
source                 1..756
                       mol_type = protein
                       organism = synthetic construct
SEQUENCE: 31
MTTKQVKSIV LKVKNTNECP ITKDVINEYK KYYNICSEWI KDNLTSITIG DIASFLKEAT    60
NKDTIPTYIN MGLSEEWKYK PIYHLFTDRY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPLQDNNQL   360
KGYINLYKYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
DDSTESKESM DKRRLEFPFR NTQIANGFLE KLSNVQQDIN GCLKNIIINYA YKVFEQNGFG   540
VIALENLENS NFEKTQVLPT IKSLLRYHKL ENQNINNINA SDVKEYIEK EYYELTTNEN    600
NEIVDAKYTK KGIIKVKKAN FFNLMMKSLH FASNKDEFIL LSNNGKTQIA LVPSEYTSQM   660
DSIEHCLYVD KNGKKVDKKK VRQKQETHIN GLNADFNAAN NIKYIIENEN LRKLFCGKLK   720
VSGYNTPILR ATKKGQFNIL AELKKQNKIK IFEIEK                              756

SEQ ID NO: 32          moltype = AA   length = 756
FEATURE                Location/Qualifiers
REGION                 1..756
                       note = Description of Artificial Sequence: Synthetic
                       polypeptide
source                 1..756
                       mol_type = protein
                       organism = synthetic construct
SEQUENCE: 32
MTTKQVKSIV LKVKNTNECP ITKDVINEYK KYYNICSEWI KDNLTSITIG DIASFLKEAT    60
NKDTIPTYIN MGLSEEWKYK PIYHLFTDDY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPGQDNNQL   360
KGYINLYGYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
DDSTESKESM DKRRLEFPFR NTQIANGFLE KLSNVQQDIN GCLKNIIINYA YKVFEQNGFG   540
VIALENLENS NFEKTQVLPT IKSLLRYHKL ENQNINNINA SDVKEYIEK EYYELTTNEN    600
NEIVDAKYTK KGIIKVKKAN FFNLMMKSLH FASNKDEFIL LSNNGKTQIA LVPSEYTSQM   660
```

```
DSIEHCLYVD KNGKKVDKKK VRQKQETHIN GLNADFNAAN NIKYIIENEN LRKLFCGKLK  720
VSGYNTPILD ATKKGQFNIL AELKKQNKIK IFEIEK                            756

SEQ ID NO: 33            moltype = AA  length = 756
FEATURE                  Location/Qualifiers
REGION                   1..756
                         note = Description of Artificial Sequence: Synthetic
                           polypeptide
source                   1..756
                         mol_type = protein
                         organism = synthetic construct
SEQUENCE: 33
MTTKQVKSIV LKVKNTNECP ITKDVINEYK KYYNICSEWI KDNLTSITIG DIASFLKEAT   60
NKDTIPTYIN MGLSEEWKYK PIYHLFTDDY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNPGQDNNQL  360
KGYINLYGYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIINYA YKVFEQNGFG  540
VIALENLENS NFEKTQVLPT IKSLLEYHKL ENQNINNINA SDKVKEYEIK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILR ATKKGQFNIL AELKKQNKIK IFEIEK                            756

SEQ ID NO: 34            moltype = AA  length = 756
FEATURE                  Location/Qualifiers
REGION                   1..756
                         note = Description of Artificial Sequence: Synthetic
                           polypeptide
source                   1..756
                         mol_type = protein
                         organism = synthetic construct
SEQUENCE: 34
MTTKQVKSIV LKVKNTNECP ITKDVINEYK KYYNICSEWI KDNLTSITIG DIASFLKEAT   60
NKDTIPTYIN MGLSEEWKYK PIYHLFTDDY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNPGQDNNQL  360
KGYINLYKYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIINYA YKVFEQNGFG  540
VIALENLENS NFEKTQVLPT IKSLLRYHKL ENQNINNINA SDKVKEYEIK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILR ATKKGQFNIL AELKKQNKIK IFEIEK                            756

SEQ ID NO: 35            moltype = AA  length = 756
FEATURE                  Location/Qualifiers
REGION                   1..756
                         note = Description of Artificial Sequence: Synthetic
                           polypeptide
source                   1..756
                         mol_type = protein
                         organism = synthetic construct
SEQUENCE: 35
MTTKQVKSIV LKVKNTNECP ITKDVINEYK KYYNICSEWI KDNLTSITIG DIASFLKEAT   60
NKDTIPTYIN MGLSEEWKYK PIYHLFTDDY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNPGQDNNQL  360
KGYINLYKYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIINYA YKVFEQNGFG  540
VIALENLENS NFEKTQVLPT IKSLLRYHKL ENQNINNINA SDKVKEYEIK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILR ATKKGQFNIL AELKKQNKIK IFEIEK                            756

SEQ ID NO: 36            moltype = AA  length = 756
FEATURE                  Location/Qualifiers
REGION                   1..756
                         note = Description of Artificial Sequence: Synthetic
                           polypeptide
source                   1..756
                         mol_type = protein
```

```
                        organism = synthetic construct
SEQUENCE: 36
MTTKQVKSIV LKVKNTNECP ITKDVINEYK KYYNICSEWI KDNLTSITIG DIASFLKEAT    60
NKDTIPTYIN MGLSEEWKYK PIYHLFTDRY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPGQDNNQL   360
KGYINLYGYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
DDSTESKESM DKRRLEFPFR NTQIANGFLE KLSNVQQDIN GCLKNIINYA YKVFEQNGFG   540
VIALENLENS NFEKTQVLPT IKSLLRYHKL ENQNINNINA SDKVKEYIEK EYYELTTNEN   600
NEIVDAKYTK KGIIKVKKAN FFNLMMKSLH FASNKDEFIL LSNNGKTQIA LVPSEYTSQM   660
DSIEHCLYVD KNGKKVDKKK VRQKQETHIN GLNADFNAAN NIKYIIENEN LRKLFCGKLK   720
VSGYNTPILD ATKKGQFNIL AELKKQNKIK IFEIEK                            756

SEQ ID NO: 37            moltype = AA  length = 756
FEATURE                  Location/Qualifiers
REGION                   1..756
                         note = Description of Artificial Sequence: Synthetic
                         polypeptide
source                   1..756
                         mol_type = protein
                         organism = synthetic construct
SEQUENCE: 37
MTTKQVKSIV LKVKNTNECP ITKDVINEYK KYYNICSEWI KDNLTSITIG DIASFLKEAT    60
NKDTIPTYIN MGLSEEWKYK PIYHLFTDRY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPGQDNNQL   360
KGYINLYGYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
DDSTESKESM DKRRLEFPFR NTQIANGFLE KLSNVQQDIN GCLKNIINYA YKVFEQNGFG   540
VIALENLENS NFEKTQVLPT IKSLLEYHKL ENQNINNINA SDKVKEYIEK EYYELTTNEN   600
NEIVDAKYTK KGIIKVKKAN FFNLMMKSLH FASNKDEFIL LSNNGKTQIA LVPSEYTSQM   660
DSIEHCLYVD KNGKKVDKKK VRQKQETHIN GLNADFNAAN NIKYIIENEN LRKLFCGKLK   720
VSGYNTPILR ATKKGQFNIL AELKKQNKIK IFEIEK                            756

SEQ ID NO: 38            moltype = AA  length = 756
FEATURE                  Location/Qualifiers
REGION                   1..756
                         note = Description of Artificial Sequence: Synthetic
                         polypeptide
source                   1..756
                         mol_type = protein
                         organism = synthetic construct
SEQUENCE: 38
MTTKQVKSIV LKVKNTNECP ITKDVINEYK KYYNICSEWI KDNLTSITIG DIASFLKEAT    60
NKDTIPTYIN MGLSEEWKYK PIYHLFTDRY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPGQDNNQL   360
KGYINLYKYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
DDSTESKESM DKRRLEFPFR NTQIANGFLE KLSNVQQDIN GCLKNIINYA YKVFEQNGFG   540
VIALENLENS NFEKTQVLPT IKSLLRYHKL ENQNINNINA SDKVKEYIEK EYYELTTNEN   600
NEIVDAKYTK KGIIKVKKAN FFNLMMKSLH FASNKDEFIL LSNNGKTQIA LVPSEYTSQM   660
DSIEHCLYVD KNGKKVDKKK VRQKQETHIN GLNADFNAAN NIKYIIENEN LRKLFCGKLK   720
VSGYNTPILR ATKKGQFNIL AELKKQNKIK IFEIEK                            756

SEQ ID NO: 39            moltype = AA  length = 756
FEATURE                  Location/Qualifiers
REGION                   1..756
                         note = Description of Artificial Sequence: Synthetic
                         polypeptide
source                   1..756
                         mol_type = protein
                         organism = synthetic construct
SEQUENCE: 39
MTTKQVKSIV LKVKNTNECP ITKDVINEYK KYYNICSEWI KDNLTSITIG DIASFLKEAT    60
NKDTIPTYIN MGLSEEWKYK PIYHLFTDRY HEKSANNLLY AYFKEKNLDC YNGNILNLSE   120
TYYRRNGYFK SVVGNYRTKI RTLNYKIKRK NVDENSTNED IELQVMYEIA KRKLNIKKDW   180
ENYISYIENV ENINIKNIDR YNLLYKHFCE NESTINCKME LLSVEQLKEF GGCVMKQHIN   240
SMTINIQDFK IENKENSLGF ILNLPLNKKK YQIELWGNRQ IKKGNKDNYK TLVDFINTYG   300
QNIIFTIKNN KIYVVFSYEC ELKEKEINFD KIVGIDVNFK HALFVASERD KNPLQDNNQL   360
KGYINLYGYL LEHNEFTSLL TKEELDIYKE IAKGVTFCPL EYNLLFTRIE NKGGKSNDKE   420
QVLSKLLYSL QIKLKNENKI QEYIYVSCVN KLRAKYVSYF ILKEKYYEKQ KEYDIEMGFT   480
```

```
DDSTESKESM DKRRLEFPFR NTQIANGFLE KLSNVQQDIN GCLKNIINYA YKVFEQNGFG    540
VIALENLENS NFEKTQVLPT IKSLLRYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILR ATKKGQFNIL AELKKQNKIK IFEIEK                              756

SEQ ID NO: 40            moltype = AA   length = 756
FEATURE                  Location/Qualifiers
REGION                   1..756
                         note = Description of Artificial Sequence: Synthetic
                         polypeptide
source                   1..756
                         mol_type = protein
                         organism = synthetic construct
SEQUENCE: 40
MTTKQVKSIV LKVKNTNECP ITKDVINEYK KYYNICSEWI KDNLTSITIG DIASFLKEAT     60
NKDTIPTYIN MGLSEEWKYK PIYHLFTDDY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPGQDNNQL    360
KGYINLYGYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIINYA YKVFEQNGFG    540
VIALENLENS NFEKTQVLPT IKSLLRYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILR ATKKGQFNIL AELKKQNKIK IFEIEK                              756

SEQ ID NO: 41            moltype = AA   length = 756
FEATURE                  Location/Qualifiers
REGION                   1..756
                         note = Description of Artificial Sequence: Synthetic
                         polypeptide
source                   1..756
                         mol_type = protein
                         organism = synthetic construct
SEQUENCE: 41
MTTKQVKSIV LKVKNTNECP ITKDVINEYK KYYNICSEWI KDNLTSITIG DIASFLKEAT     60
NKDTIPTYIN MGLSEEWKYK PIYHLFTDRY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPGQDNNQL    360
KGYINLYGYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIINYA YKVFEQNGFG    540
VIALENLENS NFEKTQVLPT IKSLLRYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILR ATKKGQFNIL AELKKQNKIK IFEIEK                              756

SEQ ID NO: 42            moltype = RNA  length = 56
FEATURE                  Location/Qualifiers
misc_feature             1..56
                         note = Description of Artificial Sequence: Synthetic
                         oligonucleotide
source                   1..56
                         mol_type = other RNA
                         organism = synthetic construct
SEQUENCE: 42
cctgttgtga atactctttt ataggtatca aacaactgag aatggtgcgt cctagg         56

SEQ ID NO: 43            moltype = DNA  length = 20
FEATURE                  Location/Qualifiers
misc_feature             1..20
                         note = Description of Unknown: AAVS1 mammalian target
                         sequence
source                   1..20
                         mol_type = genomic DNA
                         organism = unidentified
SEQUENCE: 43
tgagaatggt gcgtcctagg                                                 20

SEQ ID NO: 44            moltype = RNA  length = 56
FEATURE                  Location/Qualifiers
misc_feature             1..56
                         note = Description of Artificial Sequence: Synthetic
                         oligonucleotide
```

| | | |
|---|---|---|
| source | 1..56 | |
| | mol_type = other RNA | |
| | organism = synthetic construct | |
| SEQUENCE: 44 | | | cctgttgtga atactctttt ataggtatca aacaactcca gaccaccaat gggcac    56

| | | |
|---|---|---|
| SEQ ID NO: 45 | moltype = DNA  length = 20 | |
| FEATURE | Location/Qualifiers | |
| misc_feature | 1..20 | |
| | note = Description of Unknown: VEGFA mammalian target sequence | |
| source | 1..20 | |
| | mol_type = genomic DNA | |
| | organism = unidentified | |
| SEQUENCE: 45 | | | tccagaccac caatgggcac    20

| | | |
|---|---|---|
| SEQ ID NO: 46 | moltype = RNA  length = 56 | |
| FEATURE | Location/Qualifiers | |
| misc_feature | 1..56 | |
| | note = Description of Artificial Sequence: Synthetic oligonucleotide | |
| source | 1..56 | |
| | mol_type = other RNA | |
| | organism = synthetic construct | |
| SEQUENCE: 46 | | | cctgttgtga atactctttt ataggtatca aacaacccgc cgcttcctga gccatc    56

| | | |
|---|---|---|
| SEQ ID NO: 47 | moltype = DNA  length = 20 | |
| FEATURE | Location/Qualifiers | |
| misc_feature | 1..20 | |
| | note = Description of Unknown: EMX1 mammalian target sequence | |
| source | 1..20 | |
| | mol_type = genomic DNA | |
| | organism = unidentified | |
| SEQUENCE: 47 | | | ccgccgcttc ctgagccatc    20

| | | |
|---|---|---|
| SEQ ID NO: 48 | moltype =   length = | |
| SEQUENCE: 48 | | |
| 000 | | |

| | | |
|---|---|---|
| SEQ ID NO: 49 | moltype = AA  length = 756 | |
| FEATURE | Location/Qualifiers | |
| REGION | 1..756 | |
| | note = Description of Artificial Sequence: Synthetic polypeptide | |
| source | 1..756 | |
| | mol_type = protein | |
| | organism = synthetic construct | |
| SEQUENCE: 49 | | |

```
MTTKQVKSIV LKVKNTNECP ITKDVINEYK KYYNICSEWI KDNLTSITIG DIASFLKEAR   60
NKDTIPTYIN MGLSEEWKYK PIYHLFTDRY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNPLQGNNQL  360
KGYINLYGYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIINYA YKVFEQNGFG  540
VIALENLENS NFEKTQVLPT IKSLLRYHKL ENQNINNINA SDKVKEYIEK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILR ATKKGQFNIL AELKKQNKIK IFEIEK                           756
```

| | | |
|---|---|---|
| SEQ ID NO: 50 | moltype = AA  length = 756 | |
| FEATURE | Location/Qualifiers | |
| REGION | 1..756 | |
| | note = Description of Artificial Sequence: Synthetic polypeptide | |
| source | 1..756 | |
| | mol_type = protein | |
| | organism = synthetic construct | |
| SEQUENCE: 50 | | |

```
MTTKQVKSIV LKVKNTNECP ITKDVINEYK KYYNICSEWI KDNLTSITIG DIASFLKEAR   60
NKDTIPTYIN MGLSEEWKYK PIYHLFTDRY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
```

```
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNGLQGNNQL    360
KGYINLYGYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIINYA YKVFEQNGFG    540
VIALENLENS NFEKTQVLPT IKSLLRYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILR ATKKGQFNIL AELKKQNKIK IFEIEK                              756

SEQ ID NO: 51          moltype = AA  length = 756
FEATURE                Location/Qualifiers
REGION                 1..756
                       note = Description of Artificial Sequence: Synthetic
                       polypeptide
source                 1..756
                       mol_type = protein
                       organism = synthetic construct
SEQUENCE: 51
MTTKQVKSIV LKVKNTNECP ITKDVINEYK KYYNICSEWI KDNLTSITIG DIASFLKEAR     60
NKDTIPTYIN MGLSEEWKYK PIYHLFTDRY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPLQGNNQL    360
KGYINLYGYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIINYA YKVFEQNGFG    540
VIALENLENS NFEKTQVLPT IKSLLRYHKL RNQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILR ATKKGQFNIL AELKKQNKIK IFEIEK                              756

SEQ ID NO: 52          moltype = AA  length = 756
FEATURE                Location/Qualifiers
REGION                 1..756
                       note = Description of Artificial Sequence: Synthetic
                       polypeptide
source                 1..756
                       mol_type = protein
                       organism = synthetic construct
SEQUENCE: 52
MTTKQVKSIV LKVKNTNECP ITKDVINEYK KYYNICSEWI KDNLTSITIG DIASFLKEAR     60
NKDTIPTYIN MGLSEEWKYK PIYHLFTDRY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNGLQGNNQL    360
KGYINLYGYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIINYA YKVFEQNGFG    540
VIALENLENS NFEKTQVLPT IKSLLRYHKL RNQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILR ATKKGQFNIL AELKKQNKIK IFEIEK                              756

SEQ ID NO: 53          moltype = AA  length = 756
FEATURE                Location/Qualifiers
REGION                 1..756
                       note = Description of Artificial Sequence: Synthetic
                       polypeptide
source                 1..756
                       mol_type = protein
                       organism = synthetic construct
SEQUENCE: 53
MTTKQVKSIV LKVKNTNECP ITKDVINEYK KYYNICSEWI KDNLTSITIG DIASFLKEAR     60
NKDTIPTYIN MGLSEEWKYK PIYHLFTDRY HEKSANNLLY AYFKEKNLDC YNGNILNLSE    120
TYYRRNGYFK SVVGNYRTKI RTLNYKIKRK NVDENSTNED IELQVMYEIA KRKLNIKKDW    180
ENYISYIENV ENINIKNIDR YNLLYKHFCE NESTINCKME LLSVEQLKEF GGCVMKQHIN    240
SMTINIQDFK IENKENSLGF ILNLPLNKKK YQIELWGNRQ IKKGNKDNYK TLVDFINTYG    300
QNIIFTIKNN KIYVVFSYEC ELKEKEINFD KIVGIDVNFK HALFVASERD KNPGQDNNQL    360
KGYINLYKYL LEHNEFTSLL TKEELDIYKE IAKGVTFCPL EYNLLFTRIE NKGGKSNDKE    420
QVLSKLLYSL QIKLKNENKI QEYIYVSCVN KLRAKYVSYF ILKEKYYEKQ KEYDIEMGFT    480
DDSTESKESM DKRRLEFPFR NTQIANGFLE KLSNVQQDIN GCLKNIINYA YKVFEQNGFG    540
VIALENLENS NFEKTQVLPT IKSLLRYHKL ENQNINNINA SDKVKEYIEK EYYELTTNEN    600
NEIVDAKYTK KGIIKVKKAN FFNLMMKSLH FASNKDEFIL LSNNGKTQIA LVPSEYTSQM    660
DSIEHCLYVD KNGKKVDKKK VRQKQETHIN GLNADFNAAN NIKYIIENEN LRKLFCGKLK    720
VSGYNTPILR ATKKGQFNIL AELKKQNKIK IFEIEK                              756
```

```
SEQ ID NO: 54            moltype = AA   length = 756
FEATURE                  Location/Qualifiers
REGION                   1..756
                         note = Description of Artificial Sequence: Synthetic
                         polypeptide
source                   1..756
                         mol_type = protein
                         organism = synthetic construct
SEQUENCE: 54
MTTKQVKSIV LKVKNTNECP ITKDVINEYK KYYNICSEWI KDNLTSITIG DIASFLKEAT   60
NKDTIPTYIN MGLSEEWKYK PIYHLFTDRY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNPGQGNNQL  360
KGYINLYKYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIINYA YKVFEQNGFG  540
VIALENLENS NFEKTQVLPT IKSLLRYHKL ENQNINNINA SDKVKEYIEK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILR ATKKGQFNIL AELKKQNKIK IFEIEK                           756

SEQ ID NO: 55            moltype = AA   length = 756
FEATURE                  Location/Qualifiers
REGION                   1..756
                         note = Description of Artificial Sequence: Synthetic
                         polypeptide
source                   1..756
                         mol_type = protein
                         organism = synthetic construct
SEQUENCE: 55
MTTKQVKSIV LKVKNTNECP ITKDVINEYK KYYNICSEWI KDNLTSITIG DIASFLKEAR   60
NKDTIPTYIN MGLSEEWKYK PIYHLFTDRY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNPGQGNNQL  360
KGYINLYKYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIINYA YKVFEQNGFG  540
VIALENLENS NFEKTQVLPT IKSLLRYHKL ENQNINNINA SDKVKEYIEK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILR ATKKGQFNIL AELKKQNKIK IFEIEK                           756

SEQ ID NO: 56            moltype = AA   length = 756
FEATURE                  Location/Qualifiers
REGION                   1..756
                         note = Description of Artificial Sequence: Synthetic
                         polypeptide
source                   1..756
                         mol_type = protein
                         organism = synthetic construct
SEQUENCE: 56
MTTKQVKSIV LKVKNTNECP ITKDVINEYK KYYNICSEWI KDNLTSITIG DIASFLKEAR   60
NKDTIPTYIN MGLSEEWKYK PIYHLFTDRY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNGGQDNNQL  360
KGYINLYKYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIINYA YKVFEQNGFG  540
VIALENLENS NFEKTQVLPT IKSLLRYHKL ENQNINNINA SDKVKEYIEK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILR ATKKGQFNIL AELKKQNKIK IFEIEK                           756

SEQ ID NO: 57            moltype = AA   length = 756
FEATURE                  Location/Qualifiers
REGION                   1..756
                         note = Description of Artificial Sequence: Synthetic
                         polypeptide
source                   1..756
                         mol_type = protein
                         organism = synthetic construct
SEQUENCE: 57
MTTKQVKSIV LKVKNTNECP ITKDVINEYK KYYNICSEWI KDNLTSITIG DIASFLKEAR   60
```

```
NKDTIPTYIN MGLSEEWKYK PIYHLFTDRY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNPGQDNNQL  360
KGYINLYKYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIIYNA YKVFEQNGFG  540
VIALENLENS NFEKTQVLPT IKSLLRYHKL RNQNINNINA SDKVKEYIEK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILR ATKKGQFNIL AELKKQNKIK IFEIEK                           756

SEQ ID NO: 58           moltype = AA   length = 756
FEATURE                 Location/Qualifiers
REGION                  1..756
                        note = Description of Artificial Sequence: Synthetic
                         polypeptide
source                  1..756
                        mol_type = protein
                        organism = synthetic construct
SEQUENCE: 58
MTTKQVKSIV LKVKNTNECP ITKDVINEYK KYYNICSEWI KDNLTSITIG DIASFLKEAR   60
NKDTIPTYIN MGLSEEWKYK PIYHLFTDRY HEKSANNLLY AYFKEKNLDC YNGNILNLSE  120
TYYRRNGYFK SVVGNYRTKI RTLNYKIKRK NVDENSTNED IELQVMYEIA KRKLNIKKDW  180
ENYISYIENV ENINIKNIDR YNLLYKHFCE NESTINCKME LLSVEQLKEF GGCVMKQHIN  240
SMTINIQDFK IENKENSLGF ILNLPLNKKK YQIELWGNRQ IKKGNKDNYK TLVDFINTYG  300
QNIIFTIKNN KIYVVFSYEC ELKEKEINFD KIVGIDVNFK HALFVASERD KNGGQGNNQL  360
KGYINLYKYL LEHNEFTSLL TKEELDIYKE IAKGVTFCPL EYNLLFTRIE NKGGKSNDKE  420
QVLSKLLYSL QIKLKNENKI QEYIYVSCVN KLRAKYVSYF ILKEKYYEKQ KEYDIEMGFT  480
DDSTESKESM DKRRLEFPFR NTQIANGFLE KLSNVQQDIN GCLKNIIYNA YKVFEQNGFG  540
VIALENLENS NFEKTQVLPT IKSLLRYHKL RNQNINNINA SDKVKEYIEK EYYELTTNEN  600
NEIVDAKYTK KGIIKVKKAN FFNLMMKSLH FASNKDEFIL LSNNGKTQIA LVPSEYTSQM  660
DSIEHCLYVD KNGKKVDKKK VRQKQETHIN GLNADFNAAN NIKYIIENEN LRKLFCGKLK  720
VSGYNTPILR ATKKGQFNIL AELKKQNKIK IFEIEK                           756

SEQ ID NO: 59           moltype = DNA   length = 2268
FEATURE                 Location/Qualifiers
misc_feature            1..2268
                        note = Description of Artificial Sequence: Synthetic
                         polynucleotide
source                  1..2268
                        mol_type = other DNA
                        organism = synthetic construct
SEQUENCE: 59
atgactacca agcaagtcaa atccatagta ctgaaggtta agaatacaaa tgaatgccca    60
atcaccaagg atgtgatcaa cgagtacaag aagtattata atatctgtag cgagtggatt   120
aaagataatc tgacctctat aaccatcggc gacatcgcct cttttttgaa agaagcaaca   180
aacaaagata ctatcccaac gtacatcaat atgggactta gtgaagagtg aaatacaag    240
cctatctacc atctctttac cgacagatac cacgagaaat cagccaacaa cctgcttat    300
gcttacttta aggaaaagaa tctgattgtt tataatgaca aaatcctcaa cttgtccgaa   360
acatactacc gtcgcaatgg atacttcaag tcggtagtgg ggaactatcg tacaaaaatt   420
cgcacactta actataagat taagagaaaa aacgttgacg agaatagcac caatgaagat   480
attgaactcc aagttatgta tgaaatcgca aagcgcaagc tgaacattaa gaaggactgg   540
gagaattata tctcatacat tgagaatgtc gagaacatca acatcaaaaa tatcgatcgg   600
tacaacctgc tatacaagca tttctgtgaa aatgagtcca ccatcaactg caagatggag   660
ttgctctctg tggaacagct caaagagttc ggggttgtg tgatgaagca gcacataaat    720
tccatgacga taaacataca ggactttaag attgaaaaca aggagaactc actgggtttc   780
atcctgaacc tgcccttgaa caagaaaaag taccagatag aactgtgggg gaaccgacaa   840
atcaaaaaag ggaataagga taactataag acgctggttg actttatcaa cacttatggt   900
cagaacatta ttttcaccat taaaaataat aaaatttacg tcgtgttcag ctacgagtgt   960
gaattaaagg agaaggaaat caatttcgac aagattgtcg ggattgatgt gaatttcaag  1020
cacgccctgt ttgtggcttc cgagcgggac aaaaacccac tgcaagataa taccagcta   1080
aaagggtaca taaacctgta tggctatctt ctggagcata atgaatttac aagcctgctg  1140
accaaggagg aactggacat ttataaagaa attgcgaagg gcgtcacatt ttgtcccctg  1200
gagtacaact tgcttttcac tagaatagag aataagggcg gaaagtctaa cgacaaagaa  1260
caggtgctga gcaagctgct ctatagcttg cagatcaaac tcaaaaatga aaataagatt  1320
caggagtata tctatgtgag ttgcgtaaat aagctccgag ccaaatacgt gtcatacttt  1380
atcttgaaag aaaaatacta cgaaaagcag aaagagtacg acatcgagat gggcttcacg  1440
gatgactcga ctgagtctaa agagtctatg acaagaggc ggctggagtt ccccttagg    1500
aatactcaga ttgctaatgg cttcctcgaa aaactctcca acgtgcagca agatatcaac  1560
ggatgcttaa agaatattat taactatgcc tataaagtat cgagcaaaa cggatttgga   1620
gtcatcgcac tggaaaactt agagaacagc aacttcgaaa agacacaggt cttacctaca  1680
atcaagagtc tacttcggta tcataagttg agaatcaga atattaataa tattaacgcg  1740
agtgacaagg tgaaagagta catagagaag gagtattacg aactaactac caacgagaac  1800
aatgaaaatag tcgatgctaa atacactaaa aagggaatta tcaaggtgaa aaagagctaac  1860
ttttttaacc taatgatgaa atccctgcac tttgccagta caaagatgaa gttcatcttg   1920
ctgagcaata acggtaaaac acaaattgca ctggttccga gcgagtatac ctcccagatg  1980
gactctatag aacactgcct ctacgtggac aaaaatggga aaaagtgga caaaaagaag   2040
```

```
gttaggcaga agcaggaaac tcacatcaac ggcctcaacg ccgatttcaa cgccgctaac  2100
aatataaagt acatcatcga aaacgagaat cttaggaagc tgttttgcgg caagctgaag  2160
gtgtcaggtt ataacacccc tatcctcaga gccaccaaaa agggccagtt caatattctg  2220
gcagagctga agaagcagaa taagattaaa atcttcgaga ttgagaaa              2268

SEQ ID NO: 60           moltype = DNA  length = 2268
FEATURE                 Location/Qualifiers
misc_feature            1..2268
                        note = Description of Artificial Sequence: Synthetic
                         polynucleotide
source                  1..2268
                        mol_type = other DNA
                        organism = synthetic construct
SEQUENCE: 60
atgaccacca agcaagtgaa gagcatcgtg ctgaaggtga agaacaccaa cgagtgcccc   60
atcaccaagg acgtgatcaa cgagtacaag aagtactaca acatctgcag cgagtggatc  120
aaggacaacc tgacaagcat caccatcggc gacatcgcta gcttcctgaa ggaggccacc  180
aacaaggaca ccatccccac ctacatcaac atgggcctga gcgaggagtg gaagtacaag  240
cccatctacc acctgttcac cgacagatac cacgagaaga cgccaataa  cctgctgtac  300
gcctatttca aggagaagaa cctggactgc tacaacggca acatcctgaa cctgagcgag  360
acctactaca agaaaacgg ctacttcaag agcgtggtgg caactacag aaccaagatc   420
agaaccctga actataagat caagcgtaaa aacgtgagca agaacagcac caacgaggac  480
atcgagctgc aagtgatgta cgagatcgcc aaaagaaagc tgaacatcaa gaaggactgg  540
gagaactaca tcagctacat cgagaacgtg gaaaacatca atattaagaa catcgacaga  600
tataaccttt tgtacaagca tttctgcgag aacgagagca ccatcaactg caagatggag  660
ctgctgagcg tggagcagct gaaggagttc ggcggctgg tgatgaagca gcacatcaac   720
agcatgacca tcaacatcca agacttcaag atcgaaaaca agaaaaacag cctgggcttt  780
atcctcaacc ttccactgaa caagaagaag tatcagatcg agctgtgggg caacagacag  840
atcaagaagg caacaagga caactataag acgttagtgg acttcatcaa cacctacggg  900
cagaacatca tcttccaccat caagaacaac aagatctacg tggtgttcag ctacgagtgc  960
gagctgaaag agaaggaaat caacttcgac aagatcgtgg catcgacgt gaacttcaag  1020
cacgccctgt tcgtggctag cgagagagac aagaaccccc tgcaagacaa caatcagctg  1080
aagggctaca tcaacctgta cggctacctg ctggagcaca acgagttcac aagcctgctg  1140
accaaggagg agctggacat ctacaaggag atcgccaagg tgtcaccttc ctgcccccatg  1200
gagtacaacc ttcttttcac aagaatcgag aacaaggcg gcaagagca cgacaaggag  1260
caagtgctga gcaagctgct gtacagcctg cagatcaagc tgaagaacga gaacaagatc  1320
caagagtaca tctacgtgag ctgcgtgaac aagctgagag ccaagtacgt gagctacttc  1380
atcctgaagg aaaagtacta cgagaagcag aaggagtacg acatcgagat gggcttcacc  1440
gacgcacga ccgagagcaa ggagacatg gacaagagaa gactggagtt ccccttcaga    1500
aacacacaga tcgccaacgg gttcctggaa aagctgagca acgtgcagca agacatcaac  1560
ggctgcctga gaacatcat caactacgcc tacaaggtgt cgagcagaa cggcttcggc   1620
gtgatcgccc tggagaacct ggagaacagc aacttcgaga agacccaagt gctgccacc   1680
atcaagagcc tgctgagata ccacaagctg gagaaccaaa atatcaataa tatcaatgct  1740
agcgacaagg tgaaggagta catcgagaag gagtactacg agctgaccac caacgagaac  1800
aacgagatct ggacgccaa gtacactaag aagggtataa tcaaggtgaa gaaggccaac  1860
ttcttcaacc tgatgatgaa gagcctgcac ttcgctagca caaggacga gttcatcctg  1920
ctgagcaaca acggcaagac acagatcgca ctggtgccta cggctacctg atctcagatg  1980
gacagcatcg agcactgcct gtacgtggac aagaacggca agaaggtgga caagaagaag  2040
gtgagacaga agcaagagac ccacatcaac ggcctgaacg ccgacttcaa cgccgccaac  2100
aacatcaagt atatcatcga gaacgagaac ctgaaaagc tgttctgcgg caagctgaag   2160
gtgagcggct acaacacccc catcctgaga gccacaaaga agggcagtt taacatcctg    2220
gccgagctga agaagcagaa caagatcaag atctttgaga tcgagaag              2268

SEQ ID NO: 61           moltype = DNA  length = 2268
FEATURE                 Location/Qualifiers
misc_feature            1..2268
                        note = Description of Artificial Sequence: Synthetic
                         polynucleotide
source                  1..2268
                        mol_type = other DNA
                        organism = synthetic construct
SEQUENCE: 61
atgaccacca agcaggtgaa gagcatcgtg ctgaaggtga agaacaccaa cgagtgcccc   60
atcaccaagg acgtgatcaa cgagtacaag aagtactaca acatctgcag cgagtggatc  120
aaggacaacc tgaccagcat caccatcggc gacatcgcca gcttcctgaa ggaggccacc  180
aacaaggaca ccatccccac ctacatcaac atgggcctga gcgaggagtg gaagtacaag  240
cccatctacc acctgttcac cgaccggtac cacgagaaga cgccaacaa  cctgctgtac  300
gcctacttca aggagaagaa cctggactgc tacaacggca acatcctgaa cctgagcgag  360
acctactacc ggcggaacgg ctacttcaag agcgtggtgg caactaccg gaccaagatc  420
cggaccctga actacaagat caagcggaag aacgtggacg agaacagcac caacgaggac  480
atcgagctgc aggtgatgta cgagatcgcc aagcggaagc tgaacatcaa gaaggactgg  540
gagaactaca tcagctacat cgagaacgtg gagaacatca acatcaagaa catcgaccgg  600
tacaacctgc tgtacaagca cttctgcgag aacgagagca ccatcaactg caagatggag  660
ctgctgagcg tggagcagct gaaggagttc ggcggctgg tgatgaagca gcacatcaac   720
agcatgacca tcaacatcca ggacttcaag atcgaaaaca ggagaacag cctgggcttc   780
atcctgaacc tgcccctgaa caagaagaag taccagatcg agctgtgggg caaccggcag  840
atcaagaagg caacaagga caactacaag accctggtgg acttcatcaa cacctacggc  900
cagaacatca tcttccaccat caagaacaac aagatctacg tggtgttcag ctacgagtgc  960
gagctgaagg agaaggagat caacttcgac aagatcgtgg catcgacgt gaacttcaag  1020
```

```
cacgccctgt tcgtggccag cgagcgggac aagaaccccc tgcaggacaa caaccagctg 1080
aagggctaca tcaacctgta cggctacctg ctggagcaca acgagttcac cagcctgctg 1140
accaaggagg agctggacat ctacaaggag atcgccaagg gcgtgacctt ctgcccctg  1200
gagtacaacc tgctgttcac ccggatcgag aacaagggcg gcaagagcaa cgacaaggag 1260
caggtgctga gcaagctgct gtacagcctg cagatccgag tgaagaacga gaacaagatc 1320
caggagtaca tctacgtgag ctgcgtgaac aagctgcggg ccaagtacgt gagctacttc 1380
atcctgaagg agaagtacta cgagaagcag aaggagtacg acatcgagat gggcttcacc 1440
gacgacagca ccgagagcaa ggagagcatg gacaagcggc ggctggagtt ccccttccgg 1500
aacacccaga tcgccaacgg cttcctggag aagctgagca acgtgcagca ggacatcaac 1560
ggctgcctga gaacatcat caactacgcc tacaaggtgt tcgagcagaa cggcttcggc 1620
gtgatcgccc tggagaacct ggagaacagc aacttcgaga agacccaggt gctgcccacc 1680
atcaagagcc tgctgcggta ccacaagctg gagaaccaga acatcaacaa catcaacgcc 1740
agcgacaagg tgaaggagta catcgagaag gagtactacg agctgaccac caacgagaac 1800
aacgagatcg tggacgccaa gtacaccaag aagggcatca tcaaggtgaa gaaggccaac 1860
ttcttcaacc tgatgatgaa gagcctgcac ttcgccagca caaggacga gttcatcctg 1920
ctgagcaaca acggcaagac ccagatcgcc ctggtgccca gcgagtacac cagccagatg 1980
gacagcatcg agcactgcct gtacgtggac aagaacggca gagaggtgga caagaagaag 2040
gtgcggcaga gcaggagac ccacatcaac ggcctgaacg ccgactttcaa cgccgccaac 2100
aacatcaagt acatcatcga gaacgagaac ctgcggaagc tgttctgcgg caagctgaag 2160
gtgagcggct acaacacccc catcctgcgg gccaccaaga agggccagtt caacatcctg 2220
gccgagctga gaagcagaa caagatcaag atcttcgaga tcgagaag             2268

SEQ ID NO: 62           moltype = DNA  length = 2268
FEATURE                 Location/Qualifiers
misc_feature            1..2268
                        note = Description of Artificial Sequence: Synthetic
                         polynucleotide
source                  1..2268
                        mol_type = other DNA
                        organism = synthetic construct
SEQUENCE: 62
atgactacga aacaagtaaa gtctattgtg cttaaagtga agaatactaa cgagtgtccc  60
attaccaagg atgttataaa tgaatacaaa aaatattata acatctgcag cgaatggata 120
aaagataacc ttacttctat tactataggg gatatagcgt cctttctgac ggaggcgacg 180
aacaaagaca ctatcccgac ctacatcaac atgggctct  ccgaagaatg gaagtacaag 240
cctatctacc atcttttcac cgacagatat catgagaaat ccgcaaataa tttgttgtat 300
gcttacttca agagaagaa cttggattgc tacaacggta atattcttaa tctctcagag 360
acttattaca ggaggaacgg gtactttaaa agcgtggtcg gaaattatcg cacaaaaata 420
cgcacattga attataaaat caagcgaaaa aacgtcgatg aaaactctac aaacgaggat 480
attgagctgc aagtgatgta tgaaatcgca aagagaaaac tgaacatcaa gaaggattgg 540
gagaattaca tatcctatat cgaaaacgtg gagaatatca acatcaagaa catagataga 600
tataatctgc tctataagca ttttttgcgaa aacgagtcta caattaactg caagatggag 660
ctgctttccg tagagcaact taaggaattt ggtggatgcg ttatgaagca gcatatcaac 720
agtatgacta ttaatataca ggatttttaag atcgagaata aggaaaactc cctgggcttt 780
attctcaatc tgccctgaa caaaaaaag tatcagatag aactctgggg caatagacag 840
attaagaaag gtaataagga caattataaa accctcgtag actttataaa tacatacggg 900
caaaacatca ttttcacgat taagaataac aaaatttatg ttgtgttctc ctatgagtgt 960
gaactgaagg agaaagagat taacttcgat aagatagttg ggattgatgt gaactttaaa 1020
cacgcccttt tcgttgcgtc cgagagggac aagaatccct tgcaggataa taatcaactg 1080
aagggttaca tcaatctcta tggatacttg ctggaacaca cgaattcac aagtctcctg 1140
acgaaggagg aactcgatat ttataaggaa atagccaagg gagttacctt ttgtccgctc 1200
gagtataatc ttctcttcac acggatcgaa aacaaaggag gaaagagcaa tgataaagaa 1260
caagtacttt ccaaacttct ttatagtctc caaattaagc tgaagaacga gaacaagatc 1320
caggagtata tatgtgtc atgtgtgaat aagctgcgag cgaaatacgt atcttacttc 1380
attctcaaag aaaaatatta tgagaagcag aaagaataca atattgaaat gggcttttaca 1440
gacgactcaa ccgagtccaa agagtctatg gacaaaagac gattggagtt cccgtttcga 1500
aatacacaga tcgccaatgg tttcctgag aagctgagta atgtgcagca agatataaat 1560
ggctgcctta agaatataat taactacgct tacaaggtgt ttgaacaaaa tgggttcggc 1620
gttatcgccc tcgaaaacct tgaaaattct aactttgaaa agacgcaagt ccttcctaca 1680
attaagtccc ttcttcgcta tcacaaactg gagaaccaaa atatcaataa cattaatgct 1740
tcagataaag ttaaggaata catagaaaag gagtactacg aacttaccac caacgaaaac 1800
aatgaaattg tagacgctaa gtacacaaag aagggcatta taaagttaa aaaagcgaac 1860
ttctttaact tgatgatgaa atcacttcat tttgcgtcaa caaagacga gtttatcttg 1920
ctcagcaata tggtaagac tcaaatcgcc ctcgtcccct ctgagtatac aagccagatg 1980
gattctattg agcactgtct ctacgtggat aagaacggaa agaaagtaga caagaaaaag 2040
gtcaggcaga acaagagac acacatcaat gggctgaatg ccgactttaa tgccgcaaac 2100
aacataaagt atataatcga gaacgaaaac ctccgaaagc tgttttgcgg taaactgaaa 2160
gtgagcgggt acaatacacc tatcctgcgc gctaccaaaa aaggccaatt taatatactg 2220
gctgagctca agaagcaaaa taaaatcaaa atctttgaga tagagaag             2268

SEQ ID NO: 63           moltype = DNA  length = 2268
FEATURE                 Location/Qualifiers
misc_feature            1..2268
                        note = Description of Artificial Sequence: Synthetic
                         polynucleotide
source                  1..2268
                        mol_type = other DNA
                        organism = synthetic construct
SEQUENCE: 63
```

```
atgaccacca agcaagtgaa atctatcgtg ctgaaggtga agaacaccaa cgaatgccct    60
atcaccaagg atgtgatcaa cgagtacaag aagtattata acatctgcag cgagtggatc   120
aaagataatt tgacaagcat caccatcggc gacatcgcct ccttcctgaa ggaagccacc   180
aacaaggata caatacccac ctacatcaac atgggcctga gcgaggaatg gaaatacaag   240
cccatctacc atctgtttac cgaccgctac cacgagaaga gcgccaacaa cctgctctac   300
gcttatttca aggagaagaa cctggactgc tacaatggaa atatcctgaa cctgtctgag   360
acatactaca aagaaaacgg ctatttcaag agtgtggtcg aaactacag gaccaaaatc    420
cggaccctga actacaagat caagcggaag aacgtggacg agaattctac caacgaggac   480
atcgagctgc aggtgatgta cgagatcgct aagcggaagc tgaatatcaa gaaagactgg   540
gagaactaca tcagctacat cgagaacgtg gaaaacatca acatcaagaa tatcgataga   600
tacaatctgc tgtacaagca cttctgcgag aacgagagca ccatcaactg caagatggaa   660
ctcctgagcg tggaacagct gaaagagttc ggcggctgtg tgatgaaaca acacatcaat   720
agcatgacca tcaacattca ggacttcaag atcgagaaga ggaaaatag cttgggcttc    780
atcctgaacc tgcctctgaa caagaagaag taccagatcg agctctgggg caacagacag   840
atcaagaaag gcaataagga taactacaaa accctggtcg atttcatcaa cacatacgtg   900
cagaacataa tctttacaat caagaacaac aaaatctacg tggtgttcag ctacgaatgt   960
gaactgaagg aaaaagaaat caacttcgac aagattgtgg catcgacgt gaactttaag   1020
cacgccctgt tcgtggcctc tgaaagagat aagaatcctc tgcaagacaa caatcaactg   1080
aagggctaca tcaacctcta cggctacctg ctggagcaca acgagttcac atctctgctg   1140
accaaggaag aactggatat ctataaggag attgccaagg tgttacatt ctgcccactg    1200
gaatacaacc tgctgttcac cagaatcgag aacaagggcg aaagtccaa cgacaaggag   1260
caggtgctgt ctaagctgct gtacagcctg cagatcgagt tgaagaataa aaacaagatc   1320
caggagtaca tctacgtgag ctgcgtgaac aagctgcggg ccaaatacgt gtcctacttc   1380
atcctgaagg aaaaatacta cgagaagcag aaggaatacg acatcgagat gggatttaca   1440
gacgacagca ccgagagcaa ggaaagcatg gacaaacgga gactgaatt cccccttcaga   1500
aacacccaga tcgccaacgg cttcctggaa aagctgcaga acgtgcaaca ggacatcaac   1560
ggctgtctga aaaacatcat taactacgcc tacaaagtct tcgagcagaa cggcttggc   1620
gtgatagctc tggaaaacct ggaaaacagc aacttcgaga agacccaggt gctgcctacc   1680
atcaagagcc tgctgcggta ccacaagctc gagaaccaga atattaacaa cattaatgcc   1740
agcgacaagg taaaggagta tattgagaag gaatactacg agctgacaac caacgagaac   1800
aacgaaatcg tggacgccaa gtacaccaag aagggcatca tcaaggtgaa gaaggccaat   1860
tttttcaacc tgatgatgaa gtctctgcac ttcgcctcta ataaagatga gttcatcctg   1920
ctgtccaaca atggcaaaac ccagatcgct ctggtgccta gcgagtatac tagccagatg   1980
gatagcatcg agcactgtct gtacgtggac aagaacggca agaaggtgga caagaagaaa   2040
gttagacaga aacaggagac ccacatcaac ggacttaacg ccgactttaa cgccgctaac   2100
aacataaagt acatcatcga gaatgagaac cttagaaagc tgttttgcgg caagctgaaa   2160
gtctccggct acaacacccc tatcctgaga gccacaaaga aggacagtt caacatcctg   2220
gccgagctga gaaacagaa caagatcaag atcttcgaga tcgagaag             2268

SEQ ID NO: 64          moltype = DNA  length = 2268
FEATURE                Location/Qualifiers
misc_feature           1..2268
                       note = Description of Artificial Sequence: Synthetic
                        polynucleotide
source                 1..2268
                       mol_type = other DNA
                       organism = synthetic construct
SEQUENCE: 64
atgaccacta agcaagtgaa atccatcgtc ttgaaagtaa agaataccaa tgagtgccct    60
attacaaagg acgttatcaa tgagtataaa aaatactaca acatctgttc tgaatggatt   120
aaagacaacc tcacgagcat cactatagga gatatcgcct ccttcctgaa ggaggcaacc   180
aacaaggata ccatccctac atatataaac atggggcttt cagaggagtg gaaatacaag   240
cccatttatc accttttcac agatagatac cacgaaaaa gtgcaaataa cttgctttac    300
gcttacttta agagaaaaa cttggactgt tacaatggta acattctgaa cctgtccgag   360
acatactaca gacggaacgg ctacttcaaa tcagtcgtcg ggaattatag gaccaagatc   420
cggacccttga actacaaaat taaagaaaa atgttgatg agaatagcac aaacgaagac   480
attgagctgc aagtaatgta tgagattgca aagagaaagc tgaacatcaa aaaggattgg   540
gagaattaca tatcctacat tgagaatgtg gaaaatatca acattaagaa tatagaccgc   600
tacaacctgc tgtataaaca cttctgcgag aatgaaagca ctataaattg caagatggag   660
ctgctgtcag tggagcagtt gaaagaattt ggagggtgtg tgatgaagca acatatcaat   720
agtatgacaa ttaacataca ggacttcaag attgaaaaca ggagaattc cctgggattc   780
atcctcaatc tgccattgaa taaaagaaa taccaaatag aattgtgggg aaaccgacag   840
atcaagaagg gaaataagga caactataag accctggtcg acttatcaa cacatatgc     900
cagaacatta ttttcactat aaaaaacaac aagatctacg tggtattcag ctacgagtgt   960
gagctgaaag agaaagaaat taattttgac aaaattgtag gaatcgatgt gaacttcaaa   1020
cacgccctgt tcgtcgccag cgaaaagaga caagaatccgc tgcaggataa caatcagctg   1080
aagggctaca tcaatctcta tggttatctc ctggagcaca atgaattcac aagtctgctg   1140
accaaagagg aattggatat ctacaaggaa atcgccaagg gggtcacctt ttgtccactg   1200
gagtacaacc tgctgttcac gcgcatcgag aataaaggcg ggaaagtaa tgataaagaa   1260
caagtactga gtaagctgtt gtatagcctg cagattaagc tcaagaatga aaacaagatc   1320
caggagtaca tttacgtgag ctgcgtcaat aagctgaggg ctaagtacgt gtcatatttt   1380
attctcaaag aaaagtatta tgagaaacag aaagagtacg acatcgagat gggatttaca   1440
gacgattcta ccgaaagcaa ggaatcaatg acaagcgcc gcttggagtt tccttttcaga   1500
aacactcaga tcgccaatgg attcctggaa agctgcaga acgtgcaaca ggacatcaat   1560
ggttgtctca gaacattat taactacgca tacaaggtgt tgaacagaa cgggttcggt    1620
gtgattgctc ttgaaaacct ggaaatagc aacttcgaaa agacacaggt cctcccaaca   1680
attaaatcac tgctcagata tcacaagctc gaaaaccaga acatcaataa tatcaacgcc   1740
tccgataaag tgaaagagta cattgaaaag gagtactacg agctgacaac caacgaaaac   1800
aatgaaattg tggatgctaa gtacaccaaa aagggaatta tcaaggtgaa gaaagctaat   1860
```

```
tttttcaacc tgatgatgaa gagcctgcat ttcgcttcca ataaggatga atttattctt   1920
ctgtcaaaca atggaaagac ccagatcgcc ctcgtgccaa gtgagtatac atcacagatg   1980
gactctattg agcattgtct ctatgtggat aagaacggaa agaaggtcga taagaagaaa   2040
gtgcgacaga aacaagagac gcatatcaat ggcctcaatg ctgattttaa tgccgcaaac   2100
aatataaaat atatcattga aaacgagaat ttgcgcaagc tgttttgcgg gaagctgaaa   2160
gtttctgggt ataataccc tatcttgcgc gccactaaga agggacaatt taatatcctg   2220
gctgagctga agaaacaaaa taaaatcaaa atattcgaga tcgagaag               2268

SEQ ID NO: 65           moltype = DNA  length = 2268
FEATURE                 Location/Qualifiers
misc_feature            1..2268
                        note = Description of Artificial Sequence: Synthetic
                        polynucleotide
source                  1..2268
                        mol_type = other DNA
                        organism = synthetic construct
SEQUENCE: 65
atgaccacca agcaggtgaa atcaattgtg ctgaaggtga agaataccaa tgagtgcccc    60
atcacaaagg acgtgatcaa cgagtacaag aagtactata atatctgtag cgagtggatc   120
aaggacaatc tgacatccat cactatcggc gacatcgcct ccttcctgaa ggaggccacc   180
aacaaggaca caatccctac ttacatcaac atgggactgt ccgaggaatg gaagtacaag   240
ccaatctacc acctgtttac cgataggtac cacgagaagt ccgccaataa cctgctgtac   300
gcatatttca aggaaaagaa tctggactgc tataacggga atatcctgaa cctgtccgag   360
acgtactacc ggcgcaacgg atacttcaag agcgtggtgg gcaactaccg caccaagatc   420
agaaccctga attacaagat taagagaaaa aacgtggacg aaaatagcac caacgaggat   480
atcgagctgc aggtgatgta cgagatcgcc aaacgcaaac tgaatatcaa gaaagattgg   540
gagaactata tcagttatat tgagaatgtg gagaatatca acatcaaaaa cattgacaga   600
tacaacctgc tctacaaaca cttttgtgaa aacgagtcta ccatcaattg taagatggag   660
ctgctgtccg tggaacagct gaaggagttt ggcggctgtg tgatgaagca gcatatcaac   720
tccatgacca tcaatatcca ggacttcaag atcgagaata ggagaaatag cctggggttt   780
atcctgaacc tgcctctgaa caagaagaag tatcagatcg agctgtgggg aaaccgccag   840
atcaagaagg gcaacaaaga taactataag accctggtgg acttcatcaa cacatacggg   900
cagaatatca tcttcaccat taagaacaac aagatctatg tggtgtttag ttacgagtgc   960
gagctgaaga agaaggagat taatttcgac aagatcgtgg gaatttacgt gaatttcaag  1020
cacgctctgt tcgtggcttc agagagagac aagaatccac tgcaggacaa caaccagtca  1080
aagggttaca ttaaccttta cggctacctg ctggagcaca atgagtttac cagcctgctg  1140
actaaggagg agctggacat ataacaagaa atcgccaagg gcgtgacgtt ctgcccactg  1200
gagtataacc tgctctcttac acggatcgag aataaaggcg ggaaaagcaa tgacaaggag  1260
caggtgctgt ctaaactgct gtattcactg cagatcagat tgaaaaacga gaacaagatc  1320
caggaataca tttacgtgag ctgcgtgaac aaactgaggg ccaagtatgt gtcatatttc  1380
atcctgaagg agaagtacta tgaagcag aaggagtacg catcgagat gggatttact  1440
gacgactcca ccgagagcaa ggagagcatg ataagagaa gactggagtt cccattccgc  1500
aacacccaga tcgccaacgg cttttctgaa aaactgatta acgtgccac ggacattaat  1560
ggatgtctga agaatatcat caactacgct tacaaggtgt ttgagcagaa cggatttggc  1620
gttatcgccc tggaaaacct ggaaaactcc aactttgaga agacacaggt gctgccaacc  1680
atcaagagcc tgctgaggta ccacaagctg gagaatcaga acattaacaa tatcaacgct  1740
agcgacaaag tgaaggagta cattgagaaa gaatactacg agctgaccac caatgaaaac  1800
aacgagatcg tggacgccaa gtataccaag aaaggcatca tcaaggtcaa aaaggctaat  1860
ttcttcaatc tgatgatgaa aagcctgcac tttgcctcca ataaagacga gtttattctc  1920
ctgagtaata acggcaagac ccagatcgcc ctggtgccat cagagtatac cagccagatg  1980
gattcaattg agcactgtct gtacgtgcag aagaatgaca agaaagtgga caagaagaaa  2040
gttcgacaga agcaggaaac ccacatcaat ggactcaatg cagatttcaa tgccgccaac  2100
aatatcaagt acattatcga gaacgagaac ctccggaagc tgttttgcgg caagctgaag  2160
gtgtccgggt acaataccc catcctgcgc gccaccaaga agggcagtt caacatcctg  2220
gccgaactga aaaagcagaa caagatcaag atctttgaga tcgagaag             2268

SEQ ID NO: 66           moltype = DNA  length = 2268
FEATURE                 Location/Qualifiers
misc_feature            1..2268
                        note = Description of Artificial Sequence: Synthetic
                        polynucleotide
source                  1..2268
                        mol_type = other DNA
                        organism = synthetic construct
SEQUENCE: 66
atgaccacaa agcaggtgaa gagcatcgtg ctgaaggtga agaacaccaa tgagtgccca    60
atcacaaagg acgtgatcaa cgagtacaag aagtactata atatctgttc cgagtggatc   120
aaggacaacc tgacctccat cacaatcggc gatatcgcct cttcctgaa ggaggccacc   180
aataaggata ccatcccac atatatcaac atgggagtgt ccgaggagtg gaagtacaag   240
cctatctatc acctgttcac agaccgttac cacgagaagt ctgccaacaa tctgctgtac   300
gcctacttca aggagaagaa cctggactgc tataacggca atatcctgaa tctgtccgag   360
acctactatc ggagaaacgg ctacttcaag tctgtggtgg gcaattatcg gaccaagatc   420
agaaacactga actacaagat caagaggaag aatgtggacg agaactctac aaatgaggat   480
atcgagctgc aggtgatgta cgagatcgcc aagcgcaagc tgaacatcaa gaaggactgg   540
gagaattaca tcagctatat cgagaacgtg gagaacatca atatcaagaa catcgatagg   600
tacaatctgc tgtataagca cttctgcgag aacgagagcc catcaattg taagatggag   660
ctgctgtccg tggagcagct gaaggagttt ggcggctgcg tgatgaagca gcacatcaac   720
tctatgacaa tcaatatcca ggatttcaag atcgagaaca aggagaatag cctgggcttt   780
atcctgaacc tgcccctgaa caagaagaag taccagatcg agctgtgggg caaccggcag   840
```

-continued

```
atcaagaagg gcaacaagga caattacaag accctggtgg atttcatcaa cacatatggc   900
cagaacatca tctttaccat caagaacaat aagatctacg tggtgttctc ctatgagtgt   960
gagctgaagg agaaggagat caactttgac aagatcgtgg gcatcgatgt gaatttcaag  1020
cacgccctgt ttgtggcctc tgagagagac aagaacccac tgcaggataa caatcagctg  1080
aagggctaca tcaacctgta cggctatctg ctggagcaca atgagttcac cagcctgctg  1140
acaaaggagg agctggacat ctacaaggag atcgccaagg gcgtgacctt ctgcccctg   1200
gagtataacc tgctgtttac aaggatcgag aacaagggcg gcaagtccaa tgataaggag  1260
caggtgctga gcaagctgct gtactccctg cagatcaagc tgaagaacga gaataagatc  1320
caggagtaca tctacgtgag ctgcgtgaat aagctgcgcg ccaagtacgt gagctatttc  1380
atcctgaagg agaagtacta tgagaagcag aaggagtacg acatcgagat gggcttttacc  1440
gacgatagca cagagtccaa ggagtctatg gataagaggc gcctggagtt cccttttcgg  1500
aacacccaga tcgccaatgg cttcctggag aagctgagca acgtgcagca ggacatcaat  1560
ggctgtctga agaacatcat caattacgcc tataaggtgt tcgagcagaa cggctttggc  1620
gtgatcgccc tggagaatct ggagaacagc aattttgaga agacccaggt gctgccaaca  1680
atcaagtccc tgctgcgtta ccacaagctg gagaaccaga atatcaacaa tatcaacgcc  1740
tctgacaagg tgaaggagta tatcgagaag gagtactatg agctgaccac aaatgagaac  1800
aatgagatcg tggatgccaa gtacaccaag aagggcatca tcaaggtgaa gaaggccaac  1860
ttctttaatc tgatgatgaa gtctctgcac ttcgccagca acaaggacga gtttatcctg  1920
ctgtccaaca atggcaagac ccagatcgcc ctggtgccca gcgagtacac atcccagatg  1980
gattctatcg agcactgcct gtatgtggac aagaacggca agaaggtgga taagaagaag  2040
gtgcggcaga agcaggagac ccacatcaac ggcctgaatg ccgacttcaa tgccgccaac  2100
aatatcaagt acatcatcga gaacgagaat ctgagaaagc tgttttgtgg caagctgaag  2160
gtgtccggct ataacacccc tatcctgcgt gccacaaaga agggccagtt caacatcctg  2220
gccgagctga agaagcagaa taagatcaag atctttgaga tcgagaag              2268
```